United States Patent
Ghinovker et al.

(10) Patent No.: US 9,702,693 B2
(45) Date of Patent: *Jul. 11, 2017

(54) APPARATUS FOR MEASURING OVERLAY ERRORS

(71) Applicant: KLA-Tencor Corporation, Milpitas, CA (US)

(72) Inventors: Mark Ghinovker, Migdal Ha'Emek (IL); Michael Adel, Zichron Ya'akov (IL); Walter D. Mieher, Los Gatos, CA (US); Ady Levy, Sunnyvale, CA (US); Dan Wack, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/136,855

(22) Filed: Apr. 22, 2016

(65) Prior Publication Data

US 2016/0313116 A1 Oct. 27, 2016

Related U.S. Application Data

(60) Continuation of application No. 14/873,120, filed on Oct. 1, 2015, now Pat. No. 9,347,879, which is a
(Continued)

(51) Int. Cl.
*G03F 7/20* (2006.01)
*G01B 11/27* (2006.01)
(Continued)

(52) U.S. Cl.
CPC ....... *G01B 11/272* (2013.01); *G01N 21/4785* (2013.01); *G01N 21/9501* (2013.01);
(Continued)

(58) Field of Classification Search
CPC ............ G01B 11/272; G01N 21/9501; G01N 21/4785; G03F 7/70633; Y10S 438/975; H01L 21/68; H01L 21/682; H01L 23/544
See application file for complete search history.

(56) References Cited

U.S. PATENT DOCUMENTS 3,594,085 A 7/1971 Wilmanns
4,103,998 A 8/1978 Nakazawa et al.
(Continued)

FOREIGN PATENT DOCUMENTS

EP 0818814 A2 1/1998
EP 0947828 A2 6/1999
(Continued)

OTHER PUBLICATIONS

US 5,841,144, 11/1998, Cresswell (withdrawn)
(Continued)

*Primary Examiner* — Jarrett Stark
(74) *Attorney, Agent, or Firm* — Kwan & Olynick LLP

(57) ABSTRACT

A metrology system for determining overlay is disclosed. The system includes an optical assembly for capturing images of an overlay mark and a computer for analyzing the captured images to determine whether there is an overlay error. The mark comprises first and second regions that each include at least two separately generated working zones, juxtaposed relative to one another, configured to provide overlay information in a first direction, and include a periodic structure having coarsely segmented elements. The mark comprises third and fourth regions that each include at least two separately generated working zones, juxtaposed relative to one another, configured to provide overlay information in a second direction, and include a periodic structure having coarsely segmented elements. Working zones of the first and second regions are diagonally opposed and spatially offset relative to one another, and the working zones of the
(Continued)

third and fourth regions are diagonally opposed and spatially offset relative to one another.

64 Claims, 16 Drawing Sheets

Related U.S. Application Data continuation of application No. 13/407,124, filed on Feb. 28, 2012, now Pat. No. 9,182,680, which is a continuation of application No. 12/410,317, filed on Mar. 24, 2009, now Pat. No. 8,138,498, which is a division of application No. 11/227,764, filed on Sep. 14, 2005, now Pat. No. 7,541,201, which is a continuation-in-part of application No. 09/894,987, filed on Jun. 27, 2001, now Pat. No. 7,068,833, and a continuation-in-part of application No. 10/729,838, filed on Dec. 5, 2003, now Pat. No. 7,317,531, and a continuation-in-part of application No. 10/785,396, filed on Feb. 23, 2004, now Pat. No. 7,385,699, which is a continuation-in-part of application No. 10/729,838, filed on Dec. 5, 2003, now Pat. No. 7,317,531.

(60) Provisional application No. 60/229,256, filed on Aug. 30, 2000, provisional application No. 60/698,535, filed on Jul. 11, 2005, provisional application No. 60/440,970, filed on Jan. 17, 2003, provisional application No. 60/449,496, filed on Feb. 22, 2003, provisional application No. 60/431,314, filed on Dec. 5, 2002, provisional application No. 60/504,093, filed on Sep. 19, 2003, provisional application No. 60/498,524, filed on Aug. 27, 2003.

(51) Int. Cl.
 G01N 21/47 (2006.01)
 G01N 21/95 (2006.01)
 H01L 21/68 (2006.01)
 H01L 23/544 (2006.01)

(52) U.S. Cl.
 CPC ......... *G03F 7/70633* (2013.01); *H01L 21/68* (2013.01); *H01L 21/682* (2013.01); *H01L 23/544* (2013.01); *Y10S 438/975* (2013.01)

(56) References Cited

U.S. PATENT DOCUMENTS

| | | |
|---|---|---|
| 4,167,337 A | 9/1979 | Jaerisch et al. |
| 4,200,395 A | 4/1980 | Smith et al. |
| 4,251,160 A | 2/1981 | Bouwhuis et al. |
| 4,332,473 A | 6/1982 | Ono |
| 4,475,811 A | 10/1984 | Brunner |
| 4,538,105 A | 8/1985 | Ausschnitt |
| 4,631,416 A | 12/1986 | Trutna, Jr. |
| 4,647,207 A | 3/1987 | Bjork |
| 4,703,434 A | 10/1987 | Brunner |
| 4,710,642 A | 12/1987 | McNeil |
| 4,714,874 A | 12/1987 | Morris et al. |
| 4,750,836 A | 6/1988 | Stein |
| 4,757,207 A | 7/1988 | Chappelow et al. |
| 4,757,707 A | 7/1988 | Harvey et al. |
| 4,778,275 A | 10/1988 | van den Brink et al. |
| 4,782,288 A | 11/1988 | Vento |
| 4,818,110 A | 4/1989 | Davidson |
| 4,820,055 A | 4/1989 | Muller |
| 4,828,392 A | 5/1989 | Nomura et al. |
| 4,848,911 A | 7/1989 | Uchida et al. |
| 4,855,253 A | 8/1989 | Weber |
| 4,929,083 A | 5/1990 | Brunner |
| 4,999,014 A | 3/1991 | Gold et al. |
| 5,017,514 A | 5/1991 | Nishimoto |
| 5,100,237 A | 3/1992 | Wittekoek et al. |
| 5,112,129 A | 5/1992 | Davidson et al. |
| 5,114,235 A | 5/1992 | Suda et al. |
| 5,148,214 A | 9/1992 | Ohta et al. |
| 5,156,982 A | 10/1992 | Nagoya |
| 5,166,752 A | 11/1992 | Spanier et al. |
| 5,172,190 A | 12/1992 | Kaiser |
| 5,182,455 A | 1/1993 | Muraki |
| 5,182,610 A | 1/1993 | Shibata |
| 5,189,494 A | 2/1993 | Muraki |
| 5,191,393 A | 3/1993 | Hignette et al. |
| 5,216,257 A | 6/1993 | Brueck et al. |
| 5,262,258 A | 11/1993 | Yanagisawa |
| 5,276,337 A | 1/1994 | Starikov |
| 5,296,917 A | 3/1994 | Kusonose et al. |
| 5,316,984 A | 5/1994 | Leourx |
| 5,327,221 A | 7/1994 | Saitoh et al. |
| 5,340,992 A | 8/1994 | Matsugu et al. |
| 5,343,292 A | 8/1994 | Brueck et al. |
| 5,355,306 A | 10/1994 | Waldo |
| 5,383,136 A | 1/1995 | Cresswell et al. |
| 5,388,909 A | 2/1995 | Johnson et al. |
| 5,414,514 A | 5/1995 | Smith et al. |
| 5,416,588 A | 5/1995 | Ducharme et al. |
| 5,436,097 A | 7/1995 | Norishima et al. |
| 5,438,413 A | 8/1995 | Mazor et al. |
| 5,465,148 A | 11/1995 | Matsumoto et al. |
| 5,477,057 A | 12/1995 | Angeley et al. |
| 5,479,270 A | 12/1995 | Taylor |
| 5,481,362 A | 1/1996 | Van Den Brink et al. |
| 5,498,501 A | 3/1996 | Shimoda et al. |
| 5,525,840 A | 6/1996 | Tominaga |
| 5,596,406 A | 1/1997 | Rosencwaig et al. |
| 5,596,413 A | 1/1997 | Stanton et al. |
| 5,608,526 A | 3/1997 | Piwonka-Corle et al. |
| 5,617,340 A | 4/1997 | Cresswell et al. |
| 5,627,083 A | 5/1997 | Tounai et al. |
| 5,665,495 A | 9/1997 | Hwang |
| 5,666,196 A | 9/1997 | Ishii et al. |
| 5,674,650 A | 10/1997 | Dirksen et al. |
| 5,699,282 A | 12/1997 | Allen et al. |
| 5,701,013 A | 12/1997 | Hsia et al. |
| 5,702,567 A | 12/1997 | Mitsui et al. |
| 5,703,685 A | 12/1997 | Senda et al. |
| 5,712,707 A | 1/1998 | Ausschnitt et al. |
| 5,757,507 A | 5/1998 | Ausschnitt et al. |
| 5,766,809 A | 6/1998 | Bae |
| 5,783,342 A | 7/1998 | Yamashita et al. |
| 5,801,390 A | 9/1998 | Shiraishi |
| 5,805,290 A | 9/1998 | Ausschnitt et al. |
| 5,808,742 A | 9/1998 | Everett et al. |
| 5,835,196 A | 11/1998 | Jackson |
| 5,857,258 A | 1/1999 | Penzes et al. |
| 5,872,042 A | 2/1999 | Hsu et al. |
| 5,877,036 A | 3/1999 | Kawai |
| 5,877,861 A | 3/1999 | Ausschnitt et al. |
| 5,883,710 A | 3/1999 | Nikoonahad et al. |
| 5,889,593 A | 3/1999 | Bareket |
| 5,902,703 A | 5/1999 | Leroux et al. |
| 5,909,333 A | 6/1999 | Best et al. |
| 5,912,983 A | 6/1999 | Hiratsuka |
| 5,923,041 A | 7/1999 | Cresswell et al. |
| 5,939,226 A | 8/1999 | Tomimatu |
| 5,949,145 A | 9/1999 | Komuro |
| 5,966,201 A | 10/1999 | Shiraishi et al. |
| 5,968,693 A | 10/1999 | Adams |
| 6,013,355 A | 1/2000 | Chen et al. |
| 6,020,966 A | 2/2000 | Ausschnitt et al. |
| 6,023,338 A | 2/2000 | Bareket |
| 6,037,671 A | 3/2000 | Kepler et al. |
| 6,046,094 A | 4/2000 | Jost et al. |
| 6,077,756 A | 6/2000 | Lin et al. |
| 6,079,256 A | 6/2000 | Bareket |
| 6,081,325 A | 6/2000 | Leslie et al. |
| 6,084,679 A | 7/2000 | Steffan et al. |
| 6,118,185 A | 9/2000 | Chen et al. |
| 6,128,089 A | 10/2000 | Ausschnitt et al. |
| 6,130,750 A | 10/2000 | Ausschnitt et al. |

(56) References Cited

U.S. PATENT DOCUMENTS

| | | |
|---|---|---|
| 6,137,578 A | 10/2000 | Ausschnitt |
| 6,140,217 A | 10/2000 | Jones et al. |
| 6,146,910 A | 11/2000 | Cresswell et al. |
| 6,153,886 A | 11/2000 | Hagiwara et al. |
| 6,160,622 A | 12/2000 | Dirksen et al. |
| 6,165,656 A | 12/2000 | Tomimatu |
| 6,177,330 B1 | 1/2001 | Yasuda |
| 6,197,679 B1 | 3/2001 | Hattori |
| 6,255,189 B1 | 7/2001 | Muller et al. |
| 6,278,957 B1 | 8/2001 | Yasuda et al. |
| 6,323,560 B1 | 11/2001 | Narimatsu et al. |
| 6,342,735 B1 | 1/2002 | Colelli et al. |
| 6,350,548 B1 | 2/2002 | Leidy et al. |
| 6,384,899 B1 | 5/2002 | den Boef |
| 6,385,772 B1 | 5/2002 | Courtney |
| 6,420,791 B1 | 7/2002 | Huang et al. |
| 6,420,971 B1 | 7/2002 | Leck et al. |
| 6,421,124 B1 | 7/2002 | Matsumoto et al. |
| 6,445,453 B1 | 9/2002 | Hill |
| 6,458,605 B1 | 10/2002 | Stirton |
| 6,462,818 B1 | 10/2002 | Bareket |
| 6,476,920 B1 | 11/2002 | Scheiner et al. |
| 6,486,954 B1 | 11/2002 | Mieher et al. |
| 6,522,406 B1 | 2/2003 | Rovira et al. |
| 6,580,505 B1 | 6/2003 | Bareket |
| 6,590,656 B2 | 7/2003 | Xu et al. |
| 6,611,330 B2 | 8/2003 | Lee et al. |
| 6,617,080 B1 | 9/2003 | Kawachi et al. |
| 6,633,831 B2 | 10/2003 | Nikoonahad et al. |
| 6,638,671 B2 | 10/2003 | Ausschnitt et al. |
| 6,650,424 B2 | 11/2003 | Brill et al. |
| 6,699,624 B2 | 3/2004 | Niu et al. |
| 6,713,753 B1 | 3/2004 | Rovira et al. |
| 6,767,680 B2 | 7/2004 | Schulz |
| 6,772,084 B2 | 8/2004 | Bischoff et al. |
| 6,813,034 B2 | 11/2004 | Rosencwaig et al. |
| 6,815,232 B2 | 11/2004 | Jones et al. |
| 6,819,426 B2 | 11/2004 | Sezginer et al. |
| 6,867,870 B1 | 3/2005 | Mihaylov et al. |
| 6,888,632 B2 | 5/2005 | Smith |
| 6,900,892 B2 | 5/2005 | Shchegrov et al. |
| 6,919,964 B2 | 7/2005 | Chu |
| 6,921,916 B2 | 7/2005 | Adel et al. |
| 6,937,337 B2 | 8/2005 | Ausschnitt et al. |
| 6,949,462 B1 | 9/2005 | Yang et al. |
| 6,982,793 B1 | 1/2006 | Yang et al. |
| 6,985,229 B2 | 1/2006 | Lee et al. |
| 6,985,618 B2 | 1/2006 | Adel et al. |
| 6,992,764 B1 | 1/2006 | Yang et al. |
| 7,042,569 B2 | 5/2006 | Sezginer et al. |
| 7,046,361 B1 | 5/2006 | Yang et al. |
| 7,046,376 B2 | 5/2006 | Sezginer |
| 7,061,615 B1 | 6/2006 | Lowe-Webb |
| 7,061,623 B2 | 6/2006 | Davidson |
| 7,061,627 B2 | 6/2006 | Opsal et al. |
| 7,065,737 B2 | 6/2006 | Phan et al. |
| 7,068,833 B1 | 6/2006 | Ghinovker et al. |
| 7,080,330 B1 | 7/2006 | Choo et al. |
| 7,112,813 B2 | 9/2006 | Den Boef et al. |
| 7,177,457 B2 | 2/2007 | Adel et al. |
| 7,181,057 B2 | 2/2007 | Adel et al. |
| 7,193,715 B2 | 3/2007 | Smedt et al. |
| 7,242,477 B2 | 7/2007 | Mieher et al. |
| 7,274,814 B2 | 9/2007 | Ghinovker et al. |
| 7,277,185 B2 | 10/2007 | Monshouwer et al. |
| 7,280,212 B2 | 10/2007 | Mieher et al. |
| 7,280,230 B2 | 10/2007 | Shchegrov et al. |
| 7,283,226 B2 | 10/2007 | Hasan |
| 7,289,213 B2 | 10/2007 | Mieher et al. |
| 7,298,481 B2 | 11/2007 | Mieher et al. |
| 7,301,634 B2 | 11/2007 | Mieher et al. |
| 7,317,531 B2 * | 1/2008 | Mieher ............ G01N 21/956 356/369 |
| 7,317,824 B2 | 1/2008 | Ghinovker et al. |
| 7,346,878 B1 | 3/2008 | Cohen et al. |
| 7,368,207 B2 * | 5/2008 | Rivers ............ G03F 7/70291 430/22 |
| 7,379,183 B2 | 5/2008 | Mieher et al. |
| 7,385,699 B2 | 6/2008 | Mieher et al. |
| 7,433,040 B2 | 10/2008 | Mieher et al. |
| 7,473,502 B1 | 1/2009 | Ausschnitt et al. |
| 7,474,401 B2 | 1/2009 | Ausschnitt et al. |
| 7,477,396 B2 | 1/2009 | Smith et al. |
| 7,486,408 B2 | 2/2009 | Van Der Schaar et al. |
| 7,700,247 B2 | 4/2010 | Ausschnitt et al. |
| RE45,245 E | 11/2014 | Ghinovker |
| 9,182,680 B2 | 11/2015 | Ghinovker |
| 2002/0054290 A1 | 5/2002 | Vurens et al. |
| 2002/0072001 A1 | 6/2002 | Brown et al. |
| 2002/0093648 A1 | 7/2002 | Nikoonahad et al. |
| 2002/0135875 A1 | 9/2002 | Niu et al. |
| 2002/0149782 A1 | 10/2002 | Raymond |
| 2002/0158193 A1 | 10/2002 | Sezginer et al. |
| 2002/0192577 A1 | 12/2002 | Fay et al. |
| 2003/0002043 A1 | 1/2003 | Abdulhalim et al. |
| 2003/0011786 A1 | 1/2003 | Levy et al. |
| 2003/0020184 A1 * | 1/2003 | Ballarin ............ G03F 7/70633 257/797 |
| 2003/0021465 A1 | 1/2003 | Adel et al. |
| 2003/0021466 A1 * | 1/2003 | Adel ............ G03F 7/70633 382/151 |
| 2003/0021467 A1 | 1/2003 | Adel et al. |
| 2003/0026471 A1 | 2/2003 | Adel et al. |
| 2003/0156276 A1 | 8/2003 | Bowes |
| 2003/0223630 A1 | 12/2003 | Adel et al. |
| 2004/0066517 A1 | 4/2004 | Huang et al. |
| 2004/0129900 A1 | 7/2004 | Den Boef et al. |
| 2004/0169861 A1 * | 9/2004 | Mieher ............ G01N 21/956 356/400 |
| 2004/0233440 A1 | 11/2004 | Mieher et al. |
| 2004/0233442 A1 | 11/2004 | Mieher et al. |
| 2004/0233443 A1 | 11/2004 | Mieher et al. |
| 2004/0233444 A1 | 11/2004 | Mieher et al. |
| 2005/0012928 A1 | 1/2005 | Sezginer et al. |
| 2005/0122516 A1 | 6/2005 | Sezginer et al. |
| 2005/0157297 A1 | 7/2005 | Abdulhalim et al. |
| 2005/0286051 A1 | 12/2005 | Sezginer et al. |
| 2006/0197950 A1 * | 9/2006 | Smith ............ G03F 7/70633 356/401 |
| 2008/0024766 A1 | 1/2008 | Mieher et al. |
| 2008/0049226 A1 | 2/2008 | Mieher et al. |
| 2008/0094630 A1 | 4/2008 | Mieher et al. |
| 2009/0153825 A1 * | 6/2009 | Edart ............ G03F 7/70633 355/67 |
| 2009/0224413 A1 | 9/2009 | Ghinovker |
| 2011/0292365 A1 * | 12/2011 | Cramer ............ G01N 21/4785 355/67 |
| 2016/0047744 A1 | 2/2016 | Adel |
| 2016/0274472 A1 * | 9/2016 | Mathijssen ......... G03F 7/70466 |

FOREIGN PATENT DOCUMENTS

| | | |
|---|---|---|
| JP | 60-126881 | 7/1986 |
| JP | 63-248804 | 10/1988 |
| JP | 8-116141 | 5/1996 |
| JP | 10-213896 | 8/1998 |
| JP | 11-86332 | 3/1999 |
| JP | 11-67631 | 9/1999 |
| JP | 11-307418 | 11/1999 |
| JP | 2001-093819 | 4/2001 |
| JP | 2001-267202 | 9/2001 |
| JP | 2004-508711 | 3/2004 |
| WO | 85/04266 | 9/1985 |
| WO | 95/02200 | 1/1995 |
| WO | 99/45340 | 9/1999 |
| WO | 99/56174 | 11/1999 |
| WO | 01/84382 | 11/2001 |
| WO | 01/97279 | 12/2001 |
| WO | 02/15238 | 2/2002 |
| WO | 02/18871 | 3/2002 |
| WO | 02-19415 | 3/2002 |
| WO | 02/25708 | 3/2002 |
| WO | 02/25723 | 3/2002 |

(56) References Cited

FOREIGN PATENT DOCUMENTS

| WO | 02/35300 | 5/2002 |
|---|---|---|
| WO | 02/50509 | 6/2002 |
| WO | 02/065545 | 8/2002 |
| WO | 02/069390 | 9/2002 |
| WO | 02/084213 | 10/2002 |
| WO | 03/001297 | 1/2003 |
| WO | 03/042629 | 5/2003 |
| WO | 03/054475 | 7/2003 |
| WO | 2004/053426 | 6/2004 |
| WO | 2004/076963 | 9/2004 |

OTHER PUBLICATIONS

Kim, Young-Chang et al., (Mar. 1999) "Automatic In-Situ Focus Monitor Using Line Shortening Effect," *Journal: Proceedings of the SPIE*, vol, 3677, pt. 1-2, pp. 184-193.

Sherman, Enrique R. "Characterization and Monitoring of Variable NA and Variable Coherence Capable Photo Steppers Utilizing the Phase Shift Focus Monitor Reticle," *Journal: Proceedings of the SPIE*, vol. 2439, pp. 61-69.

Bischoff, Jorg et al., "Modeling of Optical Scatterometry with Finite-Number-of-Periods Grating," *Journal: Proceedings of the SPIE*, vol. 3743, pp. 41-48.

Uchida, Norio et al., (1991) "A Mask to Wafer Alignment and Gap Setting Method for X-Ray Lithography Using Gratings," *Journal: Journal of Vacuum Science & Technology B*, vol. 9, No. 6, pp. 3202-3206.

Ina, Hidecki et al., (Dec. 1999) "Alignment Mark Optimization to Reduce Tool and Wafer-induced Shift for XTRA-1000," *Japanese Journal of Applied Physics*, vol. 38, No. 12B, pp. 7065-7070.

Baumbach, T. et al., "Grazing Incidence Diffraction by Laterally Patterned Semiconductor Nanostructures," *Journal: Journal of Physics*, vol. 32, No. 6, pp. 726-740.

TDB, (Dec. 1978) "Mask Overlay Determination," *IBM Technical Disclosure Bulletin*, pp. 2772-2773, www.delphion.com.

TDB, (Mar. 1990) "Phase-Sensitive Overlay Analysis Spectrometry," *IBM Technical Disclosure Bulletin*, pp. 170-174, www.delphion.com.

TDB, (Mar. 1990) "Interferometric Method of Checking the Overlay Accuracy in Photolitho Graphic Exposure Processes." *IBM Technical Disclosure Bulletin*, pp. 214-217. www.delphion.com.

TDB, (Feb. 1994) "Interferometric Measurement System for Overlay Measurement in Lithographic Processes", pp. 535-536.

Sang-Man Bae, et al., "Performance of New Overlay Measurement Mark," 424/*SPIE* vol. 2725.

V.I. Arkhipov, "Kinetics of the Diffraction Efficiency of Light-Induced Dynamic Gratings in Layers of Disordered Semiconductors", Moscow Engineering-Physics Institute Submitted Feb. 14, 1992; Quantum Electron Nov. 1993. 1994 American Institute of Physics.

Joseph C. Pellegrini, et al., (Mar. 1999) "Super Sparse Overlay Sampling Plans: An Evaluation of Methods and Algorithms for Optimizing Overlay Quality Control and Metrology Tool Throughput", *SPIE* vol. 3677-0277-786X.

V.C. Jaiprakash and C. J. Gould, (Mar. 1999) Comparison Optical, SEM, and AFM Overlay Measurement, *SPIE* vol. 3677-0277-786X.

Ya V. Fattakhov, (2000) "Formation of Periodic Diffraction Structures at Semiconductor Surfaces for Studying the Dynamics of Photoinduced Phase Transitions", 0030-400X/00/8901-0136.

D.G. Papazoglou, et al., (2000) "Photorefractive Optical Properties of Volume Phase Gratings Induced in Sillenite Crystals, When the Grating Vector Lies on the 111 plane," *Appl. Phys. B* 71. 841-848.

Kenneth W. Tobin, et al. "Automatic Classification of Spatial Signatures on Semiconductor Wafermaps," SEMATECH, Austin, Texas. *SPIE* vol. 3050.

Bharath Rangarajan, et al., Optimal Sampling Strategies for sub-100 nm Overlay, APD Lithography, Advanced Micro Devices Inc., Sunnyvale, CA, Department of Chemical Engineering, Michigan State University, East Lansing, MI, *SPIE* vol. 3332.

R.C. Herbert, (Apr. 1978) "Width and Overlay Narrow Kerf Test Site", IBM TDB, vol. 20 No. 11A. IBM Corp.

Auzino, L., (1998) "A New Technique for Multiple Overlay Check", Abstract. First Search: Detailed Record, Terms & Conditions 1992-2003, Copyright., *IEEE*.

Hsu et al., "Characterizing lens distortion to overlay accuracy by using fine measurement pattern", Mar. 1999, SPIE vol. 3677.

H.J. Levinson. et al., "Minimization of Total Overlay Errors on Product Wafers Using an Advanced Optimization Scheme" Abstract. First Search:Detailed Record. Terms & Conditions 1992-2003. Copyright 1998, *IEEE*.

Levinson, "Lithography Process Control", Tutorial Texts in Optical Engineering, vol. TT28, Chapter 5, pp. 96-107.

K. Kodate, et al. "Towards the Optimal Design of Binary Optical Elements with Different Phase Levels Using a Method of Phase Mismatch Correction," Abstract. FirstSearch: Detailed Record. Copyright 2001, *IEEE*.

Klienknecht, H.P., "Diffraction and Interference Optics for Monitoring Fine Dimensions in Device Manufacture", Copyright 1984 The Institute of Physics. Inst. Phys. Conf. Ser. No. 69. Paper presented at ESSDERC/SSSDT 1983, Canterbury Sep. 13-16, 1983.

Rivera et al., "Overlay Performance on Tungsten CMP Layers Using the ATHENA Alignment System".

Bishop, et al, "*The OMAG3 Reticle Set*," Jul. 31, 2003, International SEMATECH, Technology Transfer #3074417A-ENG, pp. 1-26.

Office Action dated Jul. 2, 2004 issued in U.S. Appl. No. 09/894,987.

Office Action dated Jun. 22, 2005 issued in U.S. Appl. No. 09/894,987.

Notice of Allowance dated Sep. 28, 2005 issued in U.S. Appl. No. 09/894,987.

Office Action dated Aug. 25, 2004 issued in U.S. Appl. No. 10/184,013.

Notice of Allowance dated Aug. 31, 2005 issued in U.S. Appl. No. 10/184,013.

Office Action dated Aug. 25, 2004 issued in U.S. Appl. No. 10/184,026.

Notice of Allowance dated Jan. 4, 2006 for U.S. Appl. No. 10/184,026.

Office Action dated Jun. 5, 2003 issued in U.S. Appl. No. 10/185,737.

Office Action dated Dec. 3, 2003 issued in U.S. Appl. No. 10/185,737.

Office Action dated Jun. 30, 2004 issued in U.S. Appl. No. 10/185,737.

Notice of Allowance dated Mar. 29, 2005 issued in U.S. Appl. No. 10/185,737.

Office Action dated Aug. 25, 2004 issued in U.S. Appl. No. 10/186,324.

Office Action dated Sep. 6, 2005 issued in U.S. Appl. No. 10/186,324.

Notice of Allowance dated Nov. 21, 2005 for U.S. Appl. No. 10/186,324.

US Office Action dated Sep. 26, 2006 issued in U.S. Appl. No. 10/729,838.

US Office Action dated May 18, 2007 issued in U.S. Appl. No. 10/729,838.

Notice of Allowance dated Aug. 23, 2007 issued in U.S. Appl. No. 10/729,838.

US Office Action dated Oct. 20, 2006 issued in U.S. Appl. No. 10/785,396.

US Office Action dated Mar. 2, 2007 issued in U.S. Appl. No. 10/785,396.

US Office Action dated Jun. 14, 2007 issued in U.S. Appl. No. 10/785,396.

US Office Action dated Oct. 30, 2007 issued in U.S. Appl. No. 10/785,396.

Notice of Allowance dated Mar. 17, 2008 issued in U.S. Appl. No. 10/785,396.

US Office Action dated Sep. 6, 2006 issued in U.S. Appl. No. 10/785,395.

US Office Action dated Mar. 8, 2007 issued in U.S. Appl. No. 10/785,395.

(56) References Cited

OTHER PUBLICATIONS

Notice of Allowance dated Jun. 5, 2007 issued in U.S. Appl. No. 10/785,395.
US Office Action dated Oct. 3, 2006 issued in U.S. Appl. No. 10/785,430.
Notice of Allowance dated Mar. 9, 2007 issued in U.S. Appl. No. 10/785,430.
US Office Action dated Aug. 9, 2006 issued in U.S. Appl. No. 10/785,723.
US Office Action dated Dec. 18, 2006 issued in U.S. Appl. No. 10/785,723.
Notice of Allowance dated Jun. 5, 2007 issued in U.S. Appl. No. 10/785,723.
US Office Action dated Oct. 20, 2006 issued in U.S. Appl. No. 10/785,821.
Final US Office Action dated Apr. 23, 2007 issued in U.S. Appl. No. 10/785,821.
Notice of Allowance dated Jul. 20, 2007 issued in U.S. Appl. No. 10/785,821.
US Office Action dated on Oct. 3, 2006 issued in U.S. Appl. No. 10/785,731.
Final US Office Action dated May 4, 2007 issued in U.S. Appl. No. 10/785,731.
US Office Action dated Aug. 8, 2007 issued in U.S. Appl. No. 10/785,731.
Notice of Allowance dated Dec. 31, 2007 issued in U.S. Appl. No. 10/785,731.
US Office Action dated Sep. 25, 2006 issued in U.S. Appl. No. 10/785,732.
US Office Action dated Mar. 9, 2007 issued in U.S. Appl. No. 10/785,732.
Notice of Allowance dated Jun. 26, 2007 issued in U.S. Appl. No. 10/785,732.
Office Action dated May 5, 2006 issued in U.S. Appl. No. 11/179,819.
Office Action dated Aug. 21, 2007 issued in U.S. Appl. No. 11/179,819.
Notice of Allowance dated Nov. 19, 2007 issued in U.S. Appl. No. 11/179,819.
Notice of Allowance dated Aug. 16, 2007 for issued in U.S. Appl. No. 11/394,938.
Notice of Allowance dated May 18, 2007 issued in. U.S. Appl. No. 11/432,947.
US Office Action dated Mar. 27, 2009 issued in U.S. Appl. No. 11/830,782.
US Office Action dated Apr. 2, 2010 issued in U.S. Appl. No. 11/830,782.
US Office Action dated Oct. 6, 2010 issued in U.S. Appl. No. 11/830,782.
US Office Action dated Dec. 14, 2009 issued in U.S. Appl. No. 11/830,782.
US Office Action dated Aug. 19, 2011 issued in U.S. Appl. No. 11/830,782.
US Office Action dated Mar. 2, 2012 issued in U.S. Appl. No. 11/830,782.
US Office Action dated Dec. 21, 2007 issued in U.S. Appl. No. 11/830,798.
Notice of Allowance dated Jun. 13, 2008 issued in U.S. Appl. No. 11/830,798.
US Office Action dated Jun. 11, 2008 issued in U.S. Appl. No. 11/926,603.
US Office Action dated Nov. 13, 2008 issued in U.S. Appl. No. 11/926,603.
US Office Action dated Jan. 6, 2009 issued in U.S. Appl. No. 11/926,603.
Notice of Allowance dated May 18, 2009 issued in U.S. Appl. No. 11/963,603.
US Office Action dated Oct. 17, 2008 issued in U.S. Appl. No. 11/963,730.
US Office Action dated Apr. 15, 2009 issued in U.S. Appl. No. 11/963,730.
Notice of Allowance dated Dec. 4, 2009 issued in U.S. Appl. No. 11/963,730.
US Office Action dated Apr. 9, 2008 issued in U.S. Appl. No. 11/227,764.
Notice of Allowance dated Dec. 15, 2008 issued in U.S. Appl. No. 11/227,764.
US Office Action dated Jul. 14, 2010 issued in U.S. Appl. No. 12/410,317.
US Office Action dated Jan. 4, 2011 issued in U.S. Appl. No. 12/410,317.
Notice of Allowance dated Nov. 9, 2011 issued in U.S. Appl. No. 12/410,317.
Corrected Notice of Allowance dated Dec. 30, 2011 issued in U.S. Appl. No. 12/410,317.
US Office Action dated Jun. 25, 2010 issued in U.S. Appl. No. 12/533,295.
US Office Action dated Oct. 7, 2010 issued in U.S. Appl. No. 12/533,295.
Notice of Allowance dated Nov. 19, 2010 issued in U.S. Appl. No. 12/533,295.
Written Opinion of the International Searching Authority dated Mar. 11, 2002 issued in PCT/US01/41932.
International Search Report dated Jan. 24, 2002 issued in PCT/US01/41932.
International Search Report dated May 26, 2004 issued in PCT/US03/38784.
European Supplemental Search Report dated Jul. 26, 2007 issued in 03 796 723.9.
European Office Action dated Dec. 13, 2007 issued in 03 796 723.9.
International Search Report dated Oct. 7, 2004 issued in PCT/US04/05419.
Written Opinion of the International Searching Authority dated Oct. 7, 2004 issued in PCT/US04/05419.
European Supplemental Search Report dated Jul. 26, 2007, issued in 04 713 795.5.
European Examination Report dated Dec. 13, 2007 issued in 04 713 795.5.
International Search Report dated Jan. 5, 2007 issued in PCT/US06/25836.
Written Opinion of the International Searching Authority dated Jan. 5, 2007 issued in PCT/US04/05419.
Notice of Reason for Refusal, Japanese Patent Application No. 2008-521428, dated May 31, 2011.
U.S. Appl. No. 13/407,124, Non Final Office Action mailed Apr. 1, 2014, 7 pgs.
U.S. Appl. No. 13/407,124, Non Final Office Action mailed Jun. 17, 2013, 4 pgs.
U.S. Appl. No. 13/407,124, Non Final Office Action mailed Dec. 16, 2014, 5 pgs.
U.S. Appl. No. 13/407,124, Notice of Allowance mailed Jan. 9, 2014, 5 pgs.
U.S. Appl. No. 13/407,124, Notice of Allowance mailed Apr. 1, 2015, 5 pgs.
U.S. Appl. No. 13/407,124, Notice of Allowance mailed Jul. 17, 2015, 5 pgs.
U.S. Appl. No. 13/407,124, Notice of Allowance mailed Sep. 4, 2014, 5 pgs.
U.S. Appl. No. 13/407,124, Restriction Requirement mailed Feb. 1, 2013, 6 pgs.
U.S. Appl. No. 13/875,160, Non Final Office Action mailed Apr. 9, 2014, 5 pgs.
U.S. Appl. No. 13/875,160, Notice of Allowance mailed Jul. 10, 2014, 8 pgs.
U.S. Appl. No. 14/873,120, Notice of Allowance mailed Jan. 25, 2016, 8 pgs.

\* cited by examiner

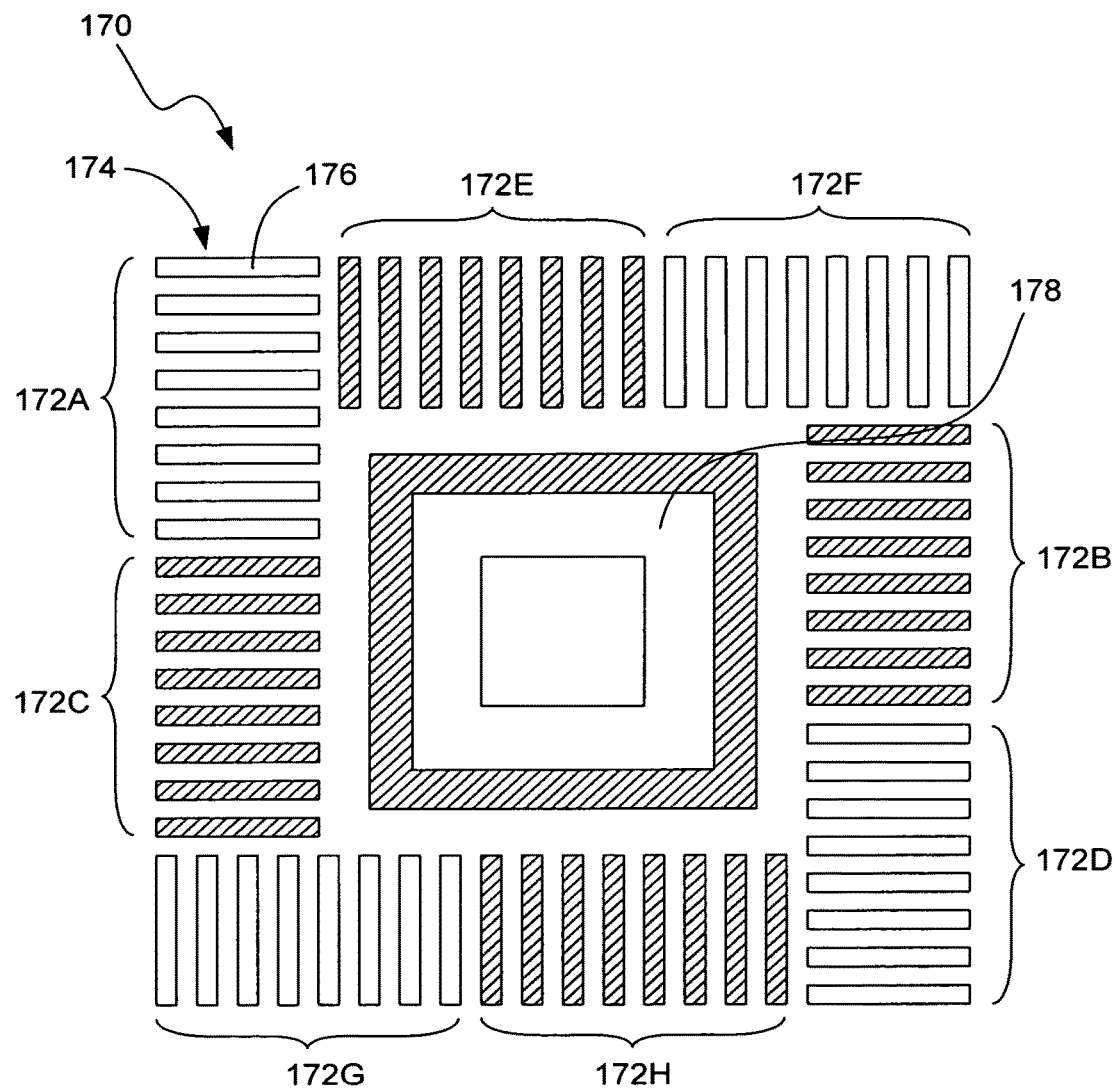
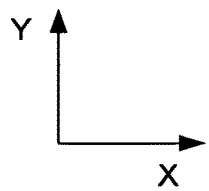
FIG. 11

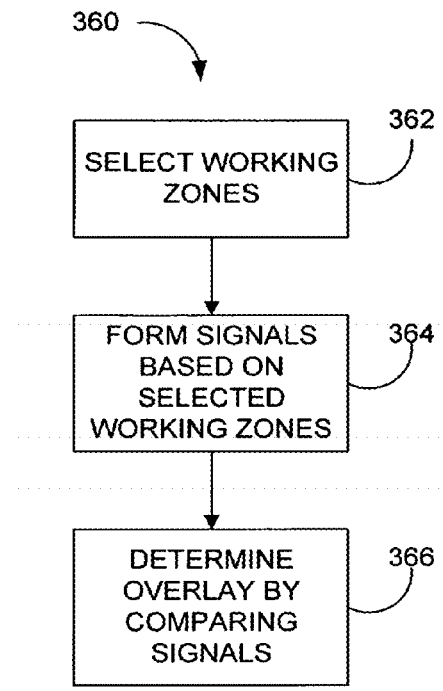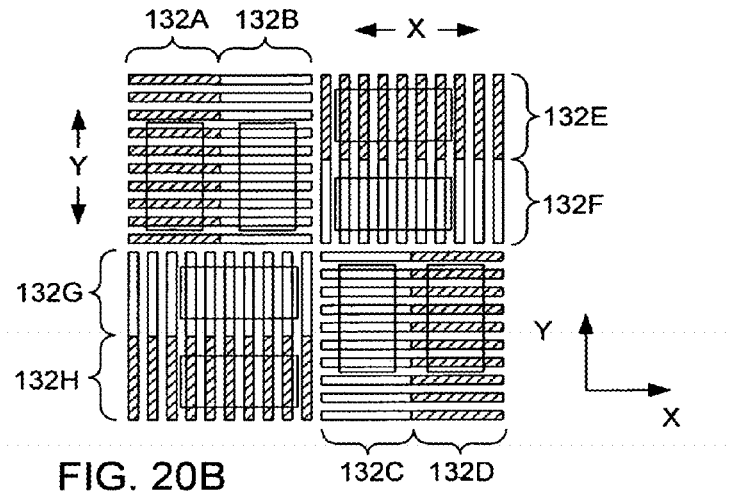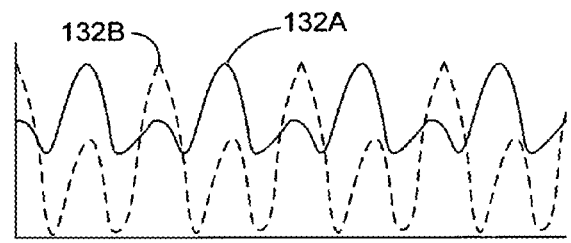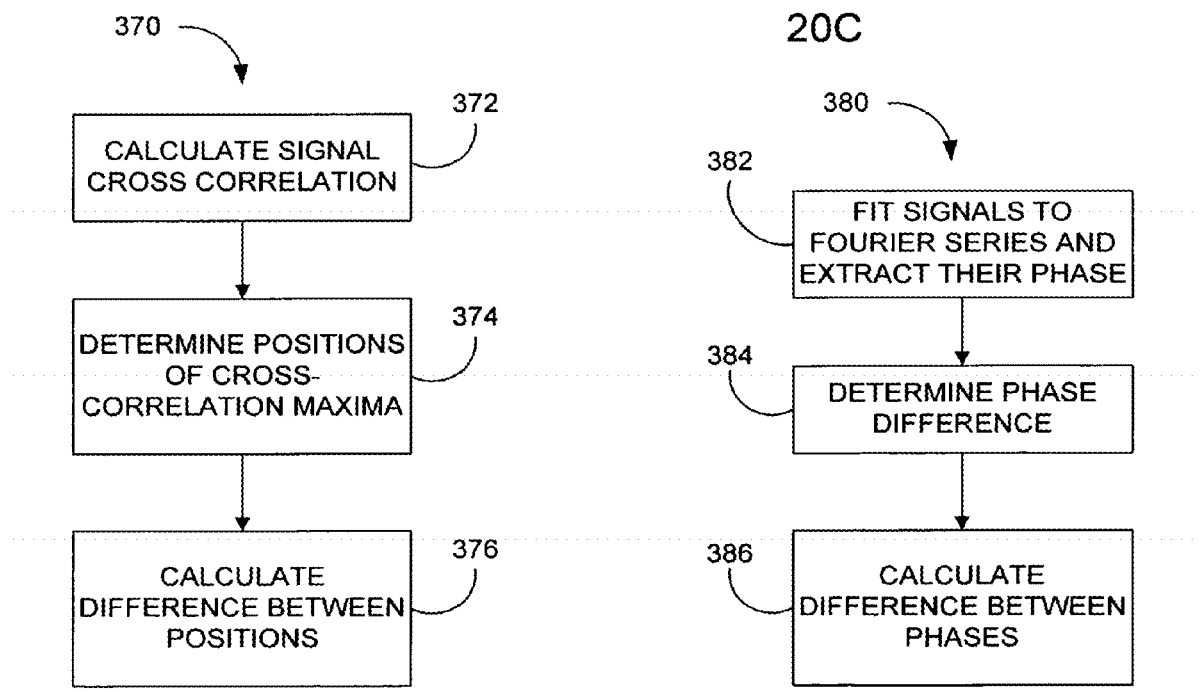

APPARATUS FOR MEASURING OVERLAY ERRORS

CROSS REFERENCE TO RELATED PATENT APPLICATION

This application claims priority to and is a Continuation application of co-pending U.S. patent application Ser. No. 14/873,120, filed 1 Oct. 2015, which claims priority and is a Continuation application of U.S. patent application Ser. No. 13/407,124, filed 28 Feb. 2012, now U.S. Pat. No. 9,182,680, issued 10 Nov. 2015, which claims priority to and is a Continuation application of application Ser. No. 12/410, 317, filed on Mar. 24, 2009, now U.S. Pat. No. 8,138,498, issued on Mar. 20, 2012, which application is a Divisional application of application Ser. No. 11/227,764, filed on Sep. 14, 2005, now U.S. Pat. No. 7,541,201, issued on Jun. 2, 2009, which application claims priority of (a) and is a Continuation-in-part application of application Ser. No. 09/894,987, filed on Jun. 27, 2001, now U.S. Pat. No. 7,068,833, issued on Jun. 27, 2006, which claims priority of Application No. 60/229,256, filed on Aug. 30, 2000, (b) U.S. Provisional Patent Application No. 60/698,535, filed on Jul. 11, 2005, (c) is a Continuation-in-part application of application Ser. No. 10/729,838, filed on Dec. 5, 2003, now U.S. Pat. No. 7,317,531, issued on Jan. 8, 2008, and (d) is a Continuation-In-Part application and claims priority of application Ser. No. 10/785,396, filed on 23 Feb. 2004, now U.S. Pat. No. 7,385,699, issued on 10 Jun. 2008, which is a continuation-in-part and claims priority of application Ser. No. 10/729,838, filed on 5 Dec. 2003, now U.S. Pat. No. 7,317,531, issued on 8 Jan. 2008, which application claims priority of (i) Application No. 60/440,970, filed Jan. 17, 2003, (ii) Application No. 60/449,496, filed Feb. 22, 2003, (iii) Application No. 60/431,314, filed Dec. 5, 2002, (iv) Application No. 60/504,093, filed Sep. 19, 2003, and (v) Application No. 60/498,524, filed 27 Aug. 2003. The applications and patents listed above are incorporated herein by reference in their entirety for all purposes

BACKGROUND OF THE INVENTION

The present invention relates generally to overlay measurement techniques, which are used in semiconductor manufacturing processes. More specifically, the present invention relates to overlay marks for measuring alignment error between different layers or different patterns on the same layer of a semiconductor wafer stack.

The measurement of overlay error between successive patterned layers on a wafer is one of the most critical process control techniques used in the manufacturing of integrated circuits and devices. Overlay accuracy generally pertains to the determination of how accurately a first patterned layer aligns with respect to a second patterned layer disposed above or below it and to the determination of how accurately a first pattern aligns with respect to a second pattern disposed on the same layer. Presently, overlay measurements are performed via test patterns that are printed together with layers of the wafer. The images of these test patterns are captured via an imaging tool and an analysis algorithm is used to calculate the relative displacement of the patterns from the captured images.

The most commonly used overlay target pattern is the "Box-in-Box" target, which includes a pair of concentric squares (or boxes) that are formed on successive layers of the wafer. The overlay error is generally determined by comparing the position of one square relative to another square.

To facilitate discussion, FIG. 1A is a top view of a typical "Box-in-Box" target 10. As shown, the target 10 includes an inner box 12 disposed within an open-centered outer box 14. The inner box 12 is printed on the top layer of the wafer while the outer box 14 is printed on the layer directly below the top layer of the wafer. As is generally well known, the overlay error between the two boxes, along the x-axis for example, is determined by calculating the locations of the edges of lines c1 and c2 of the outer box 14, and the edge locations of the lines c3 and c4 of the inner box 12, and then comparing the average separation between lines c1 and c3 with the average separation between lines c2 and c4. Half of the difference between the average separations c1&c3 and c2&c4 is the overlay error (along the x-axis). Thus, if the average spacing between lines c1 and c3 is the same as the average spacing between lines c2 and c4, the corresponding overlay error tends to be zero. Although not described, the overlay error between the two boxes along the y-axis may also be determined using the above technique.

There was also the introduction of the "Box in Bar" target and the "Bar in Bar" target, both of which had the same general appearance as the "Box in Box" target. In "Box in Bar" targets, the outer box of the "Box in Box" target is separated into a plurality of parallel bars (see FIG. 1B). In "Bar in Bar" overlay marks, both the outer and inner box of the "Box in Box" target are separated into a plurality of parallel bars. A further example of this type of modified target is taught by Chen et. al in U.S. Pat. No. 6,118,185.

Recently, there was the introduction of separated bars that created features comparable to the design rules of the device itself. By way of example, Ausschnitt et al., in U.S. Pat. No. 6,130,750, discloses "Box-in Box" type targets having separated bars.

Although such designs have worked well, there are continuing efforts to provide targets with improved functionality. For example, it would be desirable to have targets capable of improving the correlation between the overlay error measured on the test pattern and the real overlay error of the circuit components.

SUMMARY OF THE INVENTION

The invention relates to an overlay mark for determining the relative shift between two or more successive layers of a substrate, and a metrology system for measuring such mark. The overlay mark includes at least one test pattern for determining the relative shift between a first and a second layer of the substrate in a first direction. The test pattern includes a first set of working zones and a second set of working zones. The first set of working zones are disposed on a first layer of the substrate and have at least two working zones diagonally opposed and spatially offset relative to one another. The second set of working zones are disposed on a second layer of the substrate and have at least two working zones diagonally opposed and spatially offset relative to one another. The first set of working zones are generally angled relative to the second set of working zones thus forming an "X" shaped test pattern.

The invention relates, in another embodiment, to an overlay mark for determining the relative shift between two or more successive layers of a substrate via an imaging device configured for capturing an image of the overlay mark. The overlay mark includes a first set of working zones disposed on a first layer of the substrate. The first set of working zones includes at least two working zones diagonally opposed to one another and positioned within the perimeter of the mark. Each of the working zones includes a periodic structure of coarsely segmented elements positioned therein. The coarsely segmented elements are generally oriented in a first direction. The overlay mark further includes a second set of working zones positioned crosswise relative to the first working group. The second working group is disposed on a second layer of the substrate and has at least two working zones diagonally opposed to one another and positioned within the perimeter of the mark. Each of the working zones has a periodic structure of coarsely segmented elements positioned therein. The coarsely segmented elements are generally oriented in the first direction.

The invention relates, in another embodiment, to an overlay mark for determining the relative shift between two or more separately generated patterns on a single layer of a substrate. The overlay target includes a test region positioned on a first layer of the substrate. The first layer is typically formed by a first pattern via a first process and a second pattern via a second process. The overlay target further includes a plurality of working zones positioned in the test region. The working zones representing the actual areas of the test region that are used to determine the relative shift between the first and second patterns. A first portion of the working zones are formed via the first process and a second portion of the working zones are formed via the second process. The overlay target additionally includes a periodic structure positioned within each of the working zones. Each of the periodic structures includes a plurality of coarsely segmented elements. Each of the coarsely segmented elements are formed by a plurality of finely segmented elements.

The invention relates, in another embodiment, to a method for determining the relative shift between two or more successive layers of a substrate or between two or more separately generated patterns on a single layer of a substrate. The method includes capturing an image of an overlay mark formed on the substrate. The overlay mark having a plurality of working zones. Each of the working zones including a periodic structure of coarsely segmented elements. The method further includes selecting a plurality of working zones from the captured image, wherein at least one working zone from each layer or pattern is selected. The method additionally includes forming representative signals for each of the selected working zones, wherein at least one signal for each layer or pattern is formed. The method also includes comparing the signal from the first layer or pattern to the signal from a second layer or pattern to determine the relative shift between different layers or patterns.

BRIEF DESCRIPTION OF THE DRAWINGS

The present invention is illustrated by way of example, and not by way of limitation.

FIG. 11 is a top plan view of an overlay mark, in accordance with an alternate embodiment of the present invention.

FIG. 20A is a simplified flow diagram illustrating a method of calculating overlay, in accordance with one embodiment of the present invention.

FIG. 20B is a top plan view of the overlay mark of FIG. 9, in accordance with one embodiment of the present invention.

FIG. 20C illustrates a pair of collapsed 1D signals, in accordance with one embodiment of the present invention.

FIG. 21 is a flow diagram illustrating a method 370 of calculating overlay using Covariance, in accordance with one embodiment of the present invention.

FIG. 22 is a flow diagram illustrating a method 380 of calculating overlay using Fourier Decomposition, in accordance with one embodiment of the present invention.

DETAILED DESCRIPTION OF SPECIFIC EMBODIMENTS

Figure 1A:
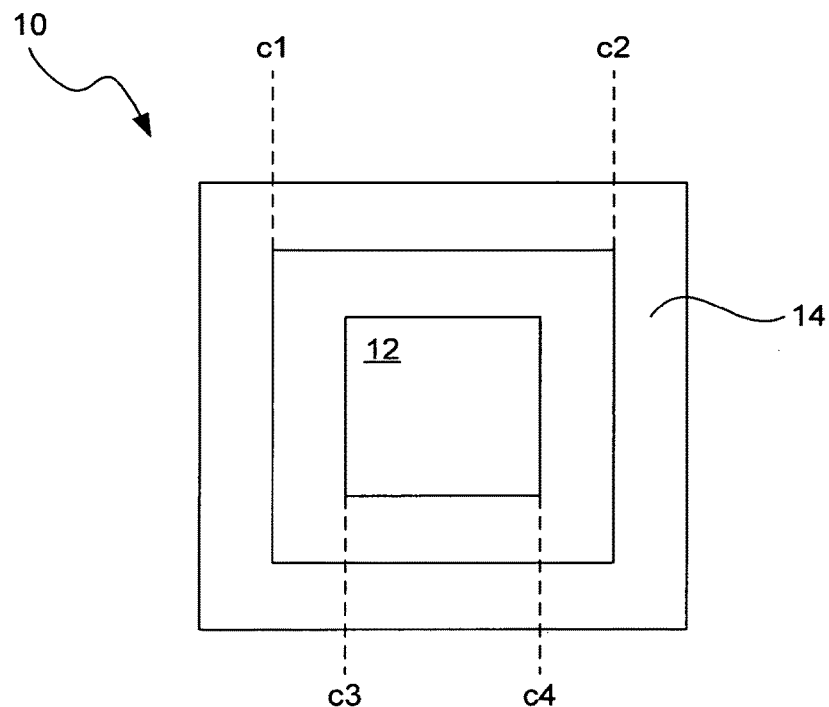
FIGS. 1A&B are top plan views of overlay marks, which are well known in the art.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order not to unnecessarily obscure the present invention.

The present invention, in each of the various embodiments, uses overlay marks that are composed of periodic structures formed on each of two layers of a semiconductor wafer to provide overlay information between those two layers of the semiconductor device. The overlay marks are formed in specific locations on each wafer layer such that the periodic structures on one layer will be aligned with the periodic structures on the other layer when the two layers are properly aligned. Conversely, the periodic structures on each layer will be offset from each other when the two layers are not properly aligned. Alternatively, the present invention may use overlay marks that are composed of periodic structures formed on a single layer by two or more separate processes to provide alignment information between two different patterns on the same layer. Each of the periodic structures is composed of a plurality of structures, which increases the amount of information that may be used to measure overlay, and which may be widely modified to diminish the impact of certain processes on the overlay measurements. Each of these structures is composed of sub-structures that are about the same size and pitch (e.g., separation) as structures of the actual integrated circuits. By forming each of the periodic structures with sub-structures that are sized closer to the size of the actual circuits, a more accurate measurement of any alignment error in such circuits is obtained. The invention is particularly suitable for overlay measurement techniques that require capturing an image of the overlay mark.

The periodic structures and sub-structures described herein are generally patterned using suitable photolithographic techniques, and the lithographic patterns are subsequently transferred to other materials and layers using established processing techniques such as etching and deposition. In the simplest application, the transferred patterns constitute etched or deposited lines or vias. For example, the periodic structures and sub-structures may be formations of photoresist material, recessed cavity formations, embedded trenches and/or other structures within a wafer layer. The structures and sub-structures formed by cavities may be cavities formed in any of the layers during the semiconductor fabrication process. For example, the cavities may be formed in the photoresist layer, the dielectric material layer, or the metal layers. It should be noted that the above processes are not a limitation and that any suitable fabrication technique may be used.

Embodiments of the invention are discussed below with reference to FIGS. 1-23. However, those skilled in the art will readily appreciate that the detailed description given herein with respect to these figures is for explanatory purposes as the invention extends beyond these limited embodiments.

Figure 2:
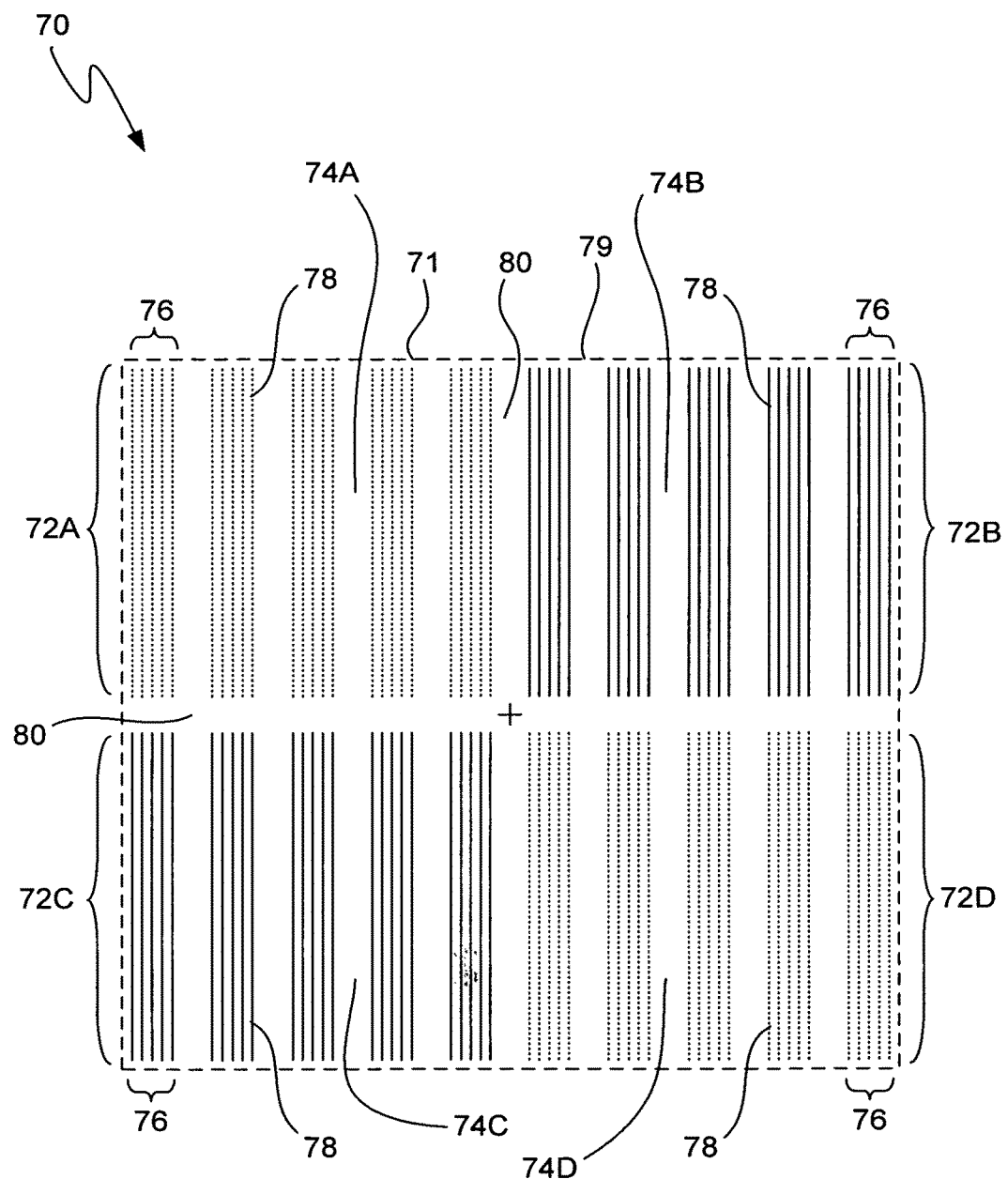
FIG. 2 is a top plan view of an overlay mark, in accordance with one embodiment of the present invention.

FIG. 2 is a top plan view of an overlay mark 70, in accordance with one embodiment of the present invention. The mark 70 is suitable for image based overlay measurement techniques. For ease of discussion, overlay mark 70 is shown in a configuration that results when the tested layers of a wafer are in proper alignment. The overlay mark 70 is generally provided to determine the relative shift between two or more successive layers of a substrate or between two or more separately generated patterns on a single layer of a substrate. By way of example, the overlay mark may be used to determine how accurately a first layer aligns with respect to a second layer disposed above or below it or how accurately a first pattern aligns relative to a preceding or succeeding second pattern disposed on the same layer. For ease of discussion, the overlay mark shown in FIG. 2 will be described in context of measuring overlay between different layers of a wafer. It should be noted, however, that the overlay marks in this figure (and any subsequent figures) may also be used to measure two or more separately generated patterns on a single layer of a wafer. In general, any convenient orientation of the mark relative to the placement of the dies on the wafer can be chosen so long as the orientation of the successive marks is the same from layer to layer or from pattern to pattern.

The overlay mark 70 is defined by a perimeter 71. The perimeter 71 is typically based on metrology tool limitations and circuit design rules. For instance, the upper limits of the perimeter may be set by the field of view (FOV) of the metrology tool used to measure overlay and/or the scribe line budget. The FOV generally refers to the optical perimeter that defines the area available for capturing an image via the metrology tool. The mark is typically positioned inside the scribe line of the wafer. i.e., the scribe line is the place on the wafer where the wafer is separated into dies via sawing or dicing and thus the circuit itself is not patterned there. The scribe line budget, therefore, generally refers to the available space allowed by the scribe line for the placement of the mark. In addition, the lower limits of the perimeter may be set by the minimum area needed by the metrology tool to image the mark (e.g., obtain adequate signal or measurement quality).

It is generally believed that the perimeter 71 should be as large as possible so as to maximize the amount of information used for overlay measurements. The size and shape of the perimeter 71 may be widely varied. For example, the perimeter may form shapes such as squares circles, triangles, rectangles, polygons and the like. The size of the perimeter, in any given direction, is generally between about 10 and about 100 microns, and more particularly between about 20 and about 50 microns. In the illustrated embodiment, the perimeter 71 directly corresponds to the size and shape of the FOV 79 of the metrology tool, i.e., the FOV defines the perimeter. In most cases, the FOV is rectangular shaped due to CCD proportions. It should be noted, however, that this is not a limitation and that the FOV may be substantially larger than the mark's perimeter 71. For example, the mark's perimeter may be limited by the area on the scribe line.

The overlay mark 70 further includes a plurality of working zones 72, which are configured to divide and substantially fill the perimeter 71 of the mark 70 (from center to edge). For example, the working zones may be configured to fill the perimeter of the mark such that the combined area of the working zones is substantially equal to the total area of the mark. The working zones 72 represent the actual areas of the mark that are used to calculate alignment between different layers of the wafer. As such, the working zones 72 typically include information relating to the two layers for which overlay measurements are made. For example, some of the working zones are positioned in one layer of the wafer (represented by solid lines) while some of the working zones are positioned in a different layer of the wafer (represented by dashed lines).

In most cases, the working zones 72 are spatially separated from one another so that they do not overlap portions of an adjacent working zone (i.e., each of the working zones represents a different area of the mark). This is typically done to ensure that each of the working zones is properly imaged by the metrology tool. Although not always necessary, the working zones 72 may be spatially separated by an exclusion zone 80 so that each of the working zones is distinct. Exclusion zones 80 are areas of the target image where either a physical target structure or a corresponding optical signal is distorted and therefore it is excluded from the overlay calculation. The size of the exclusion zones is typically balanced with the size of the working zones so as to provide as much information as possible for the measurement of overlay. That is, it is generally desired to have larger working zones and smaller exclusion zones. In some cases, it may be desirable to have a small amount of overlap between adjacent working zones so as to allow SEM cross sectioning to verify the accuracy of the overlay measurements.

In one embodiment, the geometry, including size, shape and distribution of the working zones is configured to balance out or compensate for non-uniform or asymmetrical characteristics that may occur across the mark. Asymmetries may arise from the optical aberration and illumination asymmetry in the metrology tool (tool induced shifts), as well as process induced structural features (wafer induced shifts).

Tool induced shift (TIS) generally refers to how much the apparent position of the mark moves or shifts as a result of metrology tool problems such as non-uniform illuminations and/or optical aberrations. Illumination generally pertains to how the light is distributed to the target. Aberrations generally pertain to how the light is focused and collected. Non-uniform illuminations may be caused by a defect or misalignment in one of the optical components associated with transferring the light from the light source to the wafer. Non-uniform optical aberrations may be caused by a defect or misalignment in the objective lens of the optical system. By way of example, aberrations may include spherical aberrations, astigmatism aberrations and coma aberrations. Coma aberrations may have a greater impact on TIS as a result of its asymmetrical nature across the FOV of the metrology tool, Wafer induced shift (WIS) generally refers to how much the apparent position of the mark moves as a result of process variations such as distortions caused by chemical mechanical polishing (CMP) and sputter deposition.

Non-uniformities, asymmetries and variations may also arise from difference between the height of the different line sets from each layer. The lower layer lines are sometimes visible only through the intermediate layer of the wafer since the intermediate layer material covers the lines on the lower layer. On the other hand, the upper lines are generally formed from the photoresist applied on the top of the lower layer.

Accordingly, by adjusting the size, shape and distribution of the overlay information from the two layers or patterns within the field of view of the overlay metrology tool, it is possible to diminish the impact of lithography and/or process non-uniformities, asymmetries and variations. In some cases, it may even be possible to enhance the overlay measurement. Resist patterns are less inclined to process variation and thus they may potentially be more useful for acquisition areas of the mark.

In one implementation, balancing is accomplished by selectively positioning the working zones of the same layer at different positions around the perimeter of the mark. For example, the working zones may be positioned at different positions within the FOV in order to get the best possible balance between aberrations and illumination and process results that vary across the FOV. In the illustrated embodiment (FIG. 2), working zones of the same layer are positioned opposite one another so as to balance out asymmetries that may occur from the left to the right or from the top to the bottom or from the inner to the outer regions of the FOV (or vice versa). In one implementation, the optimal distribution for balancing out asymmetries is determined by performing optical simulations of tool induced shift (e.g., how much the apparent position of the mark moves as a result of tool problems such as illumination and/or aberrations). In another implementation, the optimal distribution for balancing out asymmetries is determined by performing experiments (e.g., run a sample of wafers). In addition, within the FOV there might be parts of the mark, which have unacceptable aberrations and illuminations and/or process damage, and therefore, the working zones may be positioned at specific positions inside the FOV to avoid these areas.

As mentioned, each of the working zones is configured to represent one of the two successive layers of the overlay mark. In one embodiment, the working zones represent an equal number of first layers or patterns and second layers or patterns, i.e., for each working zone in the first layer there is a corresponding working zone in the second layer. This is typically done to balance variations, non-uniformities and/or asymmetries that may exist in the layers and/or the metrology tool. As such, the number of working zones is generally based on a factor of 2, as for example, 2, 4, 8, 16 and the like. It is generally believed that by distributing the regions to more points within the field of view, the more likely they are to balance out the non-uniformities caused by illuminations, aberrations and the process. By way of example, the size of the working zones (e.g., square) is generally between about 2 to about 24 microns, and more particularly between about 4 to about 15 microns. In most cases, the size of the working zones is inversely proportional to the number of working zones, i.e., as the number increases, the size decreases. By way of example, the size of the working zones is generally between about 10 and about 24 microns for four working zones, between about 5 and about 12 microns for eight working zones, and between about 2.5 and about 6 microns for sixteen working zones.

In addition, there may be cases that require an uneven number of first and second layered working zones, i.e., 4 first layered working zones and 2 second layered working zones. There may also be the case that requires an uneven number of total working zones. i.e., 2 first layered working zones and 1 second layered working zones. There may also be the case that requires unequal working zone sizes. For example, a first group of working zones may have a first size while a second group of working zones may have a second size where the second size is either smaller or larger than the first size.

Although the working zones are generally constrained by the FOV (e.g., perimeter of the mark), the shape of the working zones may vary according to the specific needs of each mark. By way of example, the zones may have a square shape (as shown), an L shape, a rectangular shape, a triangular shape, a circular shape, a polygonal shape and the like. In most cases, the shape and size of the working zones are identical. This is typically done to balance variations, non-uniformities and/or asymmetries that may exist in the layers and/or the metrology tool. However, it should be noted, that this is not a limitation and that some or all of the working zones may have different shapes. For example, some of the working zones may have a rectangular shape while other working zones may have a square shape.

Furthermore, working zones representing different layers are typically juxtaposed relative to one another. By way of example, the mark may include at least two juxtaposed working zones: a right region representing a first layer and a left region representing a second layer. In addition, the mark may include a top working zone representing a first layer and a bottom working zone representing a second layer. In some implementations, the juxtaposed regions are positioned equidistant from the center of the target (e.g., center of FOV). It should be noted, however, that juxtaposition is not a limitation and that the position of the working zones may vary according to the specific needs of each mark. For example, there may be cases that require working zones representing first layers to be juxtaposed relative to other working zones representing first layers (or vice versa).

Referring to FIG. 2, working zones 72A and 72D (represented by dashed lines) are formed in one layer of the wafer while working zones 72B and 72C are formed in a different layer of the wafer (represented by solid lines). As shown, working zones 72A&D are angled relative to working zones 72B&C. That is, working zones 72A&D lie crosswise relative working zones 72B&C. Furthermore working zones 72A and 72D, which are disposed on the same first layer, are positioned opposite one another at a first vertical angle while working zones 72B and 72C, which are disposed on the same second layer, are positioned opposite one another at a second vertical angle. That is, working zone 72A is diagonally opposed to working zone 72D, and working zone 72B is diagonally opposed to working zone 72C. Moreover, working zone 72A is spatially offset from working zone 72D, and working zone 72B is spatially offset from working zone 72D. For example, the center of working zone 72D is positioned below and to the right of the center of working zone 72A, and the center of working zone 72C is positioned below and to the left of the center of working zone 72B. As should be appreciated, these cross-positioned structures form an "X" shaped pattern.

It should be noted that this particular "X" configuration is shown by way of example and not by way of limitation, i.e., the size, shape and distribution of the working zones and their periodic structures may vary according to the specific needs of each mark. For example, the working zones may be configured to fill a variety of different sized and different shaped FOVs. It is generally desirable to fill the field of view with as much information as possible for reasons of process robustness and information optimization. The working zones may also be configured to take on other shapes such as rectangles, triangles, parallelograms, trapezoids, regular polygons, circles and the like. Furthermore, the opposing periodic structures may be disposed on other layers. For example, working zones 72B and 72C may be disposed on the first layer (dashed lines) and working zones 72A and 72D may be disposed on the second layer (solid lines). Further still, the working zones may only partially fill the field of view. Moreover, the exclusion zones may be eliminated so that the working zones may be positioned next to one another along their edges (e.g., completely filling the regions and thus the FOV) or partially over one another so as to allow for line ends to overlap for cross section accuracy.

Each of the working zones 72 contains an individual periodic structure 74, as for example, periodic structures 74A-D. As shown, each of the periodic structures 74 substantially fills the perimeter of its corresponding working zone 72. Moreover, each of the periodic structures 74 includes a plurality of coarsely segmented lines 76 that increase the amount of information that may be used for overlay measurements. In addition, by constructing marks from periodic structures, it is possible to implement a broader range of overlay measurement algorithms that maximize the benefits of higher information density in the mark. Each of the coarsely segmented lines 76 is formed by a number of sub-structures or finely segmented elements 78.

Even though some of the finely segmented elements 78 may be represented by dashed lines, the finely segmented elements 78 within each periodic structure are not necessarily discontinuous linear formations that are segmented at regular intervals. The dashed lines may represent continuous linear formations within each of the periodic structures. However, in alternative embodiments, it is possible that the finely segmented elements 78 within each periodic structure may take on various shapes and sizes, which include discontinuous linear formations that are segmented at regular intervals. These will be described in greater detail below.

In one embodiment, the geometry, i.e., linewidth and spacing, of the periodic structure is configured to find the proper balance between the image resolution of the metrology tool and the robustness of the process. For instance, in most cases, it is desirable to have a large geometry (e.g., large linewidths and spacings) so that the periodic structure may be optically resolved by the tool, and a small geometry (e.g., small linewidths and spacings) so that the process effects on the mark are minimized. With regards to image resolution, there is a minimum size requirement that each metrology tool has for resolving the coarsely segmented lines. Furthermore, it is generally known that as the period of the periodic structure gets smaller, the metrology tool resolution diminishes, i.e., there is a point where the resolution of the metrology tool ceases to work effectively. With regards to process robustness, each time a new process is introduced in semiconductor manufacture, there is some impact on the overlay mark. The ability to measure the target depends on it's visibility or contrast in the image tool. Some processes such as metallization tend to diminish contrast, hence impacting precision. Other processes such as chemical mechanical polishing (CMP) tend to blur or distort the mark, hence impacting accuracy. These processes may also make the structures asymmetric or create an apparent, optically measured spatial translation of the center of the structures relative to the center of the originally patterned trench or line (e.g., circuit pattern).

For specific processes, such as aluminum coated, chemically mechanically polished tungsten, it is advantageous for the characteristic dimensions of these structures to be approximately 1 to 2 microns or less in order to diminish the impact of asymmetries resultant from the polishing and aluminum deposition processes. However, if the width of the trench is too small, the remaining topography at the top of the aluminum layer is too small to provide optically adequate contrast and, thus, the mark does not provide adequate overlay information. On the other hand, the lower bound for characteristic dimensions of structures at this scale is determined by the resolution limit of the metrology tool. For example for an overlay tool with a numerical aperture (NA) of 0.9 and a mean illumination wavelength of 550 nm gives a Rayleigh resolution limit or criteria of approximately 0.4 microns. In this particular case, it may be preferable to maintain the linewidth above 0.5 microns in order not to diminish contrast and hence signal to noise, and below 1-2 micron in order to diminish the impact of asymmetries resultant from the polishing and aluminum deposition processes. It should be noted, however, that this is by way of example and not by way of limitation and that it may be possible to achieve better than the Rayleigh resolution limit.

In one embodiment, the geometry of the periodic structure is determined by experimentation. For example, several wafers may be run through a process to find a period for which the TIS variability is the smallest, i.e., measure the tool induced shift variability at multiple sites on the wafer and then select the pitch that minimizes the TIS variability and process variability.

In one embodiment, the period and phase of the periodic structure is configured to filter out high frequency edges.

In the illustrated embodiment, each of the periodic structures 74A-D has the same pitch and duty cycle. That is, each of the periodic structures 74 consist of an equal number of coarsely segmented lines 76, which are parallel and which have equal linewidths and equal spacings there between. The dimensions of the pitch, linewidths and spacings may be widely varied. By way of example, the dimension of the pitch may be between about 1 to about 3 microns, and the dimensions of the linewidths and spacings may be between about 0.3 to about 2 microns, and more particularly between about 0.5 to about 1 microns.

It should be noted that equal pitch, linewidths and spacings for each of the periodic structures is not a limitation and that they may vary according to the specific needs of each mark. For example, each of the periodic structures may have a different pitch or duty cycle. Alternatively, some of periodic structures may have the same pitch or duty cycle, while other periodic structures may have a different pitch or duty cycle. Furthermore, the periodic structures may have a pitch that varies across the periodic structure. By way of example, the periodic structure may be a chirped periodic structure (e.g., smaller to larger). As was explained previously, the pitch, linewidths and spacings are generally optimized according to process robustness requirements and contrast requirements of the metrology tool.

The number of lines inside each periodic structure may be varied to meet the specific needs of each mark. It is generally believed that the number of lines is dependent on the resolution required and the signal to noise ratio desired. Most imaging tools have a resolution limit between about 0.3 and about 0.9. The number of lines may also be determined by process requirements such as chemical mechanical polishing distortions that affect the outermost line segments more than the inner line segments of a group. One factor affecting the maximum number of lines that may be used within a group of line segments is the metrology tool resolution. From the perspective of the minimum number of lines that is needed for operation, that number is two. In the embodiment shown, each of the periodic structures 74A-D includes 5 coarsely segmented lines. In some cases, it may even be desirable to have periodic structures having a different number of lines, i.e., a first periodic structure having 5 lines and a second periodic structure having 2 lines.

Figure 1B:
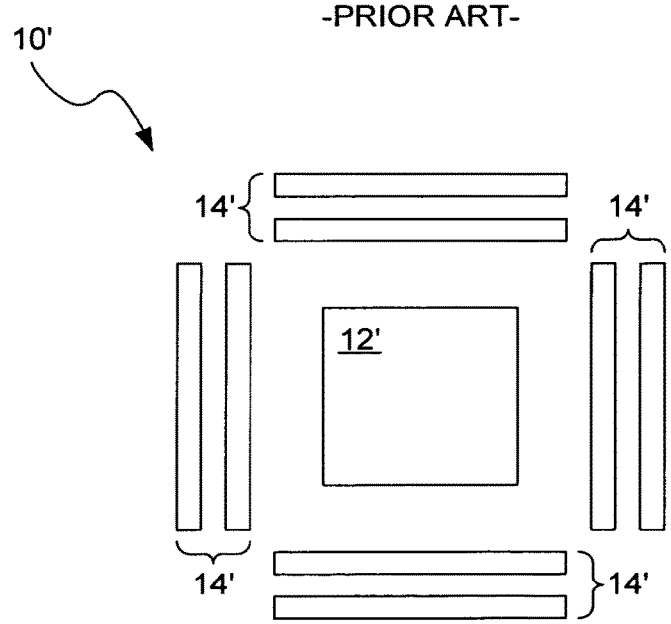

In the embodiment shown, the lines of the periodic structures 74A-D are parallel to one another so as to provide position information in a single direction. As should be appreciated, the lines in FIG. 1 are configured for X-axis measurements since the lines are non-parallel (e.g., perpendicular or orthogonal) to the axis of measurement. Given this configuration, any offset between the two successive layers in the X-direction will be present between the first set of periodic structures 74 A&D and the second set of periodic structures 74 B&C. As such, the alignment between the two layers of the wafer in the X-direction may be determined by comparing the relative positions of the two groups of periodic structures. For instance, the positions of periodic structures 74 A and D, which are disposed on the first layer, may be compared with the positions (e.g., centers of symmetry) of periodic structures 74 B and C, which are disposed on the second layer, to determine the alignment between consecutive layers in the X direction.

In one embodiment, the overlay alignment between layers is determined by calculating the centers of symmetry for each of the opposing zones on the same layer, and then calculating the difference between the two averaged centers of symmetry. For example, the center of symmetry for both working zones 72A and D and working zones 72B and C may be found by folding the images over, and the difference of these two centers of symmetry may determine the overlay error. If there is zero overlay, the centers of symmetry of each of the two opposing groups on the same layer should coincide with the Y axis that runs through the middle of the mark, i.e., between the left working zones and the right working zones.

Alternatively, periodic structures that are lateral to one another and on different layers are compared, i.e., periodic structure 74A is compared to periodic structure 74B and periodic structure 74C is compared to periodic structure 74D. In addition, periodic structures that are above or below one another are compared. i.e., periodic structure 74A is compared to periodic structure 74C and periodic structure 74B is compared to periodic structure 74D.

It should be noted that measuring overlay in the X-direction is not a limitation and that the overlay mark 70 may be rotated 90 degrees to determine the registration error between the two layers of the wafer in the Y-direction. Furthermore, two overlay marks, one of which is rotated 90 degrees from the other, can be used to determine the alignment between consecutive layers in two directions, as for example in the X and Y directions. The second mark may be positioned at various locations relative to the first mark so long as the orientation of the first and second marks are the same layer to layer (e.g., side by side or at different locations on the wafer if space is limited).

Note additionally, that if the lines shown in solid outline are printed on the first layer of the semiconductor wafer with the lines shown solid on the second layer, then on the third layer another set of lines (shown here in solid outline) are printed over, and covering, the lines of the first layer. Then the lines of the second layer are used in conjunction with lines on the third layer. Thus, each set of lines on a layer of the semiconductor wafer (except for those on the first and last layers) are used in conjunction with the lines on two layers of the semiconductor wafer, the one below and the one above. This implementation works best if the first layer cannot be detected optically when below the third layer. Alternatively, if there is sufficient space on the semiconductor wafer surface, the grating pairs for each pair of adjacent layers on the wafer could be in a different location on the wafer to minimize any "bleed through" interference from a third layer on the measurement for the top two layers of interest.

To elaborate further, finely segmented elements 78, which are used to form each of the coarsely segmented lines 76, are configured to allow the overlay mark 70 to facilitate overlay measurements that more accurately represent the degree of alignment between the wafer layers. That is, the finely segmented elements 78 serve to provide alignment information that more closely matches the alignment of the patterns of the integrated circuits that are formed on each of the two layers. The finely segmented elements 78 allow for more representative measurements, in part, due to several reasons.

One reason for which smaller overlay marks provide more accurate overlay measurements is that the smaller sized finely segmented elements are formed on the semiconductor layer with lens pattern placement errors that are more similar to the lens pattern placement errors with which the patterns for the integrated circuits are formed. Patterns are formed on wafer layers with lithographic devices such as "steppers." The lens placement errors of patterns formed upon a semiconductor wafer change with the size and spacing of the patterns due to aberrations within the stepper lenses, and with the illumination conditions (including off-axis illumination and partial coherence) used to expose the circuit pattern defined on the lithographic mask. Creating marks having feature size and pitch more comparable to that of the integrated circuit element critical dimensions, as well as using the same or similar mask pattern techniques as the circuit features (e.g., using the same or similar optical proximity correction or phase shift mask patterns), results in mark and integrated circuit patterns that are formed with a more similar degree of lens pattern placement errors. In this manner, the alignment between marks on different layers of a wafer gives a more accurate indication of the alignment between the circuit patterns. For more information regarding distortions due to stepper lens aberrations, see Lithography Process Control, by Harry J. Levinson.

In one embodiment, the feature size and pitch (e.g., the distance between the centers of the finely segmented elements of the finely segmented elements are substantially equal to those of the critical device features of the patterning step performed on the layers under test. That is, the dimensions of the finely segmented elements 78 are comparable to the dimensions of the circuit patterns. In one implementation, the line has a width that is approximately equal to the width of an integrated circuit interconnection line. Currently, circuit interconnection lines have widths that are approximately equal to or less than 0.13 um. The finely segmented elements of the current invention can be made to have widths as small as 0.05-0.2 um. However, as can be appreciated, advances in semiconductor manufacturing processes are likely to further reduce these dimensions and therefore these dimensions are by way of example and not by way of limitation.

Another reason for which smaller overlay marks provide more accurate overlay measurements is that effects of wafer fabrication asymmetries on overlay measurement may be reduced. Wafer fabrication asymmetries are shifts in the shape and size of structures or patterns that have been formed upon a wafer layer due to further fabrication processes. The effects of wafer fabrication processes on overlay marks depends on the size, spacing and density of the overlay mark structures and substructures. These shifts in shape and size affect the overlay marks such that accuracy of the overlay measurements may be deteriorated.

An exemplary wafer fabrication technique that may cause wafer structures to gain asymmetrical profiles is the sputter deposition process. The sputtering process is generally used to apply a layer of material (i.e., metal) on top of an existing wafer layer. Usually, the source of the sputtered material, a target, is located above the center of the wafer. The sputtered material travels at an angle from the target towards the outer perimeter of a wafer thereby resulting in asymmetrical deposition of material within recessed channels or over ridge-like protrusions. Specifically, the unequal accumulation of deposited material between the sidewalls of a recessed channel may cause an apparent positional shift of the recessed channel towards one side of the channel.

Another exemplary fabrication technique that may cause asymmetrical dimensions is the chemical mechanical planarization (CMP) of wafer layers. In certain circumstances, wafer layers undergo CMP before the next layer of material is deposited. The CMP device generally travels over a wafer layer in a specific direction. The CMP device, therefore, will first encounter one side of an overlay mark and then run down the opposite side of the mark. This results in a shift and change in the apparent size of the overlay mark since the material on the side of the overlay mark which is encountered first may be removed to a greater or lesser degree than the opposite side of the mark.

In both situations, the resulting asymmetries to overlay marks due to the fabrication processes may be reduced by forming smaller marks. With respect to the sputtering process, smaller recessed channels or ridges allows less sputtered material to accumulate on the respective side surfaces, thereby resulting in a smaller asymmetrical shift in shape and size. With respect to the CMP process, marks having smaller dimensions will also be shifted to a lesser degree. Conversely, there may be process situations, where widening the lines of the overlay marks may make them more robust to process variation, as for example, in cases of metal layers with large grain size. Refer to Lithography Process Control, by Harry J. Levinson, for further information on wafer fabrication asymmetries.

In the illustrated embodiment, the finely segmented elements 78 appear as thin lines that are spatially separated and parallel to each other. It should be noted, however, that lines are not a limitation and that the shape of the finely segmented elements may vary according to the specific needs of each mark. For example, the finely segmented elements may be composed of squares, rectangles, triangles, polygons, circles, ovals and the like. As should be appreciated, the finely segmented elements 78 may not have perfectly symmetrical shapes since they are typically formed via lithographic and pattern transfer processes.

Further variations include variously shaped elements that are formed within a single overlay mark. For example, one periodic structure may contain linearly shaped elements while a different periodic structure may contain circularly shaped elements. In addition, one periodic structure may contain circularly shaped elements and a different periodic structure may contain square shaped elements. Moreover, one periodic structure may contain linearly shaped elements and a different periodic structure may contain square shaped elements. Even further variations include variously shaped elements that are formed within a single periodic structure. For example, a single periodic structure may include one coarsely segmented line that is formed by linearly shaped elements and another coarsely segmented line that is formed by square shaped elements. Even further variations, include some periodic structures which are composed of finely segmented elements and others which are not composed of finely segmented elements, but rather single solid lines.

Figure 3:
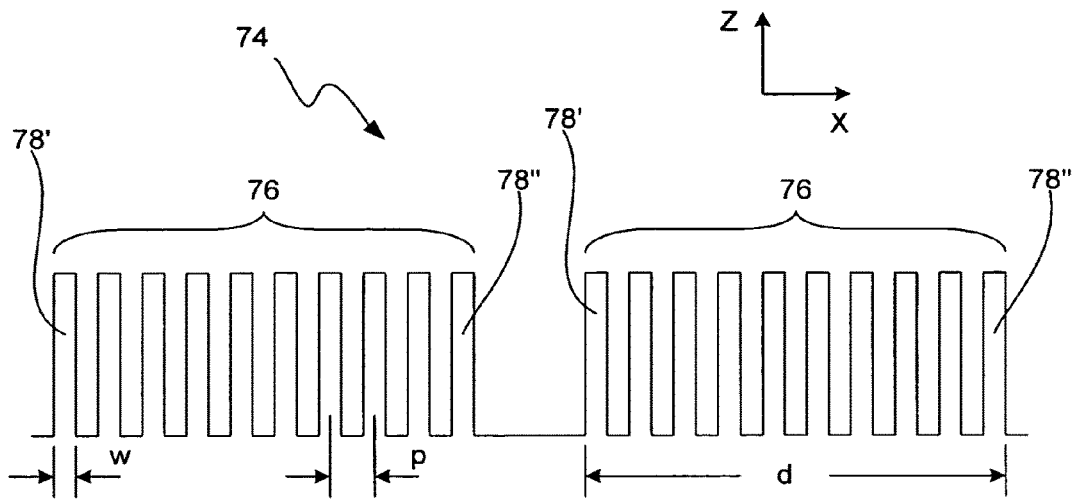
FIG. 3 is a partial side elevation view of a finely segmented periodic structure, in accordance with one embodiment of the invention.

Referring to FIG. 3, the finely segmented elements 78 will be described in greater detail. FIG. 3 is a partial side elevation view of any one of the periodic structures 74 shown in FIG. 2, in accordance with one embodiment of the invention. As shown, the coarsely segmented lines 76 are formed by a plurality of finely segmented elements 78. In this particular embodiment, the finely segmented elements 78 represent bars, which are symmetrically distributed relative to the center of the coarsely segmented line 76, and which having equal fine widths, w, and fine pitch, p (distance between centers), there between. It should be noted, however, that this is not a limitation and that the widths and pitch, as well as the distribution, may vary according to the specific needs of each device. The linewidth, d, of the coarsely segmented lines 76 is defined as the distance between the outer edges of the very first and the very last bar 78' and 78" of the plurality of finely segmented bars 78. In the illustrated embodiment, there are 10 finely segmented bars.

It has been found that stepper aberrations (not metrology tool aberrations) such as coma may cause an apparent overlay error in cases where the overlay mark is finely segmented. That is, in addition to having the tendency to cause pattern placement errors, stepper coma may also have the tendency to modify the dimensions of the finely segmented elements, in particular, the first and last bars that make up the coarsely segmented line (e.g., bars 78' and 78"). By "modify the dimensions", it is generally meant that the first and last bars may become thinner or wider. In most cases, when one bar becomes wider the other bar becomes thinner. For example, coma may cause the last bar to become wider and the first bar to become thinner. This may also be caused by the proximity of the bars to the open space between coarsely segmented lines. As should be appreciated, this type of modification tends to introduce an apparent overlay shift (i.e., the line appears to shift from the left to the right) and thus the line may not be measured correctly. In one embodiment, the layout of the periodic structures may be reconfigured to compensate for this apparent shift (see FIGS. 4, 5A, and 5B).

In lithography, a clear field generally refers to a series of periodic structures that are surrounded by an open space (e.g., etched) and a dark field generally refers to a series of periodic structures that are surrounded by a closed space (e.g., not etched). The clear fields generally appear brighter and the dark fields generally appear darker. In this particular embodiment, the clear field is a clearing between a group of finely segmented elements such as the bars of FIG. 3, and the dark field is a closed space between a group of finely segmented elements such as the bars of FIG. 3. It is generally believed that the clear fields and dark fields may be configured to alter the formation of the lines in such a way that that the apparent shift, which is caused by the wider and thinner bars, cancel or balance out. In one implementation, the balancing is done within each periodic structure. For example, each of the working zones includes fine segmentation that comprises both a clear field and a dark field. For example, some of the coarsely segmented lines have clear fields and some have dark fields.

In another implementation, the balancing is done between two periodic structures of different working zones. For example, at least a first working zone includes a periodic structure with fine segmentation that comprises a clear field and at least a second working zone includes a periodic structure with fine segmentation that comprises a dark field. In most cases, the first and second working zones are opposed working zones that are on the same layer. These implementations will be described in greater detail below with reference to FIGS. 4, 5A, and 5B.

Figure 4:
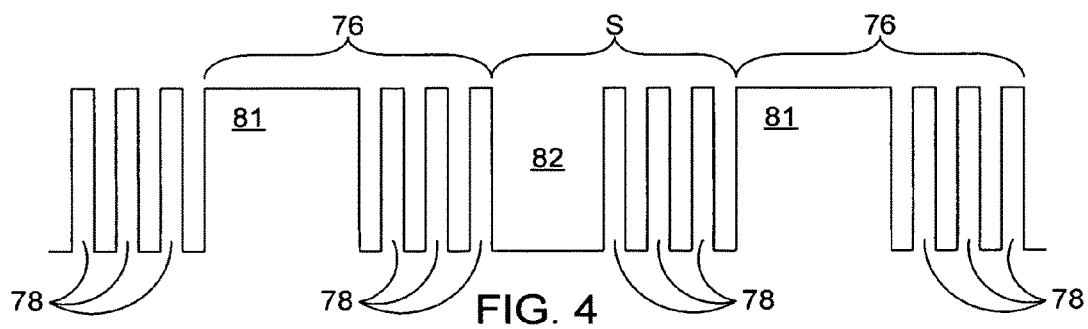
FIG. 4 is a partial side elevation view of a finely segmented periodic structure, in accordance with one embodiment of the invention.

FIG. 4 is a partial side elevation view of any one of the periodic structures 74 shown in FIG. 2, in accordance with one embodiment of the invention. By way of example, FIG. 4 generally corresponds to the first implementation described above. As shown, the coarsely segmented lines 76 are formed by a plurality of finely segmented bars 78 and at least one dark field 81. The coarsely segmented lines 76 are separated by a separation, S, that includes a plurality of finely segmented bars 78 and at least one clear field 82. The geometry of the finely segmented lines, dark fields and clear fields may be widely varied. The geometry of these components generally depends on the partial coherence of illumination and coma aberrations of the optics of the stepper lens. Dual tone structures, in which both lines and spaces are partially segmented tend to represent better the pattern placement errors suffered by device structures, rather than structures comprising either one or the other.

Figure 5A:
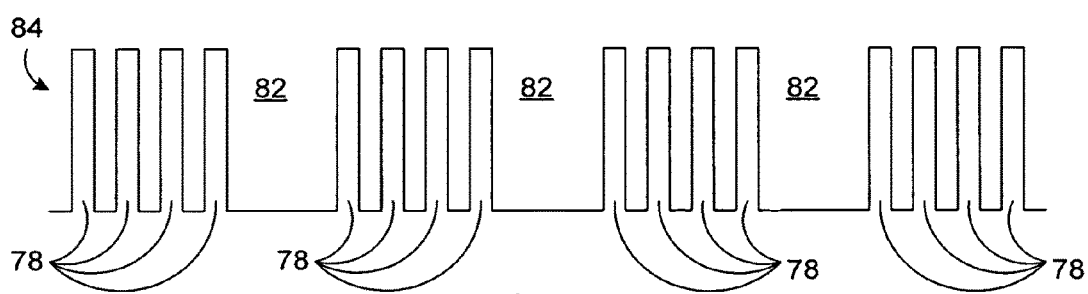
FIGS. 5A and 5B are each a partial side elevation view of a finely segmented periodic structure, in accordance with one embodiment of the invention.

FIGS. 5A & B are partial side elevation views of two distinct periodic structures 84 and 85, in accordance with one embodiment of the invention. In most cases, the periodic structures 84 and 85 represent periodic structures, which are from opposing working zones, and which are positioned in the same layer. For example, periodic structure 84 may correspond to periodic structure 74A while periodic structure 85 may correspond to periodic structure 72D. It should be noted, however, that this is not a limitation.

Figure 5B:
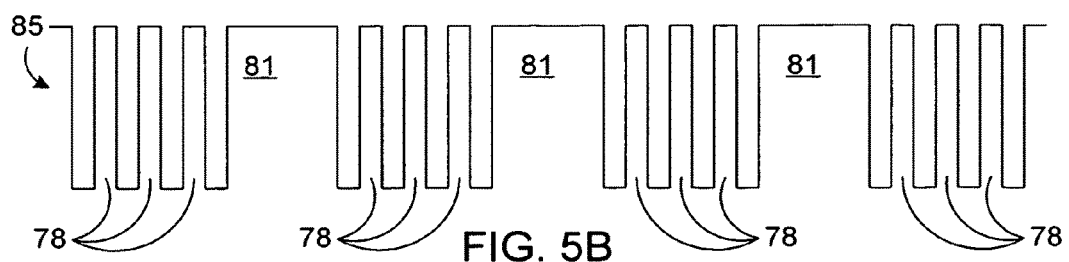

Referring to FIG. 5A, the first periodic structure 84 includes coarsely segmented lines 76, which are formed by a plurality of finely segmented bars 78, and which are separated by clear fields 82. Referring to FIG. 5B, the second periodic structure 85 includes coarsely segmented lines 76, which are formed by a plurality of finely segmented bars 78, and which are separated by dark fields 81. The geometry of the finely segmented lines, dark fields and clear fields may be widely varied. In this particular embodiment, the size shape (although inverse) and position of the dark fields generally corresponds to the size shape (although inverse) and position of the clear fields.

As can be seen from the foregoing, the advantages of the X-configuration are numerous. For instance, the X-configuration may provide more information than the standard box-in-box target by filling the perimeter of the mark from center to edge. It may also provide more information by increasing the number of edges (e.g., coarsely segmented lines) as well as their lengths. Apart from providing more information by increasing the number of edges and their lengths, the X-configuration exhibits further advantage over the generic box-in-box target due to additional built-in symmetry. Namely, in the generic box-in-box structures there are inner and outer layers. Their swap would result in different pattern, and therefore—overlay result, due to different information distribution of inner and outer marks, and due to different optical behavior of the metrology tool in regions close to and far from the FOV center. From this point of view, the "X"-target structure is basically invariant to the layer swap (up to mirror transformation). Furthermore, the X configuration exhibits 180 degree rotational symmetry that helps to overcome anti-symmetrical coma patterns, i.e., coma will cancel out.

Figure 6:
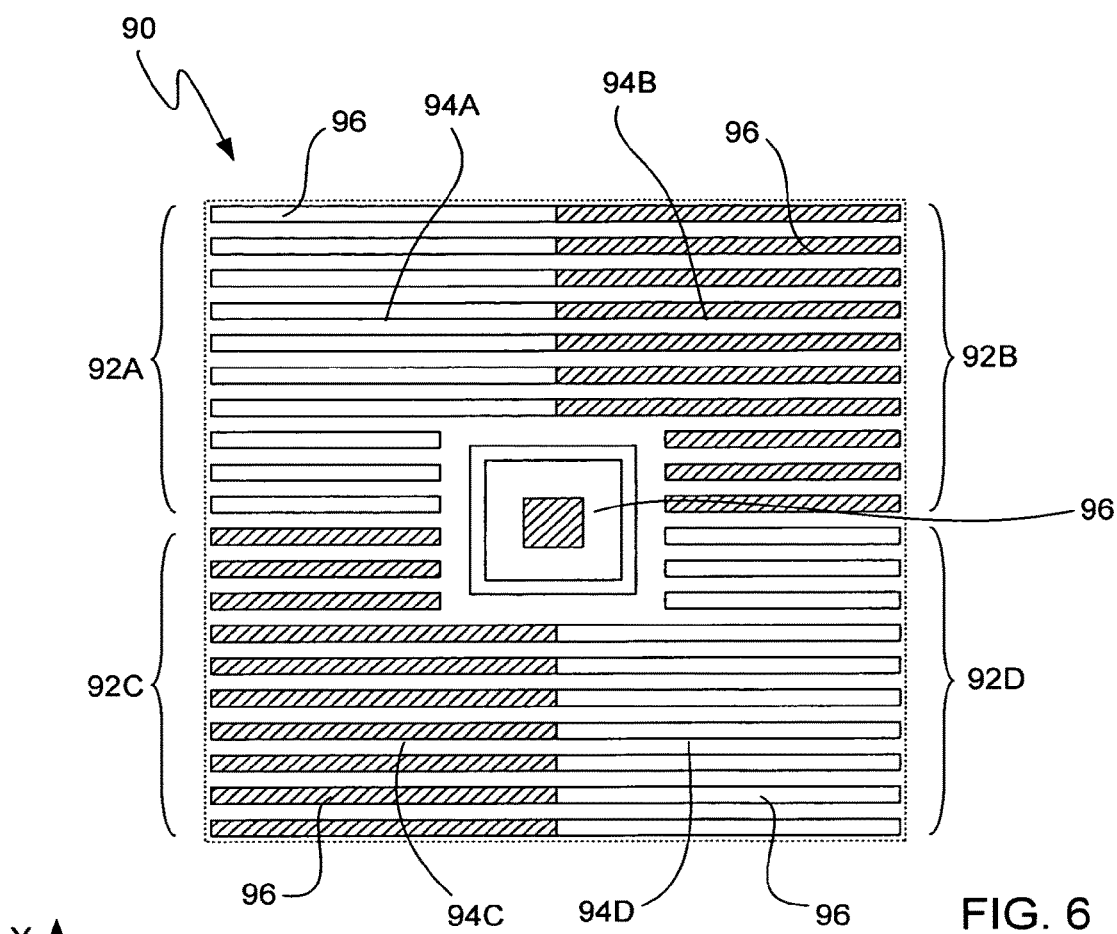
FIG. 6 is a top plan view of an overlay mark, in accordance with an alternate embodiment of the present invention.

FIG. 6 is a top plan view of an overlay mark 90, in accordance with an alternate embodiment of the invention. By way of example, the overlay mark 90 may generally correspond to the overlay mark shown in FIG. 2. Overlay mark 90 contains four working zones 92A-D for determining the registration error between two wafer layers (one layer is represented by cross-hatching, the other is not). Each of the working zones includes a periodic structure 94 comprised by a plurality of coarsely segmented lines 96. In a manner similar to the X target of FIG. 2, the periodic structures 94A and D positioned in the first and fourth zones 92 A and D are disposed in a first layer of the wafer while periodic structures 94 B and C positioned in the second and third zones 92 B and C are disposed in a second layer of the wafer. Furthermore, periodic structures on the same layer, as for example structures 94 A and D, are in diagonally opposed positions thereby forming an overlay mark with an X configuration.

In this particular embodiment, the coarsely segmented lines are horizontally positioned and therefore they are configured to measure overlay in the Y-direction. It should be noted, however, that this is not a limitation and that the target may be rotated so as to measure overlay in the X-direction. Also in this embodiment, the coarsely segmented lines are solid structures that are elongated and rectangular in shape. It should also be noted that this is not a limitation and that the coarsely segmented lines may be formed by a plurality of finely segmented elements, which may be produced according to the finely segmented elements described in FIG. 4.

In contrast to the mark of FIG. 2, each of the working zones 92, and more particularly each of the periodic structures 94 in FIG. 6 has an "L shaped" outline or shape in order to accommodate an additional structure 96 in the center of the mark 90. In the illustrated embodiment, the additional structure 96 represents a standard box in box structure as described in the background of this application. As such, the "X" configured mark 90 can be acquired and measured by standard box in box metrology tools and algorithms, i.e., existing equipment and software may be used.

Figure 7:
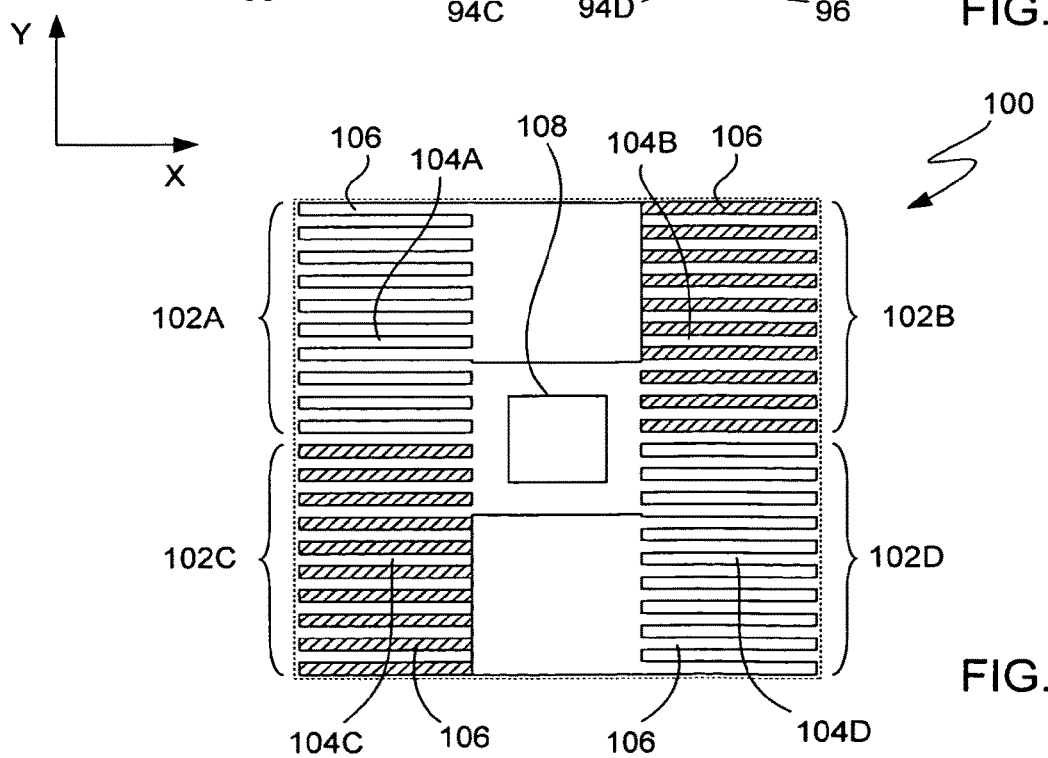
FIG. 7 is a top plan view of an overlay mark, in accordance with an alternate embodiment of the present invention.

FIG. 7 is a top plan view of an overlay mark 100, in accordance with an alternate embodiment of the invention. By way of example, the overlay mark 100 may generally correspond to the overlay mark shown in FIG. 2. Overlay mark 100 contains four working zones 102A-D for determining the registration error between two wafer layers (one layer is represented by cross-hatching, the other is not). Each of the working zones 102 includes a periodic structure 104 comprised by a plurality of coarsely segmented lines 106. In a manner similar to the "X" target of FIG. 2, the periodic structures 104A and D positioned in the first and fourth zones 102 A and D are disposed in a first layer of the wafer while periodic structures 104 B and C positioned in the second and third zones 102 B and C are disposed in a second layer of the wafer. Furthermore, periodic structures on the same layer, as for example structures 104 A and D, are in diagonally opposed positions thereby forming an overlay mark with an X configuration.

In this particular embodiment, the coarsely segmented lines 106 are horizontally positioned and therefore they are configured to measure overlay in the Y-direction. It should be noted, however, that this is not a limitation and that the mark 100 may be rotated so as to measure overlay in the X-direction. Also in this embodiment, the coarsely segmented lines are solid structures that are elongated and rectangular in shape. It should also be noted that this is not a limitation and that the coarsely segmented lines may be formed by a plurality of finely segmented elements, which may be produced according to the finely segmented elements described in FIG. 4.

In contrast to the mark of FIG. 2, each of the working zones 102, and more particularly each of the periodic structures 104 in FIG. 7 has a "rectangular" outline or shape in order to accommodate an additional structure 108 in the center of the mark 100. In the illustrated embodiment, the additional structure 108 represents a standard box in box structure as described in the background of this application. As such, the X configured mark 100 can be acquired and imaged by standard box in box overlay metrology tools and algorithms. It should be noted, however, that this is not a limitation and that the additional structure may represent other structures, as for example, a pattern recognition structure, which can be recognized and acquired by optical pattern recognition tools and algorithms. Both configurations have the advantage that no change is necessary to existing equipment and software.

Figure 8:
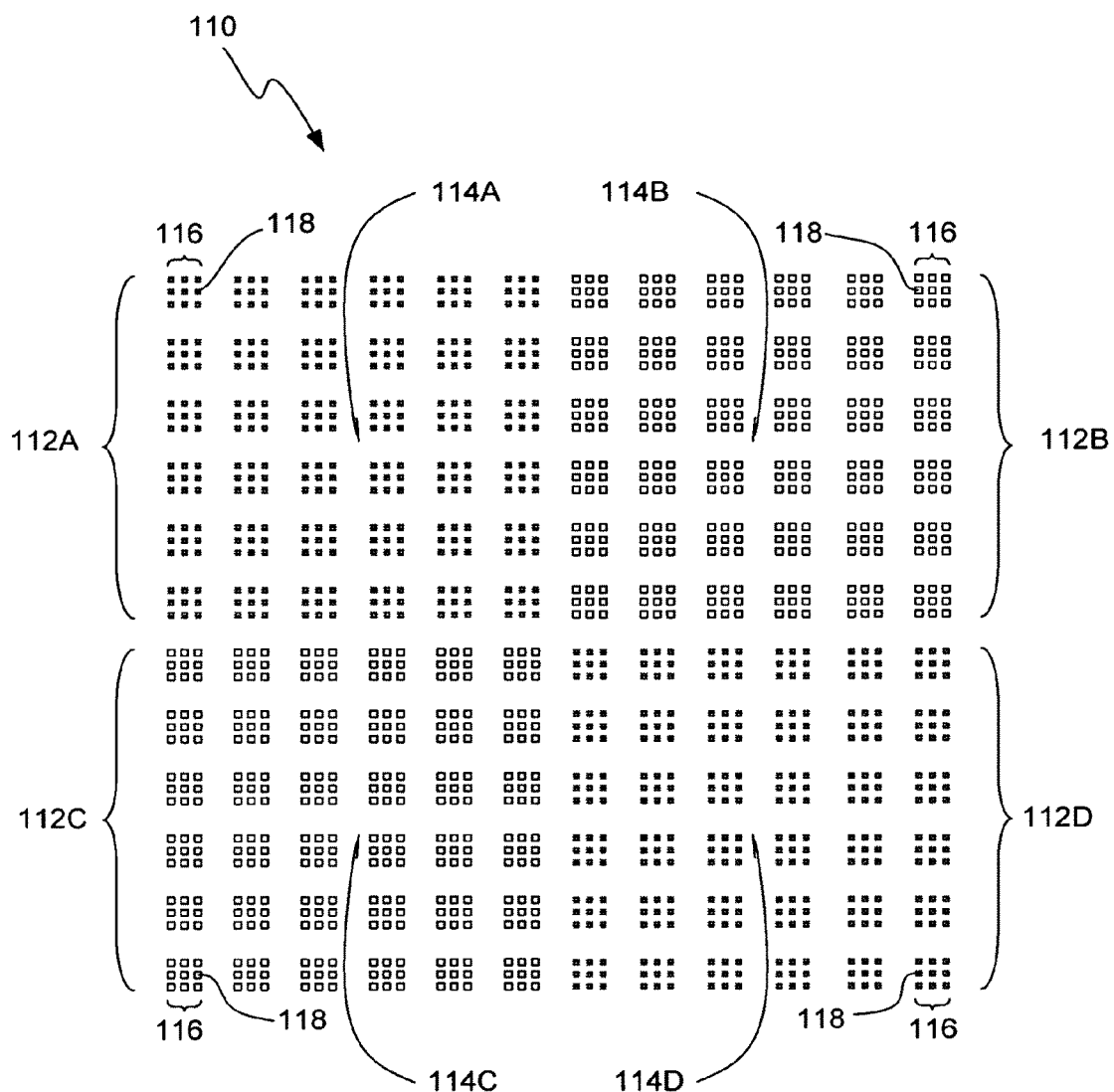
FIG. 8 is a top plan view of an overlay mark, in accordance with an alternate embodiment of the present invention.

FIG. 8 is a top plan view of an overlay mark 110, in accordance with an alternate embodiment of the present invention. By way of example, overlay mark 110 may correspond to the mark of FIG. 2. It should be noted, however, that unlike the mark of FIG. 2, the overlay mark 110 is configured to measure overlay in two separate directions. As such, mark 110 obviates the need to have one mark for each direction in which overlay needs to be measured. Overlay mark 110 is shown in a configuration that results when the tested layers of a wafer are in perfect alignment.

The overlay mark 110 includes a plurality of working zones 112 for determining the registration error between two wafer layers in two different directions. In the illustrated embodiment, the overlay mark 110 includes four square shaped working zones 112, which are configured to substantially fill a field of view (not shown) of the metrology tool used to image the overlay mark 110. The working zones 112 represent the actual areas of the mark that are used to calculate alignment between different layers of the wafer. As mentioned previously, the working zones 112 are spatially separated from one another so that they do not overlap portions of an adjacent working zone of the second layer.

In this embodiment, the working zones are configured to provide overlay information in two directions, as for example, in the X and Y directions. Of the four working zones 112A-D, two of them 112A and D are disposed in the first layer and two of them 112B and C are disposed in the second layer (the first layer is represented by solid fill, the second layer is represented by no fill). Working zones 112A and D, which are disposed on the same first layer, are positioned opposite one another at a first vertical angle while working zones 112B and 112C, which are disposed on the same second layer, are positioned opposite one another at a second vertical angle (e.g., diagonally). These cross-positioned structures form an "X" shaped pattern.

Each of the working zones 112 contains an individual periodic structure 114, as for example, periodic structures 114A-D. As shown, each of the periodic structures 114 substantially fills the perimeter of its corresponding working zone 112. As should be appreciated, each of the periodic structures 114 are formed in the layer of its corresponding working zone 112. The periodic structures 114 include coarsely segmented elements 116 that are arranged in spaced apart rows and columns. Each of the coarsely segmented elements 116, in turn, are formed by finely segmented elements 118. The finely segmented elements 118 are also arranged in spaced apart rows and columns. The individual coarsely segmented elements 116 and finely segmented elements 118 may be configured with a variety of sizes, shapes and distributions. In the illustrated embodiment, both the coarsely segmented elements 116 and finely segmented elements 118 are square shaped and equally spaced from an adjacent element. As should be appreciated, overlay mark 110 can be used to measure the misregistration value in two separate directions that are perpendicular to each other since the mark 110 has the same repeating structural pattern in orthogonal directions.

Figure 9:
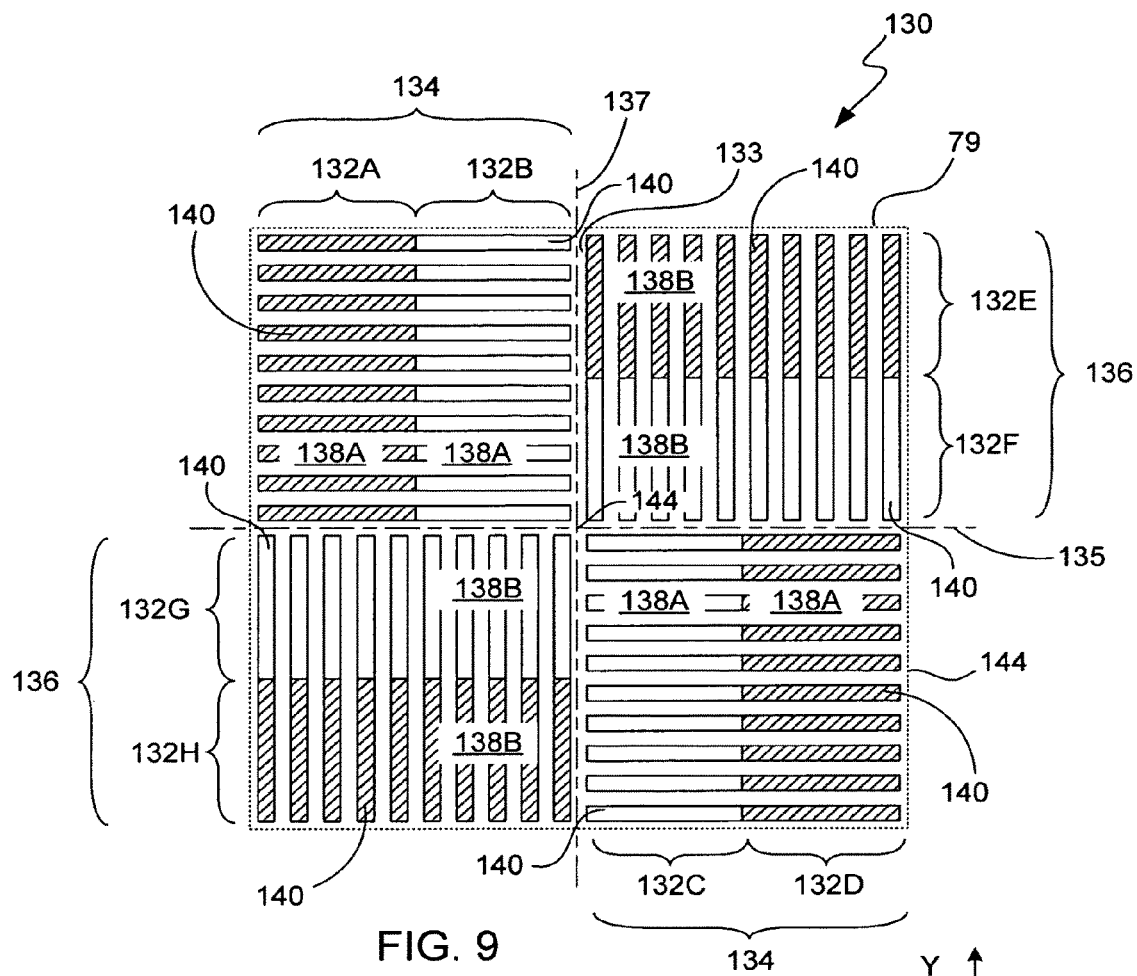
FIG. 9 is a top plan view of an overlay mark, in accordance with an alternate embodiment of the present invention.

FIG. 9 is a top plan view of an overlay mark 130, in accordance with an alternate embodiment of the invention. By way of example, overlay mark 130 may correspond to the mark of FIG. 2. It should be noted, however, that unlike the mark of FIG. 2, the overlay mark 130 of FIG. 9 is configured to measure overlay in two separate directions. As such, mark 130 obviates the need to have one mark for each direction in which overlay needs to be measured. Overlay mark 130 is shown in a configuration that results when the tested layers of a wafer are in perfect alignment. The overlay mark 130 is generally provided to determine the relative shift between two or more successive layers of a wafer or between two or more separately generated patterns on a single layer of a wafer. For ease of discussion, the overlay mark 130 will be described in context of measuring overlay between different layers of a substrate. It should be noted, however, that the overlay mark in this figure may also be used to measure two or more separately generated patterns on a single layer of a substrate.

The overlay mark 130 includes a plurality of working zones 132 for determining the registration error between two wafer layers in two different directions. In the illustrated embodiment, the overlay mark 130 includes eight rectangular shaped working zones 132, which are configured to substantially fill its perimeter 79. The working zones 132 represent the actual areas of the mark that are used to calculate alignment between different layers of the wafer. As mentioned previously, the working zones 132 are spatially separated from one another so that they do not overlap portions of an adjacent working zone. In this particular configuration, some of the working zones are separated via exclusion zones while other working zones are positioned next to an adjacent working zone. For example, working zone 132B is separated from working zones 132 E and F via an exclusion zone 133 while working zones 132E and F are positioned next to one another at their edges.

To facilitate discussion, the working zones 132 are grouped into a first working group 134 and a second working group 136. The first working group 134 includes four working zones 132A-D that are configured to provide overlay information in a first direction. By way of example, the first direction may be the Y direction. Of the four working zones 132A-D, two of them 132A and D are disposed in the first layer and two of them 132 B and C are disposed in the second layer (the first layer is represented by cross hatching, the second layer is represented by no cross hatching). As should be appreciated, for this mark configuration and in the case of zero overlay error (as shown), the centers of symmetry 135 of working zones 132A&D and working zones 132B&C coincide exactly. The second working group 136 includes four working zones 132E-H configured to provide overlay information in a second direction that is perpendicular to the first direction. By way of example, the second direction may be the X direction. Of the four working zones 132E-H, two of them 132 E and H are disposed in the first layer and two of them 132 F and G are disposed in the second layer (the first layer is represented by cross hatching, the second layer is represented by no cross hatching). Similarly to the above, for this mark configuration and in the case of zero overlay (as shown), the centers of symmetry 137 of working zones 132E&H and working zones 132F&G coincide exactly.

As should be appreciated, each of the groups 134 and 136 represents an "X"-configured mark (albeit offset). For example, working group 134 includes working zones 132A&D, which are on the same first layer and in diagonally opposed positions relative to one another, and working zones 132B&C, which are on the same second layer and in diagonally opposed positions relative to one another. Further, working zones 132A&D are angled relative to working zones 1322B&C. Further still, working zone 132A is spatially offset from working zone 132D, and working zone 132B is spatially offset from working zone 132D.

In addition, working group 136 includes working zones 132E&H, which are on the same first layer and in diagonally opposed positions relative to one another, and working zones 132F&G, which are on the same second layer and in diagonally opposed positions relative to one another. Further, working zones 132E&H are angled relative to working zones 1322F&G. Further still, working zone 132E is spatially offset from working zone 132H, and working zone 132F is spatially offset from working zone 132G. In essence, this particular mark produces two "'X'" configured marks that are positioned orthogonal to each other, i.e., working group 194 and working group 196.

To elaborate further, a working zone on one layer is generally juxtaposed relative to a working zone on another layer. For example, in the first working group, working zone 132A is juxtaposed relative to working zone 132B and working zone 132C is juxtaposed relative to working zone 132D. Similarly, in the second working group, working zone 132E is juxtaposed relative to working zone 132H and working zone 132F is juxtaposed relative to working zone 132G. Of the two juxtaposed pairs, the working zone on the second layer is typically positioned closer to the center of the FOV than the working zone on the first layer. For example, working zones 132B and C and working zones 132 F and G are positioned closer to the center 142 of the FOV 144 than their juxtaposed working zones 132A and D and working zones 132 E and H, respectively. Furthermore, within each of the working groups, the juxtaposed pairs are positioned in an opposed relationship (e.g., diagonal) relative to the other juxtaposed pair in the group. For example, juxtaposed pairs 132A&B are positioned opposite juxtaposed pairs 132C&D, and juxtaposed pairs 132E&F are positioned opposite juxtaposed pairs 132G&H.

As should be appreciated, in this particular mark, the configuration of the working zones is rotationally symmetric (+90, 180, 270, 360 degrees around the center of the mark). This is typically done to reduce the impact of radial and axial variations across the field of view of the metrology tool, as for example, radial and axial variations caused by non-uniform optical aberrations and illumination that may cause tool induced shifts (TIS). Radial variations generally refer to variations that radiate from the center of the mark to the outer regions of the mark. Axial variations generally refer to variations that occur in directions along the axis of the mark, as for example, in the X direction from the left to the right portions of the mark, and in the Y direction from the lower to the upper portions of the mark.

Each of the working zones 132A-H includes a periodic structure 138 comprised by a plurality of coarsely segmented lines 140. The linewidths. D, and spacings, s, of the coarsely segmented lines may be widely varied. As shown, each of the periodic structures 138 substantially fills the perimeter of its corresponding working zone 132. As should be appreciated, the periodic structures 138 are also disposed on the layer of its corresponding work zone 132.

For ease of discussion, the periodic structures 138 may be broken up into a first periodic structure 138A that is associated with the first working group 134 and a second periodic structure 138B that is associated with the second working group. As shown, the first periodic structures 138A are all oriented in the same direction, i.e., the coarsely segmented lines 140 are parallel and horizontally positioned relative to each other. The second periodic structures 138B are also all oriented in the same direction (albeit differently than the first periodic structures), i.e., the coarsely segmented lines 140 are parallel and vertically positioned relative to each other. As such, the periodic structures 138A in the first working group 134 are orthogonal to the periodic structures 138B in the second working group 136.

In one embodiment, the coarsely segmented lines of juxtaposed periodic structures are aligned with one another, i.e., if we ignore the different layers they appear to be continuous gratings. For example, the coarsely segmented lines of working zone 132A may align with the coarsely segmented lines of working zone 132B and coarsely segmented lines of working zone 132C may align with the coarsely segmented lines of working zone 132D. In addition, the coarsely segmented lines of working zone 132E may align with the coarsely segmented lines of working zone 132F and coarsely segmented lines of working zone 132G may align with the coarsely segmented lines of working zone 132H.

Figure 10:
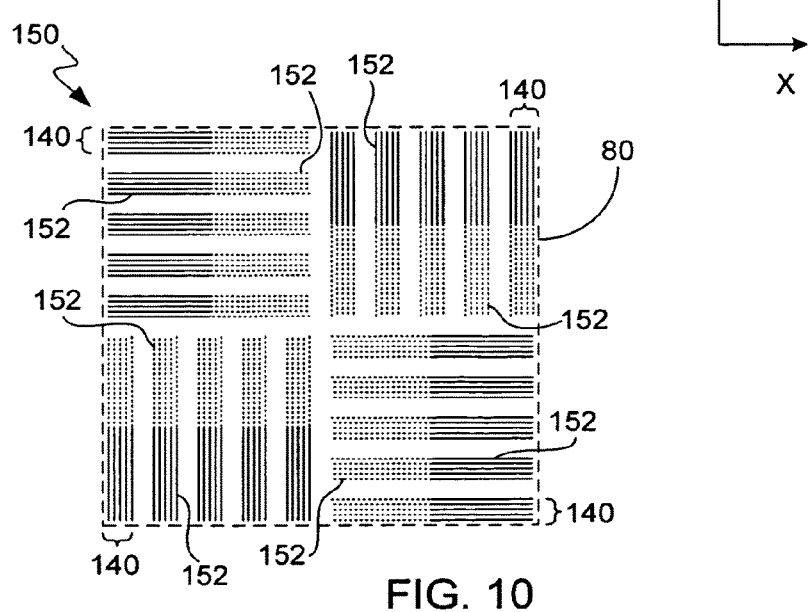
FIG. 10 is a top plan view of an overlay mark, in accordance with an alternate embodiment of the present invention.

FIG. 10 is a top plan view of the overlay mark 150, in accordance with an alternate embodiment of the invention. In this particular embodiment, the coarsely segmented lines 140 are formed by a plurality of finely segmented elements 152. The finely segmented elements 152 generally correspond to the finely segmented elements 178 described in FIG. 2.

FIG. 11 is a top plan view of an overlay mark 170, in accordance with an alternate embodiment of the present invention. By way of example, the overlay mark 170 may generally correspond to the overlay mark shown in FIGS. 6 & 9. Similarly to the overlay mark 130, overlay mark 170 contains eight working zones 172A-H for determining the registration error between two wafer layers in two different directions (one layer is represented by cross-hatching, the other is not). Each of the working zones includes a periodic structure 174 comprised by a plurality of coarsely segmented lines 176. Similarly to the overlay mark 90, each of the working zones 172, are configured to accommodate an additional structure 178 in the center of the mark 170. In the illustrated embodiment, the working zones 172A-H are disposed around the outer region of the mark while the additional structure 178 is disposed in the center of the mark. The additional structure 178 may represent a standard box in box structure as described in the background of this application. As such, the mark 170 can be acquired and measured by standard box in box metrology tools and algorithms, i.e., existing equipment and software may be used.

Figure 12:
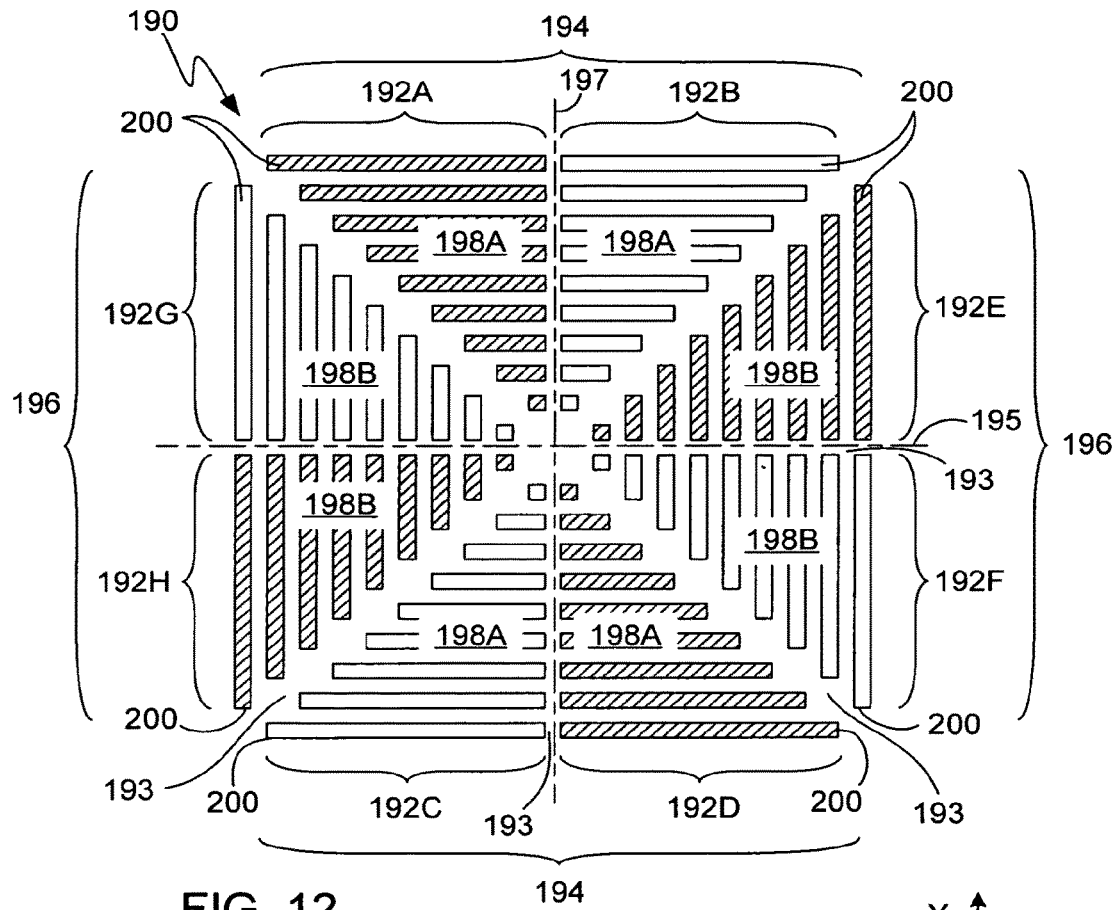
FIG. 12 is a top plan view of an overlay mark, in accordance with an alternate embodiment of the present invention.

FIG. 12 is a top plan view of an overlay mark 190, in accordance with an alternate embodiment of the present invention. By way of example, overlay mark 190 may correspond to the mark of FIG. 9. Like the mark of FIG. 9, the overlay mark 190 of FIG. 12 is configured to measure overlay in two separate directions. As such, mark 190 obviates the need to have one mark for each direction in which overlay needs to be measured. In contrast to the mark of FIG. 9, the mark 190 includes triangularly shaped working zones. Overlay mark 190 is shown in a configuration that results when the tested layers of a wafer are in perfect alignment.

The overlay mark 190 includes a plurality of working zones 192 for determining the registration error between two wafer layers in two different directions. In the illustrated embodiment, the overlay mark 140 includes eight triangularly shaped working zones 192, which are configured to substantially fill its perimeter. The working zones 192 represent the actual areas of the mark that are used to calculate alignment between different layers of the wafer. As mentioned previously, the working zones 192 are spatially separated from one another so that they do not overlap portions of an adjacent working zone. In this particular configuration, all of the working zones 192 are separated via exclusion zones 193.

To facilitate discussion, the working zones 192 are grouped into a first working group 194 and a second working group 196. The first working group 194 includes four working zones 192A-D that are configured to provide overlay information in a first direction. By way of example, the first direction may be the Y direction. Of the four working zones 192A-D, two of them 192A and D are disposed in the first layer and two of them 192 B and C are disposed in the second layer (the first layer is represented by solid lines, the second layer is represented by dashed lines). As should be appreciated, for this mark configuration and in the case of zero overlay (as shown), the centers of symmetry 195 of working zones 192A&D and working zones 192B&C coincide exactly. The second working group 196 includes four working zones 192E-H configured to provide overlay information in a second direction that is perpendicular to the first direction. By way of example, the second direction may be the X direction. Of the four working zones 192E-H, two of them 192 E and H are disposed in the first layer and two of them 192 F and G are disposed in the second layer (the first layer is represented by solid lines, the second layer is represented by dashed lines). Similarly to the above, for this mark configuration and in the case of zero overlay (as shown), the centers of symmetry 197 of working zones 192E&H and working zones 192F&G coincide exactly. In addition, and all of the working zones 192 are equally positioned relative to the center of the mark.

As should be appreciated, each of the groups 194 and 196 represents an "X"-configured mark. For example, working group 194 includes working zones 192A&D, which are on the same first layer and in diagonally opposed positions relative to one another, and working zones 192B&C, which are on the same second layer and in diagonally opposed positions relative to one another. Further, working zones 192A&D are angled relative to working zones 192B&C. Further still, working zone 192A is spatially offset from working zone 192D, and working zone 192B is spatially offset from working zone 192D.

In addition, working group 136 includes working zones 192E&H, which are on the same first layer and in opposed positions relative to one another, and working zones 192F&G, which are on the same second layer and in opposed positions relative to one another. Further, working zones 192E&H are angled relative to working zones 192F&G. Further still, working zone 192E is spatially offset from working zone 192H, and working zone 192F is spatially offset from working zone 192G. In essence, this particular mark produces two "X" configured marks that are positioned orthogonal to each other, i.e., working group 194 and working group 196.

To elaborate further, a working zone on one layer is generally juxtaposed relative to a working zone on another layer. For example, in the first working group, working zone 192A is juxtaposed relative to working zone 192B and working zone 192C is juxtaposed relative to working zone 192D. Similarly, in the second working group, working zone 192E is juxtaposed relative to working zone 192H and working zone 192F is juxtaposed relative to working zone 192G. For this mark configuration and in the case of zero overlay (as shown), all of the working zones 192 are equally positioned relative to the center of the mark. Furthermore, within each of the working groups, the juxtaposed pairs are positioned in an opposed relationship (e.g., upper/lower and right/left) relative to the other juxtaposed pair in the group. For example, juxtaposed pairs 192A&B are positioned opposite juxtaposed pairs 192C&D, and juxtaposed pairs 192E&F are positioned opposite juxtaposed pairs 192G&H.

As should be appreciated, in this particular mark, the configuration of the working zones is rotationally symmetric (+90, 180, 270, 360 degrees around the center of the mark) without biasing the center or periphery with one or other layer, i.e., the mark is invariant. This is typically done to reduce the impact of radial and axial variations across the field of view of the metrology tool, as for example, radial and axial variations caused by optical aberrations and illuminations that may cause tool induced shifts (TIS).

Each of the working zones 192 includes a periodic structure 198 comprised by a plurality of coarsely segmented lines 200. The linewidths, D, and spacings, s, of the coarsely segmented lines may be widely varied. As shown, each of the periodic structures 198 substantially fills the perimeter of its corresponding working zone 192. As should be appreciated, the periodic structures 198 are also disposed on the layer of its corresponding work zone 192.

For ease of discussion, the periodic structures 198 may be broken up into a first periodic structure 198A that is associated with the first working group 194 and a second periodic structure 198B that is associated with the second working group 196. As shown, the first periodic structures 198A are all oriented in the same direction, i.e., the coarsely segmented lines 190A are parallel and horizontally positioned relative to each other. The second periodic structures 198B are also all oriented in the same direction (albeit differently than the first periodic structures), i.e., the coarsely segmented lines 198B are parallel and vertically positioned relative to each other. As such, the periodic structures 198A in the first working group 194 are orthogonal to the periodic structures 198B in the second working group 196. Furthermore, in order to accommodate each zone within the FOV, the coarsely segmented lines 190 decrease in length as they move from the outer regions of the mark to the inner regions of the mark. Although not shown, the coarsely segmented line may be formed by a plurality of finely segmented elements to further enhance this mark.

Figure 13:
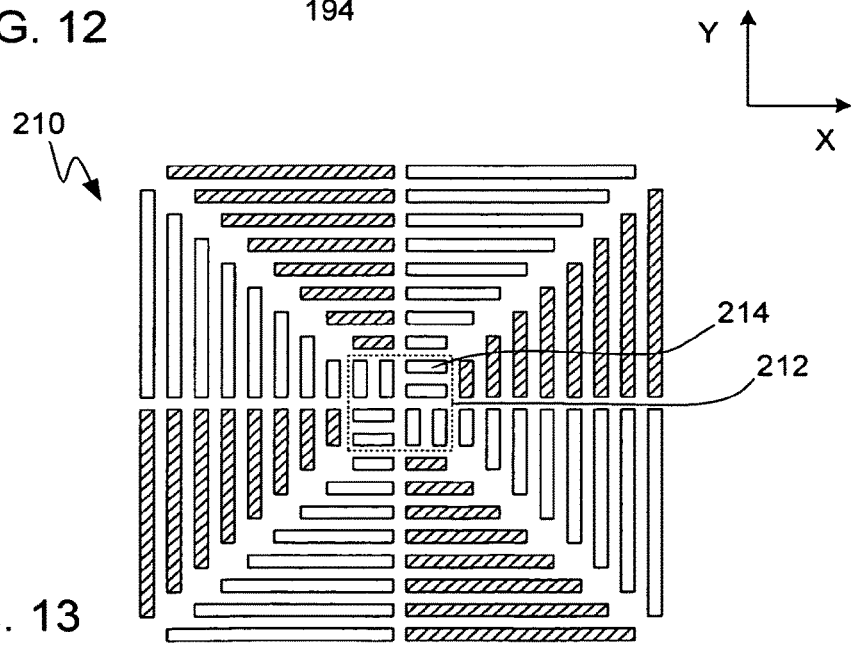
FIG. 13 is a top plan view of an overlay mark, in accordance with an alternate embodiment of the present invention.

FIG. 13 is a top plan view of an overlay mark 210, in accordance with an alternate embodiment of the present invention. As shown, mark 210 has the same general layout and characteristics as mark 190 of FIG. 12, i.e., eight triangularly shaped working zones. Mark 210 differs from mark 190, however, in that it biases the center of the mark with a grating pattern 212 formed on one of the two layers. The grating pattern 212 is typically used in cases where the mark quality in one layer is poorer than the mark quality in the other layer due to contrast or graininess. That is, the information (e.g., edges) in a layer where contrast is low is increased. Alternatively, biasing the center of the FOV with one layer may protect it from process damage. The grating pattern 212 may be widely varied. For example, grating pattern may include any number of lines in any number of distributions and sizes. In this particular embodiment, the grating pattern is formed on the second layer and it consists of groups of two coarsely segmented lines 214 that alternate in direction (e.g., X and Y directions) around the center of the mark.

Figure 14:
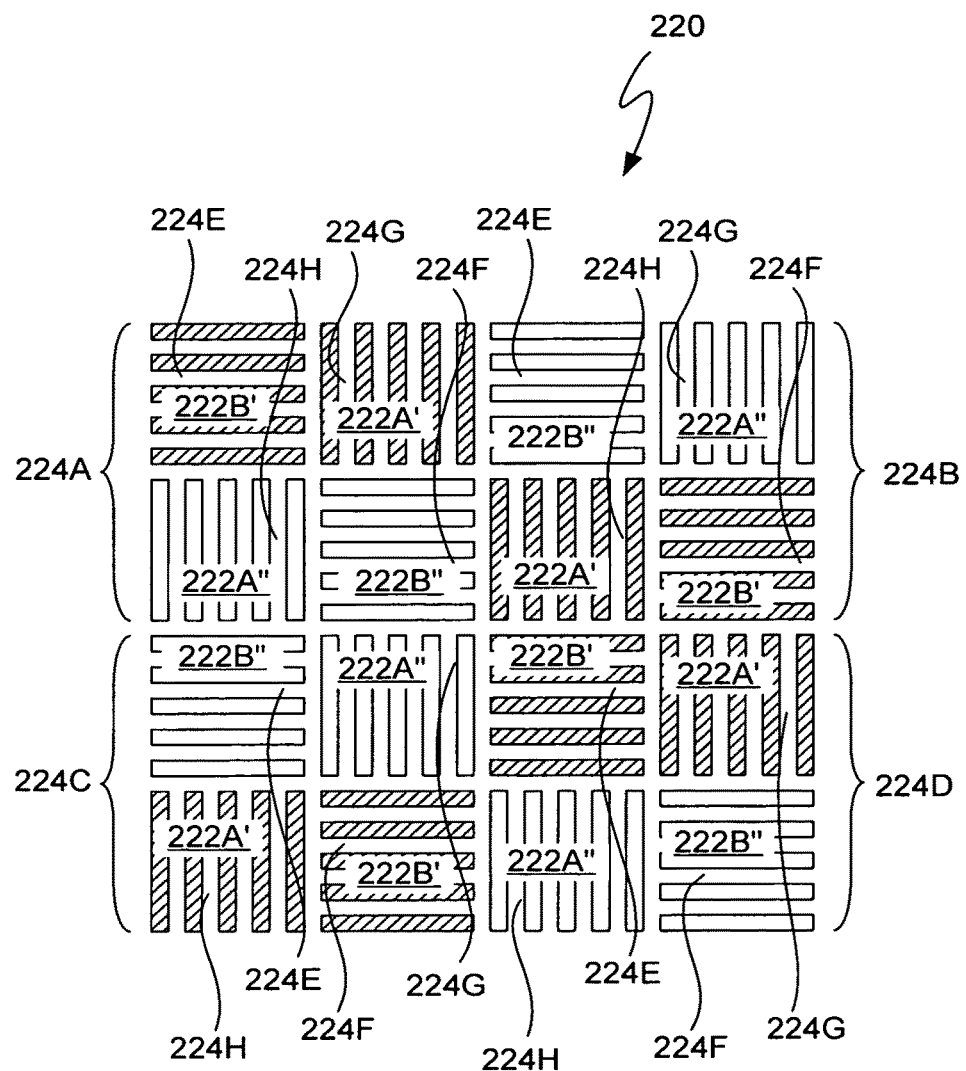
FIG. 14 is a top plan view of an overlay mark, in accordance with an alternate embodiment of the present invention.

FIG. 14 is a top plan view of an overlay mark 220, in accordance with an alternate embodiment of the present invention. By way of example, overlay mark 220 may generally correspond to the overlay mark shown in FIG. 9. Like the overlay mark of FIG. 9, overlay mark 220 is configured to measure overlay in two separate directions. As such, mark 220 obviates the need to have one mark for each direction in which overlay needs to be measured. Overlay mark 220 is shown in a configuration that results when the tested layers of a wafer are in perfect alignment.

The overlay mark 220 includes a plurality of working zones 222 for determining the registration error between two wafer layers in two different directions. In the illustrated embodiment, the overlay mark 222 includes sixteen square shaped working zones 222, which are configured to substantially fill its perimeter. Each of the working zones 222 includes a periodic structure of coarsely segmented lines. Although not shown, it should be appreciated that in some embodiments the coarsely segmented lines may be formed by a plurality of finely segmented elements, as for example, any configuration described or shown herein (i.e., FIGS. 3-5).

Of the 16 working zones, 8 of the working zones 222A are oriented in the X direction and 8 of the working zones 222B are oriented in the Y direction (as shown by the periodic structures disposed therein). Of the 8 working zones 222, in any given orientation (A or B), 4 of the working zones 222' are printed in a first layer (represented by cross hatching) while 4 of the working zones 222" are printed in a second layer (not represented by cross hatching). The orientation of the working zones may be described in a variety of ways. For example, the working zones 222 may be distributed into four groups 224A-D that form the four corners of the square shaped mark 220. Each of these groups 224A-D is equally represented by working zones formed on different layers and in different direction. That is, each group includes four different working zones, as for example, working zones 222A', 222A", 222B' and 222B".

The working zones 222 may also be distributed into four groups 224E-H, each of which represents an "X"-configured mark (albeit offset). In this case, the "X"-configured mark is formed by the corners of a 3 by 3 working zone group. Of the four groups, two of them determine overlay in the X-direction and two of them determine overlay in the Y direction. For example, working group 224E and F, which include diagonally opposed and spatially offset working zones 222B' & 222B", determine overlay in the Y-direction. Furthermore, working group 224G and H, which include diagonally opposed and spatially offset working zones 222A' & 222A", determine overlay in the X-direction.

Figure 15:
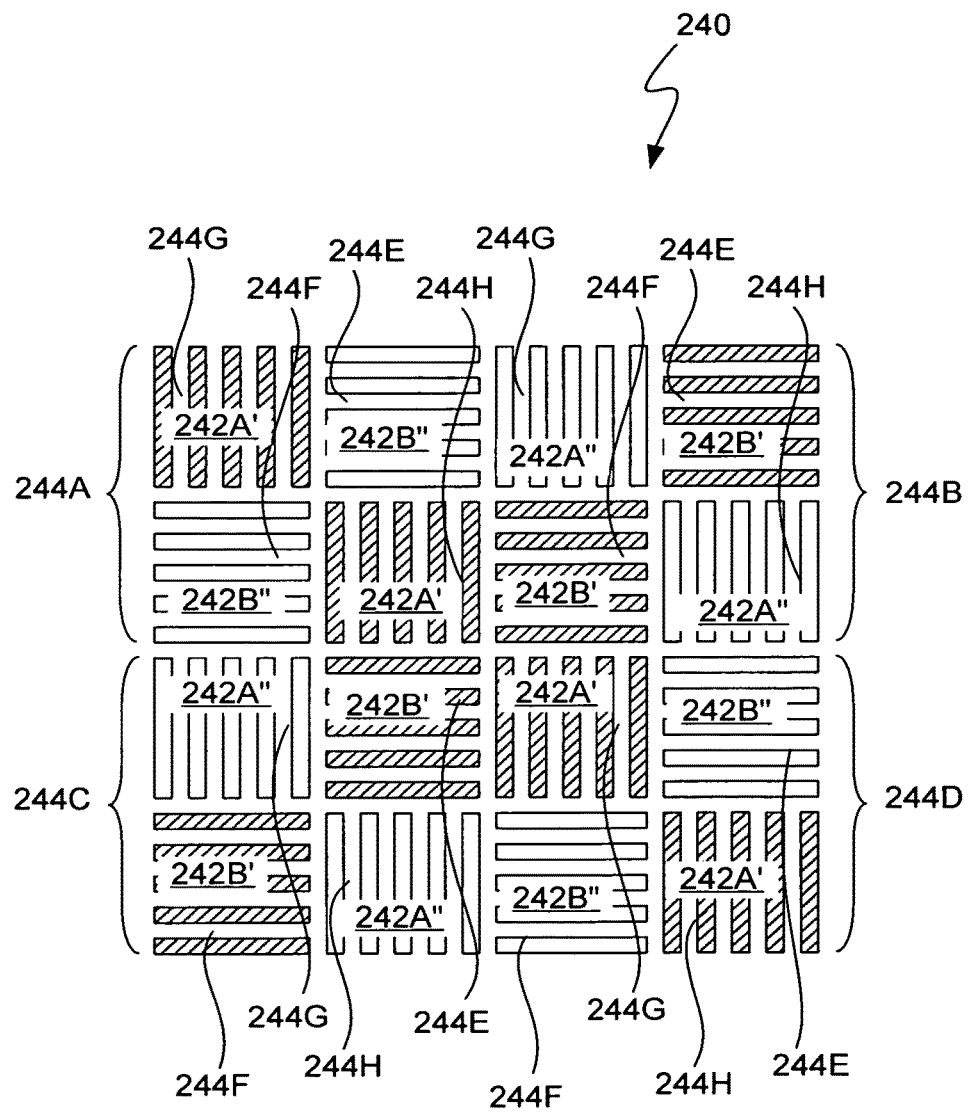
FIG. 15 is a top plan view of an overlay mark, in accordance with an alternate embodiment of the present invention.

FIG. 15 is a top plan view of an overlay mark 240, in accordance with an alternate embodiment of the present invention. By way of example, overlay mark 240 may generally correspond to the overlay mark shown in FIG. 14. Like the overlay mark of FIG. 13, overlay mark 240 is configured to measure overlay in two separate directions. As such, mark 240 obviates the need to have one mark for each direction in which overlay needs to be measured. Overlay mark 240 is shown in a configuration that results when the tested layers of a wafer are in perfect alignment.

The overlay mark 240 includes a plurality of working zones 242 for determining the registration error between two wafer layers in two different directions. In the illustrated embodiment, the overlay mark 240 includes sixteen square shaped working zones 242, which are configured to substantially fill its perimeter. Each of the working zones 242 includes a periodic structure of coarsely segmented lines. Although not shown, it should be appreciated that in some embodiments the coarsely segmented lines may be formed by a plurality of finely segmented elements.

Of the 16 working zones, 8 of the working zones 242A are oriented in the X direction and 8 of the working zones 242B are oriented in the Y direction (as shown by the periodic structures disposed therein). Of the 8 working zones 242, in any given orientation (A or B), 4 of the working zones 242' are printed in a first layer (represented by cross hatching) while 4 of the working zones 242" are printed in a second layer (not represented by cross hatching). The orientation of the working zones may be described in a variety of ways. For example, the working zones 242 may be distributed into four groups 244A-D that form the four corners of the square shaped mark 240. The groups that are opposed at vertical angles are identical, i.e., the working zones therein are oriented the same way. Of the four working zones in each group 244A-D, two of them represent the same layer and direction, and two of them represent a different same layer and direction. The working zones that are opposed at vertical angles to one another in these groups are identical. i.e., they represent the same layer and direction. For example, groups 244A & D include opposed working zones 242A' and opposed working zones 242B", and groups 244B & C include opposed working zones 242B' and opposed working zones 242A".

The working zones 242 may also be distributed into four groups 244E-H, each of which represents an "X"-configured mark (albeit offset). In this case, the "X"-configured mark is formed by the corners of a 3 by 3 working zone group. Of the four groups, two of them determine overlay in the X-direction and two of them determine overlay in the Y direction. For example, working group 244E and F, which include opposing working zones 242B'& 242'B, determine overlay in the Y-direction. Furthermore, working group 244G and H, which include opposing working zones 242A'& 242A", determine overlay in the X-direction.

Figure 16:
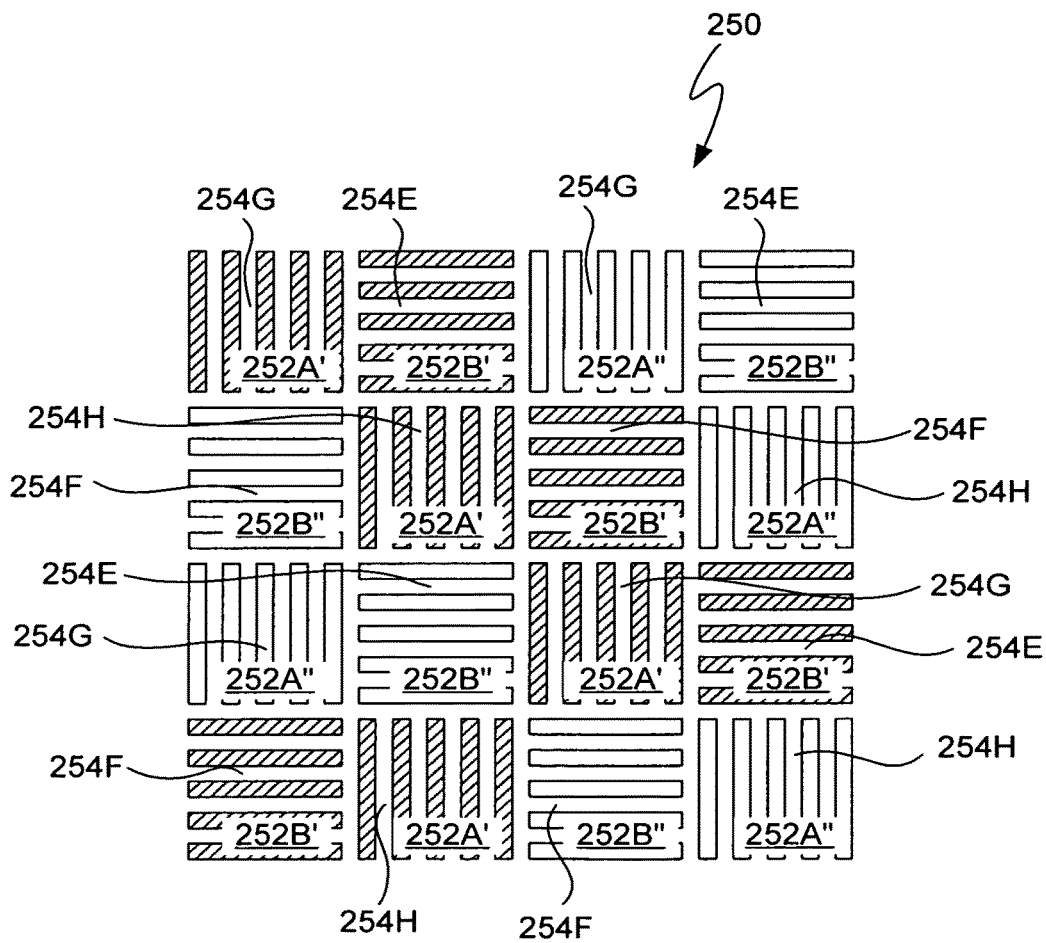
FIG. 16 is a top plan view of an overlay mark, in accordance with an alternate embodiment of the present invention.

FIG. 16 is a top plan view of an overlay mark 250, in accordance with an alternate embodiment of the present invention. By way of example, overlay mark 250 may generally correspond to the overlay mark shown in FIG. 13. Like the overlay mark of FIG. 14, overlay mark 250 is configured to measure overlay in two separate directions. As such, mark 250 obviates the need to have one mark for each direction in which overlay needs to be measured. Overlay mark 250 is shown in a configuration that results when the tested layers of a wafer are in perfect alignment.

The overlay mark 250 includes a plurality of working zones 252 for determining the registration error between two wafer layers in two different directions. In the illustrated embodiment, the overlay mark 250 includes sixteen square shaped working zones 252, which are configured to substantially fill its perimeter. Each of the working zones 252 includes a periodic structure of coarsely segmented lines. Although not shown, it should be appreciated that in some embodiments the coarsely segmented lines may be formed by finely segmented elements.

Of the 16 working zones, 8 of the working zones 252A are oriented in the X direction and 8 of the working zones 252B are oriented in the Y direction (as shown by the periodic structures disposed therein). Of the 8 working zones 252, in any given orientation (A or B), 4 of the working zones 252' are printed in a first layer (represented by cross hatching) while 4 of the working zones 252" are printed in a second layer (not represented by cross hatching). As shown, the working zones 252 may be distributed into four groups 254E-H, each of which represents an "X"-configured mark (albeit offset). In this case, the "X"-configured mark is formed by the corners of a 3 by 3 working zone group. Of the four groups, two of them determine overlay in the X-direction and two of them determine overlay in the Y direction. For example, working group 254E and F, which include opposing working zones 252B'& 252B", determine overlay in the Y-direction. Furthermore, working group 254G and H, which include opposing working zones 252A'& 252A", determine overlay in the X-direction.

Figure 17:
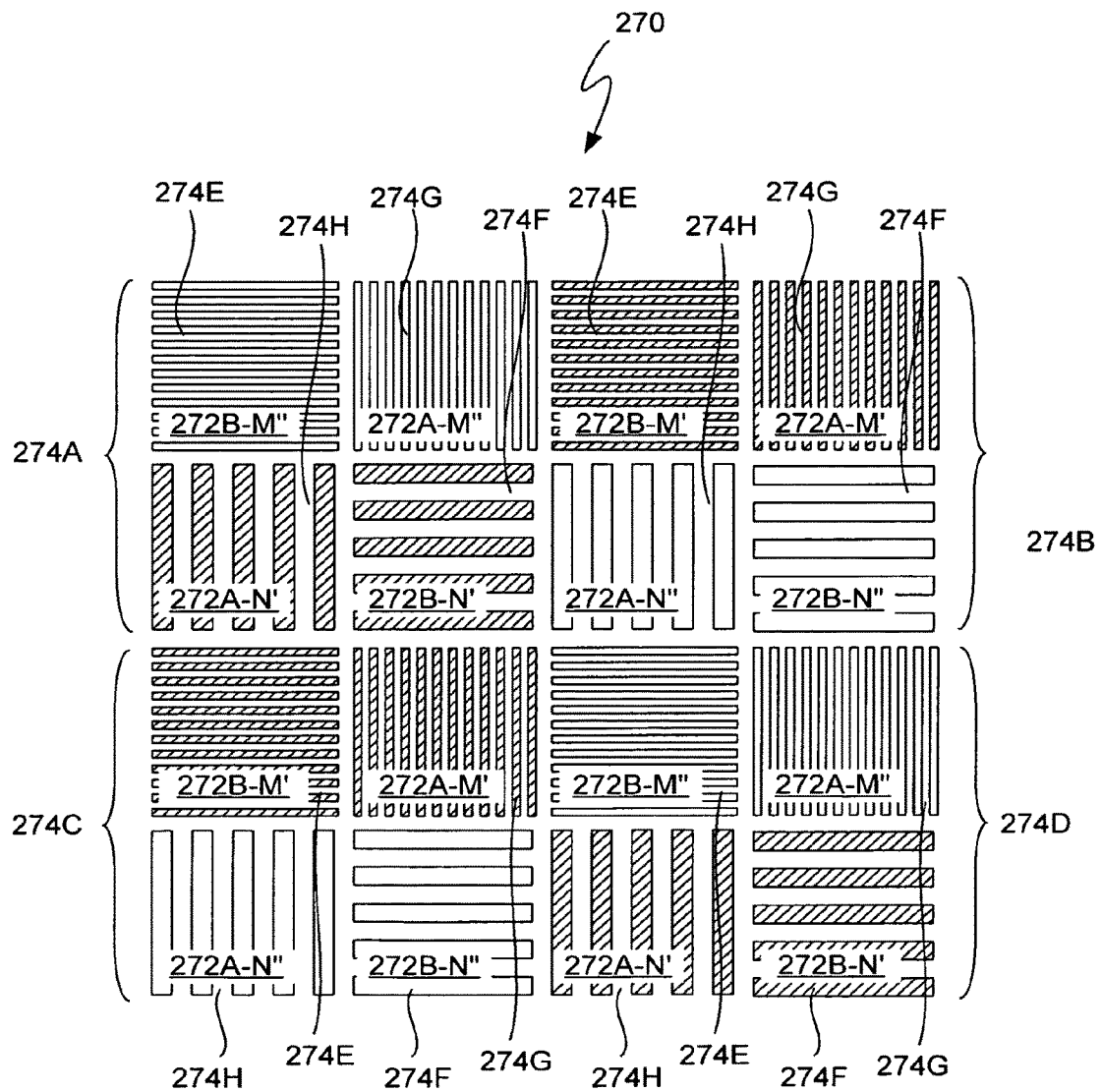
FIG. 17 is a top plan view of an overlay mark, in accordance with an alternate embodiment of the present invention.

FIG. 17 is a top plan view of an overlay mark 270, in accordance with an alternate embodiment of the present invention. By way of example, overlay mark 270 may generally correspond to the overlay mark shown in FIG. 13. Like the overlay mark of FIG. 14, overlay mark 270 is configured to measure overlay in two separate directions. As such, mark 270 obviates the need to have one mark for each direction in which overlay needs to be measured. Overlay mark 270 is shown in a configuration that results when the tested layers of a wafer are in perfect alignment.

The overlay mark 270 includes a plurality of working zones 272 for determining the registration error between two wafer layers in two different directions. In the illustrated embodiment, the overlay mark 270 includes sixteen square shaped working zones 272, which are configured to substantially fill its perimeter. Each of the working zones 272 includes a periodic structure of coarsely segmented lines. Although not shown, it should be appreciated that in some embodiments the coarsely segmented lines may be formed by finely segmented elements.

Of the 16 working zones, 8 of the working zones 272A are oriented in the X direction and 8 of the working zones 272B are oriented in the Y direction (as shown by the periodic structures disposed therein). Of the 8 working zones 272, in any given orientation (A or B), 4 of the working zones 272' are printed in a first layer (represented by cross hatching) while 4 of the working zones 272" are printed in a second layer (not represented by cross hatching). Furthermore, of the 8 working zones 272, in any given orientation (A or B), 4 of the working zones 272 have a periodic structure M with a first period (represented by thinner lines) while 4 of the working zones 272 have a periodic structure N with a second period that is different than the first period (represented by wider lines).

The orientation of the working zones may be described in a variety of ways. For example, the working zones 272 may be distributed into four groups 274A-D that form the four corners of the square shaped mark 270. The groups that are opposed at vertical angles are identical, i.e., the working zones therein are oriented the same way. Each of these groups 274A-D includes four different working zones, which may represent different combinations of layers, directions or period. The working zones that are opposed at vertical angles to one another in these groups represent the same direction, but different layers and periods. For example, groups 272A & D include working zone 272A-M' that is opposed to working zone 272B-N' and working zone 272A-M" that is opposed to working zone 272B-N", and groups 272B & C include working zone 272B-M' that is opposed to working zone 272A-N' and working zone 272B-M" is opposed to working zone 272A-N".

The working zones 272 may also be distributed into four groups 274E-H, each of which represents an "X"-configured mark (albeit offset). In this case, the "X"-configured mark is formed by the corners of a 3 by 3 working zone group. Of the four groups, two of them determine overlay in the X-direction and two of them determine overlay in the Y direction. Furthermore, two of them represent a first period and two of them represent a second period. For example, working group 274E, which includes opposing working zones 272B-M' & 272B-M", has a first period that determines overlay in the Y-direction, and working group 274F, which includes opposing working zones 272B-N' & 272B-N", has a second period that determines overlay in the Y-direction. Furthermore, working group 274G, which include opposing working zones 272A-M' & 272A-M", has a first period that determines overlay in the X-direction, and working group 274H, which include opposing working zones 272A-N' & 272A-N", has a second period that determines overlay in the X-direction.

As should be appreciated, this configuration can result in improved process robustness and/or improved contrast for one of the two grating periods, allowing selection of the optimized period and or line width for a specific process.

Figure 18:
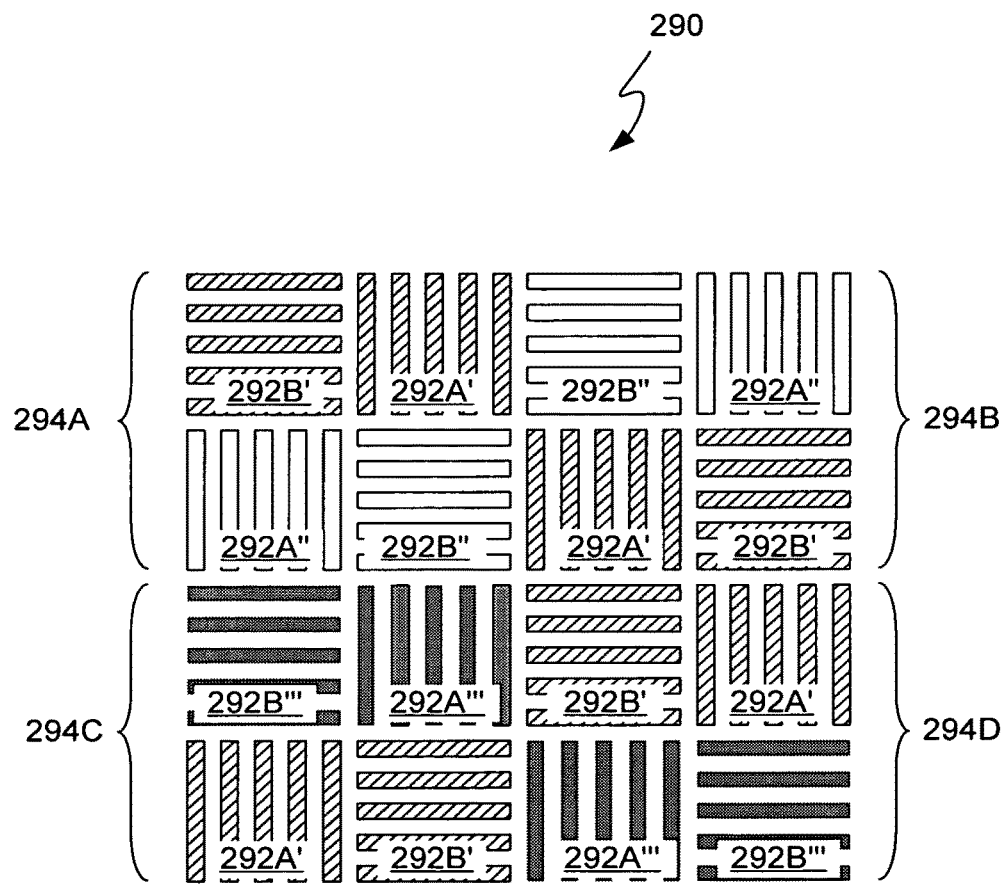
FIG. 18 is a top plan view of an overlay mark, in accordance with an alternate embodiment of the present invention.

FIG. 18 is a top plan view of an overlay mark 290, in accordance with an alternate embodiment of the present invention. By way of example, overlay mark 290 may generally correspond to the overlay mark shown in FIG. 13. Like the overlay mark of FIG. 14, overlay mark 290 is configured to measure overlay in two separate directions. As such, mark 290 obviates the need to have one mark for each direction in which overlay needs to be measured. Unlike the overlay mark of FIG. 13, overlay mark 290 is also configured to determine the relative shift between three successive layers of a wafer or between three separately generated patterns on a single layer of a wafer. For ease of discussion, the overlay mark 290 will be described in context of measuring overlay between different layers of a substrate. It should be noted, however, that the overlay mark in this figure may also be used to measure two or more separately generated patterns on a single layer of a substrate. Overlay mark 290 is shown in a configuration that results when the tested layers of a wafer are in perfect alignment.

The overlay mark 290 includes a plurality of working zones 292 for determining the registration error between three wafer layers in two different directions. In the illustrated embodiment, the overlay mark 290 includes sixteen square shaped working zones 292, which are configured to substantially fill its perimeter. Each of the working zones 292 includes a periodic structure of coarsely segmented lines. Although not shown, it should be appreciated that in some embodiments the coarsely segmented lines may be formed by finely segmented elements.

Of the 16 working zones 292, 8 of the working zones 292A are oriented in the X direction and 8 of the working zones 292B are oriented in the Y direction (as shown by the periodic structures disposed therein). Furthermore, 8 of the working zones 292' are printed in a first layer (represented by cross hatching), 4 of the working zones 292" are printed in a second layer (not represented by cross hatching), and 4 of the working zones 292"' are printed in a third layer (represented by fill). In this particular embodiment, the first layer (also represented by a single prime) is disposed over the second layer (also represented by a double prime) and the second layer is disposed over the third layer (also represented by a triple prime). By way of example, the first layer may represent a resist layer, the second layer may represent a first metal layer, and the third layer may represent a second metal layer.

It should be noted that the above configuration may be widely varied. For example, of the 8 working zones in any given orientation (A or B), 2 may be printed in a first layer, while each additional pair of gratings may be printed in up to any of 3 previous layers.

All of the overlay marks described above are configured to at least balance non-uniformities caused by the metrology tool (e.g., aberrations and illumination) and/or by the process (e.g., dishing and erosion). For example, some of the marks may be configured to reduce the impact of radial variations while others may be configured to reduce the impact of axial variations on the overlay measurements.

Figure 19:
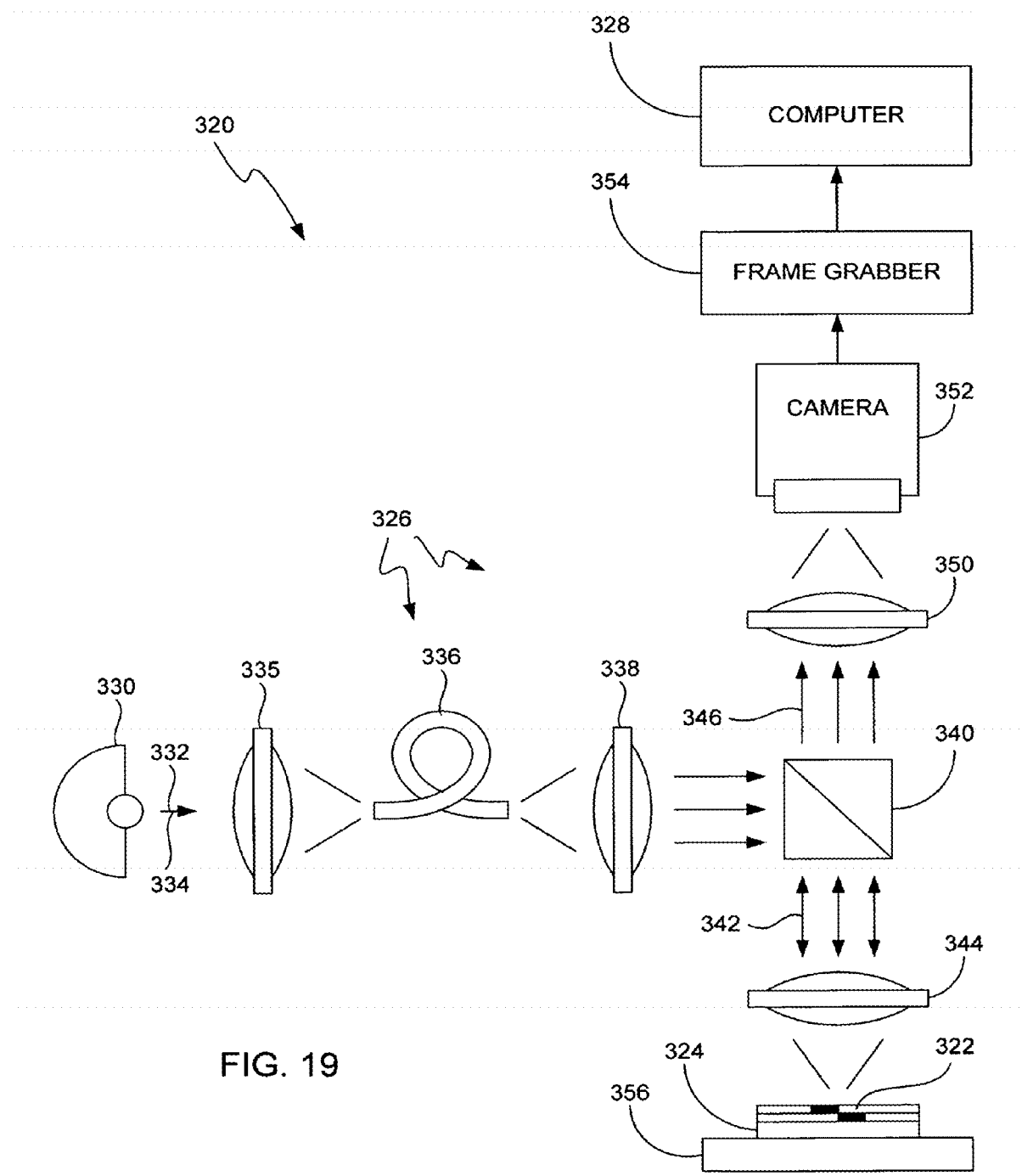
FIG. 19 is a simplified diagram of an overlay measurement system, in accordance with one embodiment of the present invention.

FIG. 19 is a simplified diagram of an overlay measurement system or metrology tool 320 that may be used to measure overlay in any of the marks described above via imaging. Imaging is a very developed technology with large user acceptance, and components that are readily available to the user. As is generally well known, imaging is an effective way to collect a large amount of information at any one time. That is, all points within the mark may be measured simultaneously. Furthermore, imaging allows a user to see what is actually being measured on the wafer. The dimensions of various components are exaggerated to better illustrate this embodiment. The overlay measurement system 320 is arranged to determine overlay error via one or more overlay targets 322 disposed on a wafer 324. In most cases, the overlay targets 322 are positioned within the scribe lines of the wafer 324. As is generally well known, scribe lines are the areas of the wafer used for sawing and dicing the wafer into a plurality of dies. It should be noted, however, that this is not a limitation and that the position of the targets may vary according to the specific needs of each device design. As shown, the overlay measurement system 320 includes an optical assembly 326 and a computer 328. The optical assembly 326 is generally arranged to capture the images of the overlay target 322. The computer, on the other hand, is generally arranged to calculate the relative displacement of the elements of the overlay target from the captured images.

In the illustrated embodiment, the optical assembly 326 includes a light source 330 (e.g., incoherent or coherent, although incoherent is generally preferred) arranged to emit light 332 along a first path 334. The light 332 is made incident on a first lens 335, which focuses the light 332 onto a fiber optic line 336 configured to pass the light 332 there through. When the light 332 emerges from fiber optic line 336, it then passes through a second lens 338, which is arranged to collimate the light 332. The collimated light 332 then continues on its path until it reaches a beam splitter cube 340, which is arranged to direct the collimated light onto a path 342. The collimated light 332 continuing along path 342 is made incident on an objective lens 344, which focuses the light 332 onto the wafer 324.

The light 332, which reflects off of the wafer 324, is then collected by the objective lens 344. As should be appreciated, the reflected light 332 that is collected by the objective lens 344 generally contains an image of a portion of the wafer 324, as for example, the image of the overlay target 322. When the light 332 leaves the objective 344, it continues along path 342 (backwards) until it reaches the beam splitter cube 340. In general, the objective lens 344 manipulates the collected light in a manner that is optically reverse in relation to how the incident light was manipulated. That is, the objective lens 344 re-collimates the light 332 and directs the light 332 towards the beam splitter cube 340. The beam splitter cube 340 is arranged to direct the light 332 onto a path 346. The light 332 continuing on path 346 is then collected by a tube lens 350, which focuses the light 332 onto a camera 352 that records the image of the wafer 324, and more particularly the image of the target 322. By way of example, the camera 352 may be a charge couple device (CCD), a two-dimensional CCD, or linear CCD array. In most cases, the camera 352 transforms the recorded image into electrical signals, which can be used by, and which are sent to the computer 328. After receiving the electrical signals, the computer 328 performs analysis algorithms that calculate the overlay error of the image. Analysis algorithms will be described in greater detail below.

The system 320 further includes a frame grabber 354 that works with the computer 328 and the camera 352 to grab images from the wafer 324. Although the frame grabber 354 is shown as a separate component, it should be noted that the frame grabber 354 may be part of the computer 328 and/or part of the camera 352. The frame grabber 354 typically has two functions—target acquisition and image grab. During target acquisition, the frame grabber 354 and computer 328 cooperate with a wafer stage 356 to place the target in focus and to position the target as closes as possible to the center of the field of view (FOV) of the metrology tool. In most cases, the frame grabber grabs a plurality of images (e.g., not the images used to measure overlay) and the stage moves the wafer between these grabs until the target is correctly positioned in the X, Y and Z directions. As should be appreciated, the X&Y directions generally correspond to the field of view (FOV) while the Z direction generally corresponds to the focus. Once the frame grabber determines the correct position of the target, the second of these two functions is implemented (e.g., image grab). During image grab, the frame grabber 354 makes a final grab or grabs so as to capture and store the correctly positioned target images, i.e., the images that are used to determine overlay.

After grabbing the images, information must be extracted from the grabbed images to determine the registration error. The extracted information may be digital information or in waveforms. Various algorithms may then be used to determine the registration error between various layers of a semiconductor wafer. For example, a frequency domain based approach, a space domain based approach, Fourier transform algorithms, zero-crossing detection, correlation and cross-correlation algorithms and others may be used.

Algorithms proposed for determining overlay via the marks described herein (e.g., marks that contain periodic structures) can generally be divided into a few groups. For instance, one group may relate to phase retrieval based analysis. Phase retrieval based analysis, which is often referred to as frequency domain based approaches, typically involves creating one dimensional signals by collapsing each of the working zones by summing pixels along the lines of the periodic structure. Examples of phase retrieval algorithms that may be used are described in U.S. Pat. No. 6,023,338 issued to Bareket, U.S. patent application Ser. No. 09/603,120 filed on Jun. 22, 2000, and U.S. patent application Ser. No. 09/654,318 filed on Sep. 1, 2000, all of which are incorporated herein by reference.

Yet another phase retrieval algorithm that may be used is described in U.S. application Ser. No. 09/697,025 filed on Oct. 26, 2000, which is also incorporated herein by reference. The phase retrieval algorithm disclosed therein decomposes signals into a set of harmonics of the basic signal frequency. Quantitative comparison of different harmonics' amplitudes and phases provide important information concerning signals' symmetry and spectral content. In particular, the phase difference between the 1st and 2nd or higher harmonics of the same signal (calibrated with their amplitudes) measures the degree of the signal asymmetry. The major contributions to such asymmetry come from the optical misalignment and illumination asymmetry in the metrology tool (tool induced shifts), as well as process induced structural features (wafer induced shifts). Comparing this misregistration between the phases of the 1st and the 2nd harmonics for the signals acquired from different parts of the field of view on the same process layer may provide independent information about optical aberrations of the metrology tool. Finally, comparing these misregistrations from measurements at a given orientation with those obtained after rotating the wafer 180 degrees allows separation of the tool induced and wafer induced shifts due to asymmetry.

Yet another phase retrieval algorithm that may be used is Wavelet analysis. Wavelet analysis is somewhat similar to that described in the section above, however, now a dynamic window is moved across the one dimensional signal and the phase estimation is carried out in a more localized way. This is particularly of interest with use in the case of a chirped periodic structure.

Another group may relate to intensity correlation based methods. In this approach the centers of symmetry for each process layer is found separately by calculating the cross covariance of one signal with the reversed signal from the opposite part of the mark, from the same process layer. This technique is similar to techniques used today with regards to box in box targets.

The above techniques are brought by way of example and have been tested and demonstrated good performance. Other alternative algorithmic methods for calculation of overlay include other variations of auto & cross correlation techniques, error correlation techniques, error minimization techniques, such as minimization of absolute difference, minimization of the square of the difference, threshold based techniques including zero cross detection, and peak detection. There are also dynamic programming algorithms which can be used for searching for the optimal matching between two one-dimensional patterns. As mentioned above, the analysis algorithms and approaches may be utilized with respect to all of the various overlay marks described in the previous section.

Importantly, it should be noted that the above diagram and description thereof is not a limitation and that the overlay image system may be embodied in many other forms. For example, it is contemplated that the overlay measurement tool may be any of a number of suitable and known imaging or metrology tools arranged for resolving the critical aspects of overlay marks formed on the surface of the wafer. By way of example, overlay measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, grab, double grab, single grab coherence probe microscopy (CPM) and double grab CPM methods. These types of systems, among others, are readily available commercially. By way of example, single and multiple image methods may be readily available from KLA-Tencor of San Jose, Calif.

FIG. 20A is a simplified flow diagram illustrating a method 360 of calculating overlay, in accordance with one embodiment of the present invention. For ease of discussion, this method will be described via the mark shown in FIG. 9. This mark is now shown next to the flow diagram in FIG. 20B. The method 360 begins at step 362 where the working zones are selected from the captured image. By way example, for calculating X-overlay, working zones 132 E-H may be selected, and for calculating Y-overlay, working zones 132 A-D may be selected. After selecting the working zones, the process flow proceeds to step 364 where representative signals are formed for each of the selected working zones. This may be accomplished by collapsing the 2D images into 1D signals by averaging over X for Y-overlay calculations and by averaging over Y for X-overlay calculations. By way of example, FIG. 20C illustrates a first collapsed 1D signal for working zone 132A and a second collapsed 1D signal for working zone 132B. It should be noted, that FIG. 20C is representative of any of the pairs of juxtaposed working zones. After forming the signals, the process flow proceeds to step 366 where the overlay is determined by comparing the signals.

In one embodiment, this is accomplished via a covariance-based overlay algorithm, which is based upon calculation of the cross-correlation between the patterns belonging to the same process layers. As a result, the centers of symmetry for both layers are found, and their misregistration is essentially the overlay. The flowchart of this algorithm is shown in FIG. 21.

In another embodiment, this is accomplished via a Fourier Decomposition overlay algorithm, which utilizes the periodical character of the grating structures. This algorithm decomposes signals acquired from the target patterns to a series of Fourier harmonics. Comparison of phases between the same order harmonics from different process layers calibrated to nominal pitch of the grating patterns serves then as a basis for overlay calculation. Accordingly, this algorithm provides several independent overlay results—one for each Fourier order. The flowchart of this algorithm is shown in FIG. 22.

FIG. 21 is a flow diagram illustrating a method 370 of calculating overlay using Covariance, in accordance with one embodiment of the present invention. By way of example method 370 may generally correspond to step 366 of FIG. 20A. The method 370 begins at step 372 where the signal cross-correlation is calculated. This is typically done with respect to opposing working zones. With regards to the mark of FIG. 9, the signal cross-correlation is calculated for working zone pairs 132A vs. reversed 132D, 132B vs. reversed 132C, 132E vs. reversed 132H, and 132F vs. reversed 132G. After calculating the signal cross correlation, the process flow proceeds to step 374 where the positions of cross-correlation maxima (sub pixel) are found. This is typically done for both of the layers, i.e., layer 1, which is represented by cross hatching, and layer 2, which is represented with no cross hatching. After finding the positions of cross correlation maxima, the process flow proceeds to step 376 where the overlay is determined by calculating the difference between the positions of cross correlation maxima. For example, the difference between the cross correlation maxima of working zones 132E&H (layer 1)—working zones 132 F&G (layer 2) determines the misregistration in the X-direction. In addition, the difference between the cross correlation maxima of working zones 132A&D (layer 1)—working zones 132 B&C (layer 2) determines the misregistration in the Y-direction.

FIG. 22 is a flow diagram illustrating a method 380 of calculating overlay using Fourier Decomposition, in accordance with one embodiment of the present invention. By way of example method 380 may generally correspond to step 366 of FIG. 20A. The method 380 begins at step 382 where the signals are fitted to a Fourier series and their phases are extracted. After fitting and extracting, the process flow proceeds to step 384 where the phase difference between juxtaposed working zones is found. For example, in the Y direction, the phase difference is found between working zones 132A and 132B, as well as, between working zones 132C and 132D. In addition, in the X direction, the phase difference is found between working zones 132E and 132F, as well as, between working zones 132G and 132H. After finding the phase difference, the process flow proceeds to step 386 where the overlay is determined by calculating the difference between the phase differences of the previous step for a given direction. For example, the average of the difference between the phase difference of working zones 132E&F and the phase difference of working zones 132 G&H determines the misregistration in the X-direction. In addition, the average of the difference between the phase difference of working zones 132A&B and the phase difference of working zones 132 C&D determines the misregistration in the Y-direction. In order to obtain data that corresponds to positions of the layers, the phase difference is multiplied by the pitch and divided by 2□.

In summary, a method of designing overlay marks in accordance with the principles set forth above will now be described.

Figure 23:
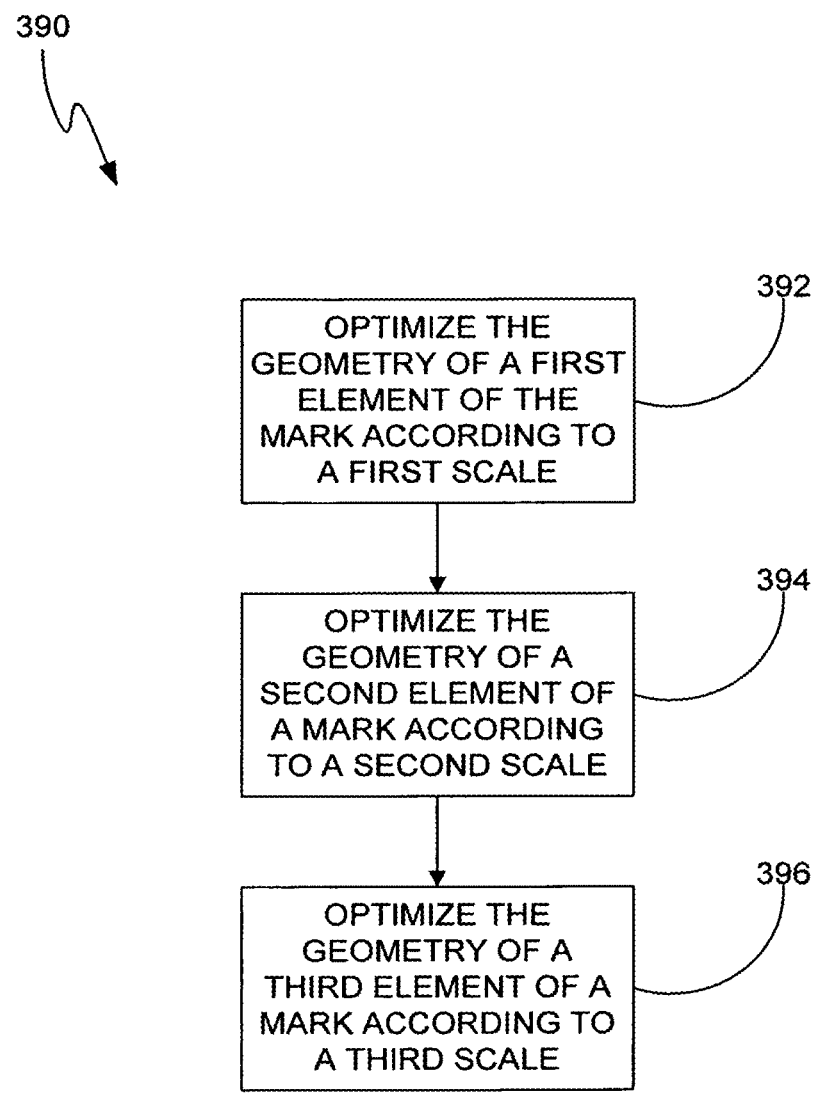
FIG. 23 is a flow diagram of a method of designing an overlay mark, in accordance with one embodiment of the present invention.

FIG. 23 is a flow diagram illustrating a method 390 of designing an overlay mark, in accordance with one embodiment of the present invention. By way of example, the overlay mark may generally correspond to any of the overlay marks described above. The overlay mark is generally provided to determine the relative shift between two or more successive layers of a substrate or between two or more separately generated patterns on a single layer of a substrate. In accordance with one embodiment of the present invention, the overlay mark comprises a plurality of elements that form the pattern of the overlay mark. Each of these elements may be configured to contain information for measuring overlay in a more precise or accurate manner. By way of example, the elements may generally correspond to the working zones, periodic structures of coarsely segmented elements and finely segmented elements.

The method 390 begins at step 392 where the geometry of a first element of the mark is optimized according to a first scale. This is typically accomplished by identifying the upper and lower limits of the first scale and fine tuning the geometry of the first geometry between the upper and lower limits. In one embodiment, the first scale corresponds to the metrology kernel scale, which defines the boundaries of the regions that contain information about the two different layers or patterns between which overlay is to be measured. The metrology kernel scale has characteristic dimensions in the 10's of microns. For example, the metrology kernel scale may range from about 4 microns to about 10 microns, and more particularly from about 5 microns to about 10 microns.

In most cases, the metrology kernel scale is based on metrology tool limitations, process issues and circuit design criteria. Metrology tool limitations generally refers to limitations associated with the metrology tool (both for a line of tools and a specific tool within the line). For example, metrology tool limitations may include the size and shape of the field of view of the metrology tool used to measure overlay, the minimum amount of target area needed to effectively measure overlay and asymmetrical aberration and illumination field distributions created by the components of the metrology tool. Process robustness issues generally refer to restrictions associated with the robustness of the process, as for example, etching, deposition, chemical-mechanical polishing (CMP) and the like. For example, there may be parts of the mark that are more susceptible to process damage or process variation and thus they should be avoided. Circuit design criteria generally refers to the rules used to design the overall circuit pattern. For example, the circuit design rules may include scribe line limitations that pertain to the overlay mark budget, i.e., the mark is typically positioned inside the scribe line of the wafer. The scribe line is the place on the wafer where the wafer separated into a plurality of dies via sawing or dicing.

Once the first scale is identified, the geometry of the first element, which generally contains information relating to the layers or patterns between which overlay is measured, may be fine-tuned to find a mark layout that works best within this scale. In one embodiment, the first element corresponds to working zones, which define the different layers or patterns of the overlay mark, and which represent the actual area of the overlay mark that is used for overlay measurements. The term "geometry" generally refers to the size, shape, and/or distribution of the first element, i.e., the working zones. In one embodiment, fine-tuning is implemented by defining the perimeter of the mark (e.g., FOV) and dividing the mark into a plurality of working zones that are configured to minimize the impact of asymmetries on the measurement of overlay. By way of example, the working zones may be configured to minimize the impact of optical aberrations and illuminations on tool induced shifts in the resultant overlay measurement. In addition, the working zones may be configured to minimize the impact of process variations on wafer induced shifts in the resultant overlay measurement.

After optimizing the geometry of the first element, the process flow proceeds to step 394 where the geometry of a second element of the mark is optimized according to a second scale. This is typically accomplished by identifying the upper and lower limits of the second scale and fine tuning the geometry of the second element between the upper and lower limits. In one embodiment, the second scale corresponds to the image resolution scale, which defines the boundaries between structures within a given process layer. The image resolution scale has characteristic dimensions in the 1 micron range. For example, the image resolution scale may range from about 0.3 microns to about 2 microns, and more particularly from about 0.5 microns to about 1 micron.

In most cases, the image resolution scale is based on metrology tool limitations and process robustness issues. Metrology tool limitations generally refers to limitations associated with the metrology tool (both for a line of tools and a specific tool within the line). For example, metrology tool limitations may include the image resolution of the tool, i.e., the ability to capture an image, the algorithms used by the tool to calculate the overlay error and the aberration and illumination field distributions of the tool. Process robustness issues generally refer to restrictions that are created by the materials and processes that are used to form the layers and patterns on the wafer, as for example, etching, deposition, chemical-mechanical polishing (CMP) and the like. For example, for specific processes, such as aluminum coated, chemically mechanically polished tungsten, it is advantageous for the geometry of the second element to be one micron or less in order to diminish the impact of asymmetries resultant from the polishing and aluminum deposition processes. In other cases, where the metal grain size is large, it may be preferable that the lines be larger than 1 micron, as for example, up to two microns.

Once the second scale is identified, the geometry of the second element, which generally contains the actual spatial information regarding the relative positions of the mark components that is encoded and transferred to the metrology tool, may be fine-tuned to find a mark layout that works best within this scale. In one embodiment, the second element corresponds to a periodic structure of coarsely segmented lines that is positioned within each of the working zones of the first element. The term "geometry" generally refers to the size, shape, and/or distribution of the second element i.e., the periodic structure of coarsely segmented lines (e.g., linewidths and spacings). In one embodiment, the periodic structures via the coarsely segmented lines are configured to enhance the measurement of overlay by balancing the image resolution of the tool with the process.

After optimizing the geometry of the second element, the process flow proceeds to step 396 where the geometry of a third element of the mark is optimized according to a third scale. This is typically accomplished by identifying the upper and lower limits of the third scale and fine tuning the geometry of the third element between the upper and lower limits. In one embodiment, the third scale corresponds to the lithography resolution scale, which defines the boundaries of sub-structures within a given structure. The lithography resolution scale has characteristic dimensions in the 0.1 microns range. For example, the lithography resolution scale may range from about 0.01 microns to about 0.5 microns, and more particularly from about 0.05 microns to about 0.18 microns.

In most cases, the lithography resolution scale is based on circuit design rules, process robustness issues and metrology tool limitations. Circuit design rules generally refer to the rules used to design the overall circuit pattern. For example, the circuit design rules may include the geometry of the circuit devices (e.g., feature size and density). Process robustness issues generally refer to restrictions that are created by the materials and processes that are used to form the layers and patterns on the wafer, as for example, etching, deposition, chemical-mechanical polishing (CMP) and the like. Metrology tool limitations generally refer to limitations associated with the metrology tool (both for a line of tools and a specific tool within the line). For example, metrology tool limitations may include contrast requirements of the tool, i.e., the ability to resolve the larger structures, which are comprised by the smaller sub-structures.

Once the third scale is identified, the geometry of the third element, which generally contains information reflective of the circuit structures themselves, may be fine-tuned to find a mark layout that works best within this scale. In one embodiment, the third element corresponds to the finely segmented elements that form the plurality of coarsely segmented lines of the periodic structures of the second element. The term "geometry" generally refers to the size, shape, and/or distribution of the third element, i.e., the finely segmented elements. In one embodiment, the finely segmented elements are configured to minimize the adverse effects of the process so as to improve the accuracy and precision of the overlay measurements. In another embodiment, the structure is optimized so as to minimize the difference in stepper PPE between the target and the actual device, as described previously in FIGS. 3-5.

While this invention has been described in terms of several preferred embodiments, there are alterations, permutations, and equivalents, which fall within the scope of this invention.

For example, although the invention has been described in terms of manufacturing semiconductor devices, it should be realized that the invention may also be suitable for manufacturing other types of devices such as microfabrication of optical or optoelectronic devices, microfabrication of magnetic storage media or magnetic storage read/write or input/output devices, microfabrication using lithographic patterning in general, to include photolithography down to 100 nm exposure wavelengths, extreme-ultraviolet lithography with wavelengths 10 nm to 100 nm. Xrays lithography with wavelengths <10 nm, electron beam lithography, ion beam patterning, or mixed lithography using more than one of these methods.

In addition, besides supplying data for overlay measurements, periodic structure targets are capable of providing much additional information for target, stepper and metrology tool diagnostics (e.g., contrast, sharpness, graininess, acquisition quality and symmetry metrics). For example, comparison of overlay, precision, TIS, and TIS variability results obtained by Covariance and Fourier Decomposition methods can serve as one such instrument. Measurement of phase difference between different Fourier harmonics from the same signal gives important information concerning symmetry of the marks due to process imperfectness, aberrations or illumination problems. Performing the same analysis for the target rotated by 180° allows the separation of asymmetries on the wafer from those due to the metrology tool. Filling the whole FOV by target structures allows the selection of different working zones, thus providing information about variations within a single target and allowing additional optimization. Finally, grating targets provide an opportunity for simpler diagnostic of the target's tilt in FOV.

Furthermore, although the algorithms have been described as utilizing one dimensional arrays of information, it should be noted that they may also be applied to two dimensional arrays of information.

Moreover, although the marks herein have been described for measuring overlay, they may also be used for one or more of the following measurements or applications: CD, exposure monitoring, resist profile monitoring, focus monitoring, and the like.

It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. A metrology system for determining the overlay between at least two separately generated patterns on a single or successive layers of a substrate, the system comprising:
    an optical assembly for capturing images of a multidirectional overlay mark comprising:
        a first region having at least two separately generated working zones, that are juxtaposed relative to one another, and are configured to provide overlay information in a first direction, and each include a periodic structure comprised of a plurality of coarsely segmented elements positioned therein,
        a second region having at least two separately generated working zones, that are juxtaposed relative to one another, and are configured to provide overlay information in the first direction, and each include a periodic structure comprised of a plurality of coarsely segmented elements positioned therein,
        a third region having at least two separately generated working zones, that are juxtaposed relative to one another, and are configured to provide overlay information in a second direction that differs from the first direction, and each include a periodic structure comprised of a plurality of coarsely segmented elements positioned therein,
        a fourth region having at least two separately generated working zones, that are juxtaposed relative to one another, and are configured to provide overlay information in the second direction, and each include a periodic structure comprised of a plurality of coarsely segmented elements positioned therein,
        wherein the working zones of the first and second regions that were generated together are diagonally opposed and spatially offset relative to one another, and
        wherein the working zones of the third and fourth regions that were generated together are diagonally opposed and spatially offset relative to one another; and a computer for analyzing the captured images to determine whether the multidirectional overlay mark has an overlay error.

2. The system as recited in claim 1, wherein the first and second regions are positioned in an opposed relationship on opposite sides of a first axis of the multidirectional overlay mark and wherein the third and fourth regions are positioned in an opposed relationship on opposite sides of a second axis of the multidirectional overlay mark.

3. The system as recited in claim 2, wherein the first axis is a horizontal axis and wherein the second axis is a vertical axis.

4. The system as recited in claim 2, wherein the center of the first and second regions are aligned with one another on the second axis and wherein the center of the third and fourth regions are aligned with one another on the first axis.

5. The system as recited in claim 1 wherein the multidirectional overlay mark is configured for determining the overlay between three separately generated patterns on a single or successive layers of a substrate.

6. The system as recited in claim 1, wherein the first region is disposed above a horizontal axis of the multidirectional overlay mark, wherein the second region is disposed below the horizontal axis of the multidirectional overlay mark, wherein the third region is disposed to the left of a vertical axis of the multidirectional overlay mark, and wherein the fourth region is disposed to the right of the vertical axis of the multidirectional overlay mark.

7. The system as recited in claim 6, wherein the separately generated working zones include a first working zone generated via a first process and a second working zone generated via a second process, and wherein the first region includes the first working zone positioned on a first side and the second working zone positioned on a second side, the second region includes the second working zone positioned on the first side and the first working zone positioned on the second side, the third region includes the first working zone positioned on a first side and the second working zone positioned on a second side, and the fourth region includes the second working zone positioned on a first side and the first working zone positioned on a second side.

8. The system as recited in claim 1, the first and second regions lie crosswise relative to the third and fourth regions.

9. The system as recited in claim 1, wherein the arrangement of working zones in the first, second, third and fourth regions is rotational symmetric at 0, 90, 180, 270 and 360degrees about the center of the multidirectional overlay mark.

10. The system as recited in claim 9, wherein the arrangement of working zones between the first and second regions does not have reflection symmetry, and wherein the arrangement of working zones between the third and fourth regions does not have reflection symmetry.

11. The system as recited in claim 1, wherein each of the four regions includes three separately generated working zones.

12. A metrology system for determining the overlay between at least two separately generated patterns on a single or successive layers of a substrate, the system comprising:
    an optical assembly for capturing images of an overlay mark comprising:
        a first set of working zones being formed from a first process and having at least two working zones that are diagonally opposed and spatially offset relative to each other, each of the first set of working zones including a periodic structure comprising a plurality of coarsely segmented elements that are each formed from a plurality of finely segmented elements that are evenly divided over the entire coarsely segmented elements of the first set of working zones, and a second set of working zones being formed from a second process and having at least two working zones that are diagonally opposed and spatially offset relative to each other, each of the second set of working zones including a periodic structure comprising a plurality of coarsely segmented elements that are each formed from a plurality of finely segmented elements that are evenly divided over the entire coarsely segmented elements of the second set of working zones; and a computer for analyzing the captured images to determine whether the overlay mark has an overlay error.

13. The system of claim 12, wherein the coarsely segmented elements within each periodic structure have substantially the same size and shape and equal spacings.

14. The system of claim 12, wherein the finely segmented elements are etched or deposited vias.

15. The system of claim 12, wherein the finely segmented elements within each of the coarsely segmented elements have substantially the same size and shape and equal spacings.

16. A metrology system for determining the overlay between at least two separately generated patterns on a single or successive layers of a substrate, the system comprising:

an optical assembly for capturing images of a multidirectional overlay mark comprising:

a plurality of first periodic structures formed via a first process and having a first orientation and comprised of a plurality of coarsely segmented elements, wherein the first periodic structures comprise at least two working zones that are diagonally opposed and spatially offset relative to each other;

a plurality of second periodic structures formed via a second process and having the first orientation and comprised of a plurality of coarsely segmented elements, wherein the second periodic structures comprise at least two working zones that are diagonally opposed and spatially offset relative to each other;

a plurality of third periodic structures formed via the first process and having a second orientation and comprised of a plurality of coarsely segmented elements, wherein the third periodic structures comprise at least two working zones that are diagonally opposed and spatially offset relative to each other; and a plurality of fourth periodic structures formed via the second process and having the second orientation and comprised of a plurality of coarsely segmented elements, wherein the fourth periodic structures comprise at least two working zones that are diagonally opposed and spatially offset relative to each other, wherein each of the working zones of the first plurality of periodic structures is adjacent to one of the working zones of the second plurality of periodic structures, and wherein each of the working zones of the third plurality of periodic structures is adjacent to one of the working zones of the fourth plurality of periodic structures; and a computer for analyzing the captured images to determine whether the multidirectional overlay mark has an overlay error.

17. The system of claim 16, wherein at least one first periodic structure and at least one second periodic structure is positioned on a first side of a first axis of the overlay mark, and at least one first periodic structure and at least one second periodic structure is positioned on a second side of the first axis of the overlay mark, and wherein at least one third periodic structure and at least one fourth periodic structure is positioned on a first side of a second axis of the overlay mark, and at least one third periodic structure and at least one fourth periodic structure is positioned on a second side of the second axis of the overlay mark, the first and second axis being perpendicular to one another and intersecting at the center of the multidirectional overlay mark.

18. The system of claim 17, wherein the first and second periodic structures on opposing sides of the first axis are rotationally symmetric 180 degrees about the center of the multidirectional overlay mark, and wherein the third and fourth periodic structures on opposing sides of the second axis are rotationally symmetric 180 degrees about the center of the multidirectional overlay mark.

19. The system of claim 17, wherein the first and second periodic structures are aligned and juxtaposed next to each other, and wherein the third and fourth periodic structures are aligned and juxtaposed next to each other.

20. The system of claim 19, wherein the first periodic structures on opposing sides of the first axis are diagonally situated relative to each other, the second periodic structures on opposing sides of the first axis are diagonally situated relative to each other, the third periodic structures on opposing sides of the second axis are diagonally situated relative to each other, and the fourth periodic structures on opposing sides of the second axis are diagonally situated relative to each other.

21. A metrology system for determining the overlay between at least two separately generated patterns on a single or successive layers of a substrate, the system comprising:

an optical assembly for capturing images of a multidirectional overlay mark comprising:

a first set of working zones being formed from a first process, and each first set of working zones including a periodic structure of a plurality of elements that are spaced apart within a plurality of lines and configured to convey overlay information in a first direction and a second direction that differs from the first direction; and a second set of working zones being formed from a second process, and each second set of working zones including a periodic structure of a plurality of elements that are spaced apart within a plurality of lines and configured to convey overlay information in the first direction and the second direction, wherein the first set, of working zones and second set of working zones are diagonally opposed and spatially offset relative to one another, and wherein the elements are substantially distributed over an area of the overlay mark; and a computer for analyzing the captured images to determine whether the multidirectional overlay mark has an overlay error.

22. A system as recited in claim 21, wherein the configuration of the elements in each layer is designed to be rotationally symmetric at 0, 90, 180, 270, and 360 degrees around the center of the overlay mark when there is no overlay error.

23. A system as recited in claim 22, further comprising a center structure positioned in the center of the multidirectional overlay mark.

24. A system as recited in claim 21, wherein the area of the mark corresponds to a field of view of the metrology system.

25. A system recited in claim 21, wherein the multidirectional overlay mark further comprises:
a third set of working zones being formed from a third process, and including a periodic structure of a plurality of elements that are spaced apart within a plurality of lines and configured to convey overlay information in the first direction and the second direction; and
a fourth set of working zones being formed from a fourth process, and including a periodic structure of a plurality of elements that are spaced apart within a plurality of lines and configured to convey overlay information in the first direction and the second direction,
wherein the third set of working zones and fourth set of working zones are diagonally opposed and spatially offset relative to one another and
wherein the elements of the first, second, third, and fourth working zones are substantially distributed over an area of the multidirectional overlay mark.

26. A system as recited in claim 21, wherein the multidirectional overlay mark further comprises a plurality of sets of working zones formed by a plurality of other processes that differ from the first and second processes and are configured to provide overlay information in the first and second directions, wherein the plurality of working zones are each comprised of a plurality of segmented elements that are spaced apart within a plurality of lines and are each arranged in at least four working zones that are juxtaposed in relation to each other and wherein the plurality of working zones of the segmented elements each include pairs of working zones that lie crosswise to each other, wherein the plurality of working zones of the plurality of segmented element sets are distributed across an area of the multidirectional overlay mark.

27. A metrology system for determining the overlay between at least two separately generated patterns on a single or successive layers of a substrate, the system comprising:
an optical assembly for capturing images of a multidirectional overlay mark comprising:
a first quadrant having only two separately generated working zones, that are juxtaposed relative to one another, and are configured to provide overlay information in a first direction, and each include a periodic structure comprised of a plurality of coarsely segmented elements positioned therein, and that together substantially fill their quadrant,
a second quadrant having only two separately generated working zones, that are juxtaposed relative to one another, and are configured to provide overlay information in the first direction, and each include a periodic structure comprised of a plurality of coarsely segmented elements positioned therein, and that together substantially fill their quadrant,
a third quadrant having only two separately generated working zones, that are juxtaposed relative to one another, and are configured to provide overlay information in a second direction that differs from the first direction, and each include a periodic structure comprised of a plurality of coarsely segmented elements positioned therein, and that together substantially fill their quadrant, and
a fourth quadrant having only two separately generated working zones, that are juxtaposed relative to one another, and are configured to provide overlay information in the second direction, and each include a periodic structure comprised of a plurality of coarsely segmented elements positioned therein, and that together substantially fill their quadrant,
wherein each quadrant includes an inner working zone and an outer working zone, the inner working zone being positioned towards the center of the multidirectional overlay mark, the outer working zone being positioned toward the periphery of the multidirectional overlay mark,
wherein the coarsely segmented elements are finely segmented in order to control the contrast of the resultant image in the metrology system; and
a computer for analyzing the captured images to determine whether the multidirectional mark has an overlay error.

28. A metrology system for determining the overlay between at least two separately generated patterns on a single or successive layers of a substrate, the system comprising:
an optical assembly for capturing images of an overlay mark that is separated into four quadrants, each of the four quadrants including only two separately generated working zones that together substantially fill their quadrant, each of the working zones including a periodic structure comprised of a plurality of coarsely segmented elements positioned therein, the two separately generated working zones being juxtaposed relative to one another, and configured to provide overlay information in the same direction, each quadrant including an inner working zone and an outer working zone, the inner working zone being positioned towards the center of the overlay mark, the outer working zone being positioned towards the periphery of the overlay mark; and
a computer for analyzing the captured images to determine whether the overlay mark has an overlay error.

29. The system as recited in claim 28 wherein the working zones substantially fill the perimeter of the overlay mark.

30. The system as recited in claim 28 wherein the working zones are spatially separated from one another so that they do not overlap portions of an adjacent working zone.

31. The system as recited in claim rein the working zones are configured to diminish an impact of non-uniformities across the overlay mark on tool and wafer induced shifts.

32. The system as recited in claim 28 wherein the coarsely segmented elements are parallel lines.

33. The system as recited in claim 28 wherein the plurality of coarsely segmented elements are formed from a plurality of finely segmented elements.

34. The system as recited in claim 33 wherein the finely segmented elements are configured to provide shift information that more closely matches the relative shift between patterns of an integrated circuit formed on each of the two layers of the substrate.

35. The system as recited in claim 28 wherein the first direction corresponds to the X-direction and the second direction corresponds to the Y-direction.

36. The system as recited in claim 28 wherein the coarsely segmented elements located within juxtaposed pairs of working zones within each quadrant are aligned with one another.

37. The system as recited in claim 28 wherein the inner working zone is disposed on a first layer, and wherein the outer working zone is disposed on a second layer.

38. The system as recited in claim 37 wherein the first layer is disposed directly above or below the second layer.

39. The system as recited in claim 28 wherein within the quadrants, the working zones located closer to a center of the overlay mark were generated concurrently with one another and the working zones located further from the center of the overlay mark were generated concurrently with one another.

40. The system as recited in claim 28 wherein the overlay mark has a center and wherein the configuration of the working zones within each quadrant is rotationally symmetric at 0, 90, 180, 270 and 360 degrees around the center of the overlay mark.

41. The system as recited in claim 28 wherein the coarsely segmented lines are formed from a plurality of finely segmented elements configured to mimic one or more device features formed concurrently with the finely segmented elements, the finely segmented elements being symmetrically positioned within each of the coarsely segmented lines.

42. The system as recited in claim 28 wherein the working zones in each quadrant are configured to provide overlay information in the same direction.

43. The system as recited in claim 42 wherein the working zones in opposed quadrants provide overlay information in the same direction.

44. The system as recited in claim 28 wherein the working zones are square shaped.

45. The system as recited in claim 28 wherein the working zones are rectangular shaped.

46. The system as recited in claim 28 wherein the working zones are triangular shaped.

47. The system as recited in claim 28 wherein the working zones within each quadrant are separated by exclusion zones.

48. The system as recited in claim 28 wherein the working zones within each quadrant are adjacent to one another.

49. The system as recited in claim 28 wherein the center of the overlay mark includes a grating pattern.

50. The system as recited in claim 28 wherein the four quadrants include an upper left quadrant, an upper right quadrant, a lower left quadrant and a lower right quadrant, the upper left quadrant including working zones configured to provide overlay information in a first direction, the upper right quadrant including working zones configured to provide overlay information in a second direction that is different than the first direction, the lower right quadrant including working zones configured to provide overlay information in the first direction, the lower left quadrant including working zones configured to provide overlay information in the second direction.

51. The system as recited in claim 28 wherein each quadrant includes only four working zones, at least one providing overlay information in a first direction, at least one providing overlay information in a second direction, the other working zones providing overlay information in either direction.

52. A metrology system for determining the overlay between at least two separately generated patterns on a single or successive layers of a substrate, the system comprising:
an optical assembly for capturing images of an overlay mark that is separated into four quadrants, each of the four quadrants including at least four working zones that together substantially fill their quadrant, each quadrant including a first and second set of working zones and wherein the first set of the working zones are configured to provide overlay in a first direction, and a second set of working zones are configured to provide overlay information in a second direction, the first set of working zones being diagonally opposed with one another, the second set of working zones being diagonally opposed with one another and lying crosswise relative the first set of working zones, each of the working zones including a periodic structure comprised of a plurality of coarsely segmented elements positioned therein; and
a computer for analyzing the captured images to determine whether the overlay mark has an overlay error.

53. The system as recited in claim 52 wherein at least one of the working zones within each quadrant is generated separately from the other working zones in the quadrant.

54. The system as recited in claim 52 wherein at least two of the working zones within each quadrant e generated together, but separately from the other working zones in the quadrant.

55. The system as recited in claim 52 wherein the working zones in each set of working zones are separately generated.

56. The system as recited in claim 52 wherein the working zones in each set of working zones are generated together, but separately from other set of working zones.

57. The system as recited in claim 52 wherein the configuration of working zones in at least two of the quadrants is the same.

58. The system as recited in claim 52 wherein the configuration of working zones between all of the quadrants is different.

59. The system as recited in claim 52 wherein the overlay mark has a center and wherein the configuration of the working zones within each quadrant is rotationally symmetric at 0, 90, 180, 270 and 360 degrees around the center of the overlay mark.

60. The system as recited in claim 52 wherein the overlay mark has a center and wherein the configuration of the working zones within each quadrant is rotationally symmetric at 180 degrees around the center of the overlay mark.

61. A metrology system for determining the overlay between at least two separately generated patterns on a single or successive layers of a substrate, the system comprising:
an optical assembly for capturing images of a multidirectional overlay mark that is separated into four quadrants, each of the four quadrants including at least three separately generated working zones that are juxtaposed relative to one another and that together substantially fill the quadrant, the upper left quadrant including working zones configured to provide overlay information in a first direction, the upper right quadrant including working zones configured to provide overlay information in a second direction that is different than the first direction, the lower right quadrant including working zones configured to provide overlay information in the first direction, and the lower left quadrant including working zones configured to provide overlay information in the second direction, each of the working zones including a periodic structure comprised of a plurality of coarsely segmented elements positioned therein; and
a computer for analyzing the captured images to determine whether the multidirectional overlay mark has an overlay error.

62. The system as recited in claim 61 wherein the coarsely segmented elements of the periodic structures located within working zones of the same quadrant are aligned with one another.

63. The system as recited in claim 61 wherein the coarsely segmented elements are formed from a plurality of finely segmented elements configured to mimic one or more device features formed on the substrate with the plurality of finely segmented elements, the plurality of finely segmented elements being symmetrically positioned within each of the coarsely segmented lines.

64. The system as recited in claim 61 wherein the various separately generated working zones are oriented similarly within each of the quadrants such that each quadrant is rotationally symmetric at 0, 90, 180, 270 and 360 degrees around a center of the multidirectional overlay mark.

* * * * *

UNITED STATES PATENT AND TRADEMARK OFFICE
CERTIFICATE OF CORRECTION

PATENT NO. : 9,702,693 B2  
APPLICATION NO. : 15/136855  
DATED : July 11, 2017  
INVENTOR(S) : Ghinovker et al.

Page 1 of 1

It is certified that error appears in the above-identified patent and that said Letters Patent is hereby corrected as shown below:

In the Claims

Claim 31, Column 40, Line 48, change "claim rein" to -- claim 28 wherein --.

Claim 54, Column 42, Line 19, change "quadrant e" to -- quadrant are --.

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*